US012799443B2

(12) United States Patent
Pereira et al.

(10) Patent No.: US 12,799,443 B2
(45) Date of Patent: Nov. 17, 2026

(54) HUMAN VASCULARIZED INTEGRATED ORGAN SYSTEM AND APPLICATIONS THEREOF

(71) Applicant: 3D Systems, Inc., Rock Hill, SC (US)

(72) Inventors: Taciana Leticia Woellner Duarte Pereira, Houston, TX (US); Cassio da Silva Mello, Ivoti (BR); Ameya Ravindra Narkar, Houston, TX (US); Soon Seng Ng, Houston, TX (US); Clara Andrezzo, Stuttgart (DE); Kevin Janson, Houston, TX (US); Philip Crandell, Houston, TX (US); Queeny Dasgupta, Houston, TX (US); Yong Duk Han, Houston, TX (US); Alma Antonio, Houston, TX (US); Andre Vieira Pigatto, Houston, TX (US); Sammy S. Datwani, Pleasanton, CA (US)

(73) Assignee: 3D Systems, Inc., Rock Hill, SC (US)

( * ) Notice: Subject to any disclaimer, the term of this patent is extended or adjusted under 35 U.S.C. 154(b) by 0 days.

(21) Appl. No.: 18/778,914

(22) Filed: Jul. 19, 2024

(65) Prior Publication Data

US 2025/0101358 A1 Mar. 27, 2025

Related U.S. Application Data

(60) Provisional application No. 63/515,085, filed on Jul. 21, 2023.

(51) Int. Cl.

| | |
|---|---|
| ***B33Y 80/00*** | (2015.01) |
| ***C12M 1/00*** | (2006.01) |

(Continued)

(52) U.S. Cl.

CPC ............ *C12M 25/14* (2013.01); *B33Y 80/00* (2014.12); *C12M 23/38* (2013.01); *C12M 29/14* (2013.01);

(Continued)

(58) Field of Classification Search

CPC .. B01L 3/5027; B01L 3/502707; B33Y 80/00; C12M 25/14

See application file for complete search history.

(56) References Cited

U.S. PATENT DOCUMENTS

| | | | |
|---|---|---|---|
| 8,372,358 | B2 | 2/2013 | Groisman et al. |
| 8,580,546 | B2 | 11/2013 | Gonda et al. |

(Continued)

FOREIGN PATENT DOCUMENTS

| | | | |
|---|---|---|---|
| EP | 2526978 B1 | 12/2020 | |
| WO | WO-2002/053193 A2 | 7/2002 | |

(Continued)

OTHER PUBLICATIONS

Castaño ("Dynamic photopolymerization produces complex micro-structures on hydrogels in a moldless approach to generate a 3D intestinal tissue model") (Year: 2019).*

(Continued)

*Primary Examiner* — Michael A Marcheschi
*Assistant Examiner* — Nathan G Esperon
(74) *Attorney, Agent, or Firm* — Maynard Nexsen PC; John P. Zimmer

(57) ABSTRACT

A system for modeling organ-on-a-chip and other biological models includes a 3D-printed platform that includes an internal chip with bioprinted vascular and interstitial infill capable of being seeded with active cells such that the functioning of organs (for example, human organs) may be replicated accurately.

20 Claims, 58 Drawing Sheets

(51) Int. Cl.
*C12M 1/12* (2006.01)
*C12N 5/00* (2006.01)

(52) U.S. Cl.
CPC ........ *C12N 5/0068* (2013.01); *C12N 2533/54* (2013.01); *C12N 2537/10* (2013.01)

(56) References Cited

U.S. PATENT DOCUMENTS

| | | | | |
|---|---|---|---|---|
| 8,748,180 | B2 | 6/2014 | Shuler et al. | |
| 9,174,215 | B2 | 11/2015 | Vulto et al. | |
| 9,452,239 | B2 | 9/2016 | West et al. | |
| 10,179,896 | B2 * | 1/2019 | Baker | C12M 41/48 |
| 10,532,355 | B2 | 1/2020 | Trietsch et al. | |
| 11,344,877 | B2 | 5/2022 | Vulto et al. | |
| 11,402,367 | B2 | 8/2022 | Maoz et al. | |
| 11,554,373 | B2 | 1/2023 | Hickman et al. | |
| 11,566,231 | B2 | 1/2023 | Apostolou et al. | |
| 11,629,319 | B2 | 4/2023 | Vulto et al. | |
| 11,655,439 | B2 | 5/2023 | Guenat et al. | |
| 11,691,148 | B2 | 7/2023 | Jeon et al. | |
| 11,820,966 | B2 | 11/2023 | Hinojosa et al. | |
| 11,834,641 | B2 | 12/2023 | Levner et al. | |
| 11,920,116 | B2 | 3/2024 | Huh et al. | |
| 12,098,352 | B2 | 9/2024 | Nawroth et al. | |
| 2005/0095602 | A1 | 5/2005 | West et al. | |
| 2008/0257735 | A1 | 10/2008 | Jeon et al. | |
| 2010/0285082 | A1 | 11/2010 | Fernandez | |
| 2011/0008638 | A1 | 1/2011 | Miyawaki et al. | |
| 2011/0033918 | A1 * | 2/2011 | Asnaghi | C12M 25/14 435/289.1 |
| 2011/0034348 | A1 * | 2/2011 | Deutsch | C12M 23/12 506/14 |
| 2011/0280914 | A1 | 11/2011 | Prestwich et al. | |
| 2013/0164339 | A1 | 6/2013 | Murphy et al. | |
| 2014/0297199 | A1 | 10/2014 | Osten | |
| 2014/0322103 | A1 | 10/2014 | McDevitt et al. | |
| 2015/0024019 | A1 | 1/2015 | Ali et al. | |
| 2015/0377861 | A1 * | 12/2015 | Pant | C12M 23/34 435/395 |
| 2016/0046896 | A1 | 2/2016 | Ingber et al. | |
| 2016/0130543 | A1 * | 5/2016 | Daniele | C12M 29/10 264/41 |
| 2017/0145169 | A1 | 5/2017 | Oakey et al. | |
| 2017/0158997 | A1 * | 6/2017 | Ingber | C12M 23/16 |
| 2018/0002658 | A1 * | 1/2018 | Miller | C12N 5/0062 |
| 2018/0216074 | A1 | 8/2018 | Ingber et al. | |
| 2018/0345280 | A1 | 12/2018 | Vulto et al. | |
| 2018/0355298 | A1 | 12/2018 | Loskill et al. | |
| 2019/0032021 | A1 * | 1/2019 | Ingber | C12N 5/0697 |
| 2019/0062686 | A1 * | 2/2019 | Banaeiyan | C12M 21/08 |
| 2019/0160203 | A1 | 5/2019 | Gatenholm | |
| 2019/0247854 | A1 | 8/2019 | Ingber et al. | |
| 2019/0367872 | A1 | 12/2019 | Lutolf et al. | |
| 2019/0388887 | A1 * | 12/2019 | Le Berre | B01L 3/502715 |
| 2020/0038566 | A1 | 2/2020 | Johnson et al. | |
| 2020/0115667 | A1 | 4/2020 | Rylander et al. | |
| 2020/0149000 | A1 | 5/2020 | Wolter et al. | |
| 2020/0157483 | A1 * | 5/2020 | Ling | C12M 23/20 |
| 2020/0172844 | A1 * | 6/2020 | Betts-Lacroix | C12M 23/16 |
| 2020/0199514 | A1 | 6/2020 | Hauser et al. | |
| 2020/0263138 | A1 | 8/2020 | Blaeser | |
| 2020/0385661 | A1 | 12/2020 | Marx et al. | |
| 2021/0065913 | A1 | 3/2021 | Yuan et al. | |
| 2021/0108178 | A1 | 4/2021 | Huh et al. | |
| 2021/0330864 | A1 | 10/2021 | Gumennik et al. | |
| 2021/0348104 | A1 * | 11/2021 | Grigoryan | C12M 23/58 |
| 2021/0388301 | A1 | 12/2021 | Ingber et al. | |
| 2022/0002646 | A1 | 1/2022 | Han et al. | |
| 2022/0118446 | A1 * | 4/2022 | Swami | C12M 23/16 |
| 2022/0145259 | A1 | 5/2022 | Nguyen et al. | |
| 2022/0237930 | A1 | 7/2022 | Rando et al. | |
| 2022/0243157 | A1 | 8/2022 | Lin et al. | |
| 2022/0250055 | A1 | 8/2022 | Goyal et al. | |
| 2022/0259534 | A1 | 8/2022 | Watanabe et al. | |
| 2022/0290081 | A1 | 9/2022 | Jeong et al. | |
| 2022/0339195 | A1 | 10/2022 | Kealey | |
| 2022/0354993 | A1 | 11/2022 | Gatenholm | |
| 2022/0403339 | A1 | 12/2022 | Xiao et al. | |
| 2023/0011168 | A1 * | 1/2023 | Chen | B29C 64/10 |
| 2023/0058647 | A1 | 2/2023 | Cirit et al. | |
| 2023/0078827 | A1 | 3/2023 | Huh et al. | |
| 2023/0147702 | A1 | 5/2023 | Lee | |
| 2023/0393120 | A1 | 12/2023 | Kwon et al. | |
| 2023/0398803 | A1 * | 12/2023 | Roth | C09D 11/04 |
| 2023/0416661 | A1 | 12/2023 | Ingber et al. | |
| 2024/0018483 | A1 * | 1/2024 | Adriani | C12M 23/16 |
| 2025/0038884 | A1 | 1/2025 | Li et al. | |
| 2025/0250521 | A1 * | 8/2025 | Ranek | C12M 21/08 |

FOREIGN PATENT DOCUMENTS

| | | | |
|---|---|---|---|
| WO | WO-2022/116406 | A1 | 6/2022 |
| WO | WO-2022/165586 | A1 | 8/2022 |
| WO | WO-2023/283363 | A1 | 1/2023 |

OTHER PUBLICATIONS

Sung ("Poly(ethylene glycol) as a sensitive regulator of cell survival fate on polymeric biomaterials: the interplay of cell adhesion and pro-oxidant signaling mechanisms") (Year: 2010).*

Bedair, T. M. et al., Covalent immobilization of fibroblast-derived matrix on metallic stent for expeditious re-endothelialization, Jrnl. Indust. Engine. Chem., 70:385-393 2019 .

Congress, FDA Modernization Act 2.0, Senate Bill, 3 pages, Sep. 29, 2022.

Dal Sasso, E. et al., Covalent functionalization of decellularized tissues accelates endothelialization, Bioactive Materials, 6:3851-3864 2021 .

Daum, R. et al., Fibronectin Adsorption on Electrospun Synthetic Vascular Grafts Attracts Endothelial Progenitor Cells and Promotes Endothelialization in Dynamic In Vitro Culture, Cells, 9(778):1-29 2020

Emulate, Organ-chip Cancer Advance the development of novel immunotherapies and better understand the tumor microenvironment, website, accessed Sep. 9, 2024, <https://emulatebio.com/cancer-application/>.

Emulate, Organ-chip models Human-relevant models for complex biology, website, accessed Sep. 9, 2024, <https://emulatebio.com/organ-chips/>.

Grigoryan, B. et al., Multivascular networks and funcitonal intravascular topologies within biocompatible hydrogels, Sci., 364:458-464 2019 .

Jana, S., Endothelialization of cardiovascular devices, Acta Biomateria., 99:53-71 (2019).

Jensen, C. and Teng, Y., Is It Time to Start Transitioning From 2D to 3D Cell Culture?, Front. Mol. Biosci., 7(33):1-15 (2020).

Khalil, A. S. et al., Engineered tissues and strategies to overcome challenges in drug development, Adv. Drug Delivery Rev., 158:116-139 (2020).

Kinstlinger, I. S. et al., Perfusion and endothelialization of engineered tissues with patterened vascular networks, Nat. Protoc., 16(6):3089-3113 (2021).

Lee, H. et al., Freeform 3D printing of vascularized tissues: Challenges and strategies, Jrnl. Tissue Engin., 12:1-34 (2021).

Li, P. et al., Phospholipid-based multifunctional coating via layer-by-layer self-assembly for biomedical applications, Mat. Sci. Engin., 116(111237):1-12 (2020).

Miller, J. S. et al., Rapid casting of patterned vascular networks for perfusable engineered 3D tissues, Nat. Mater., 11(9):768-774 (2012).

Mimetas, Case study: 3D immune cell migration towards a tumor microenvironment, website, accessed Sep. 9, 2024, <https://www.mimetas.com/en/case-study-3d-immune-cell-migration-towards-a-tumor-microenvironment/>.

Mimetas, Perfused Tubules, website, accessed Sep. 9, 2024, <https://www.mimetas.com/en/perfused-tubules/>.

National Centerfor Advancing Translational Sciences, Clinical Trials on a Chip, 6 pages, accessed Sep. 9, 2024.

(56) References Cited

OTHER PUBLICATIONS

Paek, J. et al., Microphysiological Engineering of Self-Assembled and Perfusable Microvascular Beds for the Production of Vascularized Three-Dimensional Human Microtissues, ACS Nano, 13:7627-7643 2019 .
Swagel, P. L., Research and Development in the Pharmaceutical Industry, Publication, Congressional Budget Office, posted Apr. 2021.
Synvivo, SynTumor 3D Cancer Model—Recreating the Tumor Microenvironment, accessed Sep. 9, 2024, <https://www.synvivobio.com/syntumor/>.
Trietsch, S. J. et al., Membrane-free culture and real-time barrier integrity sessment of perfused intestinal epithelium tubes, Nat. Comm., 18(262):1-8 2017 .
Vivodyne, Organ Models Lifelike, functional human organ tissues, website, accessed Sep. 9, 2024, <https://www.vivodyne.com/human-organ-models>.
Zhao, W. et al., Microfluidic devices for neutrophil chemotaxis studies, J. Transl. Med., 18(168):1-19 (2020).
Chyzy, A. et al., Hydrogels as Potential Nano-, Micro- and Macro-Scale Systems for Controlled Drug Delivery, Materials (Basel), 13(1):188 (2020).
Invitation to Pay Additional Fees for PCT/US2024/038913, 4 pages (mailed Sep. 26, 2024).
Johnston, T.G. et al., Compartmentalized microbes and co-cultures in hydrogels for on-demand bioproduction and preservation, Nature Communications, 11(1):563 (2020).
Papaioannou, T. G. et al., 3D Bioprinting Methods and Techniques: Applications on Artificial Blood Vessel Fabrication, Acta. Cardiol. Sin., 35:284-289 (2019).
"Organ-on-a-chip engineering: Toward bridging the gap between lab and industry", Qasem Ramadan and Mohammed Zourob, Biomicrofluidics 14, 041501 (2020); doi: 10.1063/5.0011583, published online: Jul. 14, 2020 (23 pages).
"Human multi-organ chip co-culture of bronchial lung culture and liver spheroids for substance exposure studies", Katharina Schimek, et al, Scientifo Reports, naturesearch, 2020 10:7865, https://doi.org/10.1038/s41598-020-64219-6, www.nature.com/scientificreports (13 pages).
"Scaling and systems biology for integrating multiple organs-on-a-chip"; Lab on a Chip, RSC Publishing, Lab Chip, 2013, 13, pp. 3496, John P. Wikswo, et al., DOI: 10.1039/c3lc50243k, www.rsc.org/loc; The Royal Society of Chemistry 2013, pp. 3496-3511.
"Robotic fluidic coupling and interrogation of multiple vascularized organ chips", Novak, Richard (et al.), Nature Biomedical Engineering, Apr. 2020, vol. 4, Issue 4, pp. 407-420; www.nature.com/natbiomedeng; https://doi.org/10.1038/s41551-019-0497-x.
"Engineered Vasculature for Organ-on-a-Chip Systems", Research Bio-Manufacturing-Review, Abdellah Aazmi, et al., Engineering 9 (2022) pp. 131-147, https://doi.org/10.1016/j.eng2021.06.020; journal homepage: www.elsevier.com/locate/eng, http://creativecommons.org/licensees/by-nc-nd/4.0/.
BD Biosciences, BD APO-Cy7 Mouse Anti-Human CD4, Product, 4 Pages. <https://www.bdbiosciences.com/en-us/products/reagents/flow-cytometry-reagents/clinical-discovery-research/single-color-antibodies-ruo-gmp/apc-cy-7-mouse-anti-human-cd4.341095?tab=product details>, 2025.
BD Biosciences, BD Horizon BV421 Mouse Anti-Human CD3, Product, 3 Pages. <https://www.bdbiosciences.com/en-us/products/reagents/microscopy-imaging-reagents/immunofluorescence-reagents/bv421-mouse-anti-human-cd3.562426?tab=product_details>, 2025.
BD Biosciences, BD OptiBuild BV650 Mouse Anti-Human PD-1 (0279), Product, 3 Pages. <https://www.bdbiosciences.com/en-us/products/reagents/flow-cytometry-reagents/research-reagents/single-color-antibodies-ruo/bv650-mouse-anti-human-pd-1-cd279.752738?tab=product_details>, 2025.
BD Biosciences, BD Pharmingen PE Mouse Anti-Human CD28, Product, 3 Pages. <https://www.bdbiosciences.com/en-us/products/reagents/flow-cytometry-reagents/research-reagents/single-color-antibodies-ruo/pe-mouse-anti-human-cd28.555729?tab=product details>, 2025.
BD Biosciences, BD Pharmingen PerCP-Cy5.5 Mouse Anti-Human CD8, Product, 3 Pages. <https://www.bdbiosciences.com/en-us/products/reagents/flow-cytometry-reagents/research-reagents/single-color-antibodies-ruo/percp-cy-5-5-mouse-anti-human-cd8.560662?tab=product_details>, 2025.
Chen, M. et al., DILIrank: the largest reference drug list ranked by the risk for developing drug-induced liver injury in humans, Drug Discov., 21 (4):648-653 (2016).
Cohen, A. D. et al., Gemtuzumab ozogamicin (mylotarg) monotherapy for relapsed AML aftel hematopoietic stem cell transplant: efficacy and incidence of hepatic veno-occlusive disease, Bone Marrow Trans., 30:23-28 (2002).
Dirven, H. et al., Performance of preclinical models in predicting drug-induced liver injury in humans: a systematic review, Sci. Repo., 11(6403):1-19 (2021 ).
Garside, H. et al., Evaluation of the use of imaging parameters for the detection of compound-induced hepatotoxicity in 384-well cultures of HepG2 cells and cryopreserved primary human hepatocytes, Toxicology in Vitro, 28:171-181 (2014).
Guffroy, M. et al., Liver Microvascular Injury and Thrombocytopenia of Antibody-Calicheamicin Conjugates in Cynomolgus Monkeys-Mechanism and Monitoring, Clin. Cancer Res., 23(7):1760-1770 (2017).
International Search Reportfor PCT/US2024/038913, 5 pages (mailed Jan. 13, 2025).
Loewa, A. et al., Human disease models in drug development, Nat. Rev. Bioengin., 545-559 (2023).
Proctor, W. R. et al., Utility of spherical human liver microtissues for prediction of clinical drug-induced liver injury, Arch. Toxicol., 91:2849-2863 (2017).
Rajvanshi, P. et al., Hepatic sinusoidal obstruction after gemtuzumab ozogamicin (Mylotarg) therapy, Blood, 99(7):2310-2314 (2002).
Ricart, A. D., Antibody-drug conjugates of calicheamicin derivative: gemtuzumab ozogamicin and inotuzumab ozogamicin, Clin. Can. Res., 17(20):6417-6427 (2011).
Trinconi, C et al., Human vascularized liver-on-a-chip platform for drug discovery and liver injury assessment, Abstract 4628, 63rd Annual Meeting of Society of Toxicology, Mar. 10-14, 2024.
Walker, P. et al., The evolution of strategies to minimise the risk of human drug-induced liver injury (DILI) in drug discovery and development, Arch. Toxicol., 94:2559-2585 (2020).
Waring, M. J. et al., An analysis of the attrition of drug candidates from four major pharmaceutical companies, Nat. Rev. Drug Discov., 14:475-486 (2015).
Written Opinion for PCT/US2024/038913, 8 pages (mailed Jan. 13, 2025).

* cited by examiner

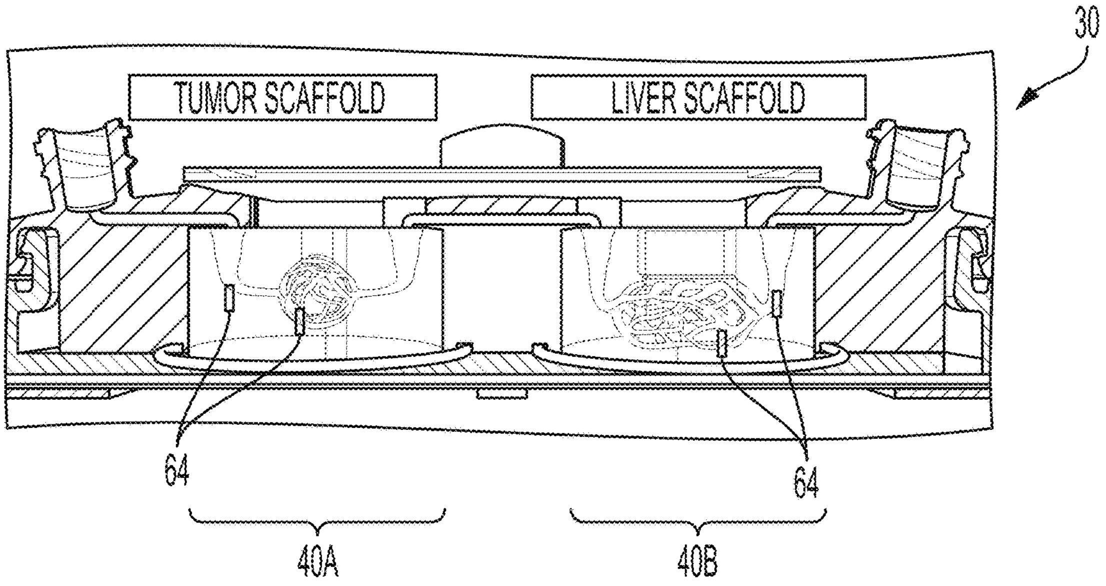
FIG. 19
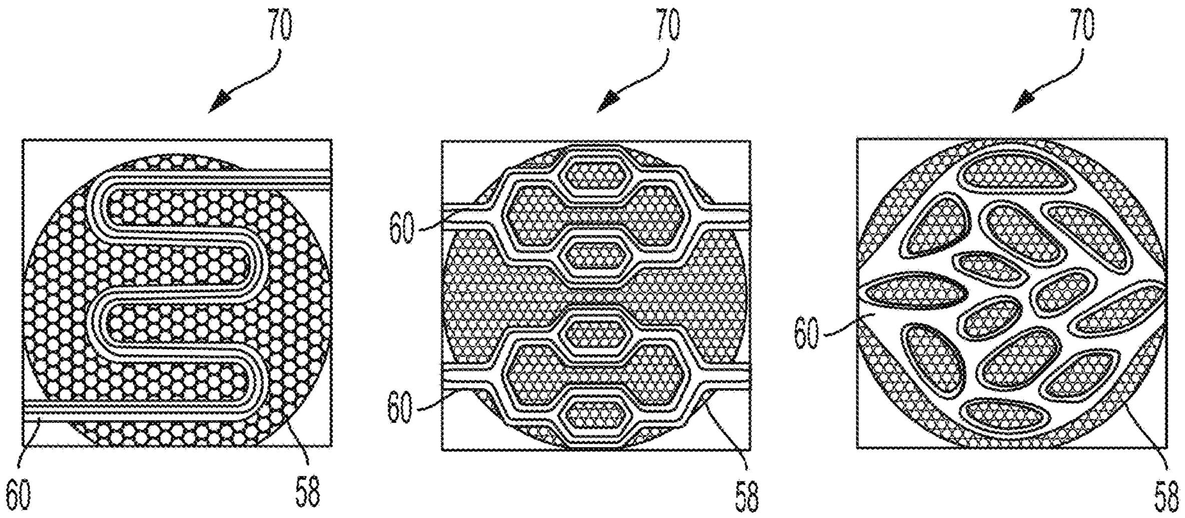
FIG. 20A
FIG. 20B
FIG. 20C

HUMAN VASCULARIZED INTEGRATED ORGAN SYSTEM AND APPLICATIONS THEREOF

CROSS-REFERENCE TO RELATED APPLICATIONS

This application claims priority to U.S. Provisional Patent Application No. 63/515,085 filed Jul. 21, 2023, the disclosure of which is incorporated by reference herein in its entirety.

BACKGROUND OF THE DISCLOSURE

Drug and therapeutics development are generally time-consuming and costly endeavors. In vivo testing of new drugs involves a phased, highly-regulated approach that helps to ensure the efficacy of the underlying drugs and/or therapies, and helps to ensure the safety of patients upon whom they are being test, but also often entails multi-billion dollar (and multi-year) regulatory approval processes. In silico modeling of drugs and therapies can also be time-consuming and costly, and can lead to results that are inherently less accurate than those derived from in vivo testing. The success of in silico (i.e., computer) modeling and testing is also dependent on the underlying data upon which those computer models are based. When in vivo testing and in silico modeling result in counter-indications and/or inconclusive results, years of development time and millions (or even billions) of dollars of research and development investments are often lost.

SUMMARY OF THE DISCLOSURE

The present disclosure presents systems, methodologies, and apparatuses that enable quick prototyping and modeling of organs, tissues, cells, biological processes, and other mechanisms, via a flexible platform that allows for adaptive and/or iterative build and refinements of models. The present embodiments include an ecosystem that produces a platform for creating physical, synthetic models of organs, tissues, cells, via bioprinting of scaffolds that supports internal passages that approximate the geometries of human vasculatures. The vasculatures may be coated with biological materials such as endothelial cells and may be operatively coupled to live tissues and cells seeded in an interstitial space within the scaffold. Accordingly, the synthetic physical models are seeded with live cells and/or tissues. Scaffolding enables delivery of biologically active materials to the cells and/or tissue(s) via fluid(s) flowing through the vasculature, and transport through vasculature walls. The ecosystem includes control of environmental factors used for assaying synthetic tissue and/or organ models, real-time tracking of biomarkers via sensors, ability to rapidly image tissues and/or cells, processing of assay data, machine learning tools for diagnosing results, and updating of scaffold print files such that updated models can be reprinted, assays may be rerun, and the results may be reanalyzed. Therefore, the entire ecosystem enables adaptive learning and quick re-prototyping such that learnings from assays being performed can be immediately incorporated into future scaffold designs for further assaying and examination. As a result, the disclosed platform and ecosystem allow highly accurate synthetic organs to be rapidly created and assayed, thereby enabling expedited drug discovery and early drug candidate screening.

In one aspect, the present embodiments are directed to a system for modeling organ-on-a-chip and other biological models includes a 3D-printed platform that includes an internal chip with bioprinted vascular and interstitial infill capable of being seeded with active cells such that the functioning of organs (for example, human organs) may be replicated accurately.

In another aspect, the present embodiments are directed to a system that enables the modeling of an organ, a tissue, a cell, a biological process, and/or other mechanism comprising: a bioprinted entity; a cell associated with the bioprinted entity and/or seeded therein; and optionally comprising vasculature.

In another aspect, the present embodiments are directed to an ecosystem for designing, building, and refining physical models or platforms that replicate the functioning of an organ that may be used to for drug discovery and for assessing the effectiveness of various therapies comprising: a bioprinted entity; a cell associated with the bioprinted entity and/or seeded therein; and optionally comprising vasculature.

In another aspect, the present embodiments are directed to a system comprising a scaffold, a manifold, and a sensor, wherein the scaffold comprises: vasculature; an interstitial space; and wherein the system allows continuous monitoring.

In another aspect, the present embodiments are directed to an organ-on-a-chip platform assembly comprising: a platform base; a glass base sized to be seated with the platform base; at least one chip supported by the glass base; a case comprising at least one recess sized such that the at least one chip may be inserted into the at least one recess, the case comprising size walls, at least one fluid inlet, at least one fluid outlet, and multiple internal passages fluidly connecting the fluid inlet and/or the fluid outlet to the at least one chip; a glass cover configured to be seated on top of the case and to cover the at least one chip; and a cover retainer for holding the glass cover to the case.

In some embodiments, the assembly includes: at least one O-ring for sealing the at least one chip to the glass cover; a clip slidably and laterally engageable with the case to hold the assembly together; a first vasculature comprising a first inlet, a first outlet, a first network of passages fluidly coupling the first inlet to the first outlet; and/or a second vasculature comprising a second inlet, a second outlet, a second network of passages fluidly coupling the second inlet to the second outlet, wherein the first network of passages is interlinked with and/or intertwined with the second network of passages, and wherein the first vasculature is not fluidly coupled to the second vasculature.

In some embodiments, the chip comprises a 3D-printed internal vasculature comprising a vasculature inlet and a vasculature outlet.

In some embodiments, the vasculature comprises a network of passages fluidly coupling the vasculature inlet to the vasculature outlet.

In some embodiments, the vasculature is formed within a 3D-printed hydrogel scaffold.

In some embodiments, the chip further comprises an interstitial space disposed within and/or around the network of passages.

In some embodiments, the chip further comprises interstitial infill disposed within the interstitial space, the interstitial infill comprising a 3D-printed repeating structure for supporting one or more active cells.

In some embodiments, the assembly includes active cells seeded within (1) interior walls of the vasculature, and (2) the interstitial space.

In some embodiments, the assembly at least one fluid disposed within, and/or flowing through, the internal vasculature.

In some embodiments, the assembly includes a first biological fluid disposed within and/or flowing through the first vasculature; and a second biological fluid disposed within and/or flowing through the second vasculature, wherein the first biological fluid is different than the second biological fluid, and wherein each of the first vasculature and second vasculature are operatively coupled to the interstitial space.

In another aspect, the present disclosure is directed to a system that enables the modeling of an organ, a tissue, a cell, a biological process, and/or other mechanism comprising: a bioprinted entity; a cell associated with the bioprinted entity and/or seeded therein; and optionally comprising vasculature.

In another aspect, the present disclosure is directed to an ecosystem for designing, building, and refining physical models or platforms that replicate the functioning of an organ that may be used to for drug discovery and for assessing the effectiveness of various therapies comprising: a bioprinted entity; a cell associated with the bioprinted entity and/or seeded therein; and optionally comprising vasculature.

In another aspect, the present disclosure is directed to a system comprising a scaffold, a manifold, and a sensor, wherein the scaffold comprises: vasculature; an interstitial space; and wherein the system allows continuous monitoring.

In some embodiments, the scaffold comprises a hydrogel.

In some embodiments, the scaffold comprises a hydrogel comprising an inert polymer.

In some embodiments, the vasculature is perfused with a cell; and wherein, following perfusion, the cell is associated with the vasculature forming a cell layer.

In some embodiments, the cell is a mammalian cell.

In some embodiments, the cell is an endothelial cell.

In some embodiments, the interstitial space has a pattern selected from an orthorhombic pattern, a cubic pattern, a hexagonal lattice, and a pattern with spherical voids.

In some embodiments, the interstitial space comprises an interstitial infill.

In some embodiments, the interstitial infill comprises a hydrogel.

In some embodiments, the interstitial infill comprises a hydrogel and a cell.

In some embodiments, the hydrogel is bonded to the cell.

In some embodiments, the bond is selected from a covalent and an ionic bond.

In some embodiments, the bond is a covalent bond.

In some embodiments, the bond is an ionic bond.

In some embodiments, the cell is a mammalian cell.

In another aspect, the present disclosure is directed to a method of monitoring a characteristic of a biologically active material comprising a system comprising an organ-on-a-chip, wherein the organ-on-a-chip comprises: a bioprinted entity; and a cell associated with the bioprinted entity and/or seeded therein.

In some embodiments, the monitoring is continuous.

In another aspect, the present disclosure is directed to a method of modeling physiological conditions of an organ comprising an organ-on-chip, wherein the organ-on-a-chip comprises: a bioprinted entity; and a cell associated with the bioprinted entity and/or seeded therein.

In another aspect, the present disclosure is directed to a method of generating a 3D printed microphysiological system comprising a multi-cellular environment.

In another aspect, the present disclosure is directed to an organ-on-a-chip comprising: a bioprinted entity comprising a polymer; a cell associated with the bioprinted entity and/or seeded therein; and optionally further comprising vasculature.

In another aspect, the present disclosure is directed to a liver-on-a-chip comprising: a bioprinted entity comprising a polymer; a liver cell associated with the bioprinted entity and/or seeded therein; and optionally further comprising vasculature.

In another aspect, the present disclosure is directed to a kit comprising an organ-on-a-chip used for monitoring a detectable moiety, wherein the organ-on-a-chip models physiological conditions.

In another aspect, the present disclosure is directed to a tumor-on-a-chip comprising: a bioprinted entity comprising a polymer; a tumor cell associated with the bioprinted entity and/or seeded therein; and optionally further comprising vasculature.

In another aspect, the present disclosure is directed to a method of functionalizing a polymer and/or hydrogel surface, the method comprising: providing at least one polymer and/or hydrogel surface; pre-coating the at least one polymer and/or hydrogel surface with a precursor; irradiating the pre-coated surface; coating the irradiated surface with a bioactive coating; performing at least one post-coating step to enable bioconjugation of the bioactive coating with the coated surface.

In some embodiments, the method includes pre-washing the at least one polymer and/or hydrogel surface prior to precoating.

In some embodiments, the at least one post-coating step comprises at least one of incubating, sterilizing, irradiating, and washing the coated surface.

In some embodiments, the at least one precursor comprises acrylated-PEG1k-NHS.

In some embodiments, irradiating the pre-coated surface comprises irradiating the pre-coated surface with a light source activated at a wavelength of 405 nm.

In some embodiments, the bioactive coating comprises at least one of gelatin methacrylate (GelMA), collagen methacrylate (ColMA), and collagen type I.

In some embodiments, the at least one precursor comprises a cytocompatible photoinitiator.

In some embodiments, the cytocompatible photoinitiator is water soluble.

In some embodiments, the bioactive coating comprises at least one acrylate.

In some embodiments, the method includes seeding live cells on the coated surface.

In some embodiments, the at least one polymer and/or hydrogel surface is part of a three-dimensional structure comprising at least one internal passage, the at least one internal passage coated with a bioactive coating, the method further comprising: perfusing living cells through the at least one internal passage, thereby seeding the live cells on one or more interior walls of the at least one internal passage.

In some embodiments, the live cells comprise at least one of an endothelial cell, a biliary endothelial cell, a cholangiocyte, a liver parenchymal cell, a hepatocyte (HC), a primary human hepatocyte (PHH), a heptic stellate cell (HSCs), a Kupffer cell (KC), a liver sinusoidal endothelial cell (LSEC), a mucous cell, a parietal cell, a chief cell, an endocrine cell (e.g., a G cell, a D cell, a enterochromaffin cell, a EC-like cell, a X/A cell), a columnar epithelial cell, a cardiac fibroblast (CF), a cardiomyocyte, a smooth muscle cell, an enterocyte, a goblet cell, a Paneth cell, a stem cell, a neuron, a glia, a keratinocyte, a melanocyte, a Merkel cell, a Langerhan cell, a germ cell, a stromal cell, a seminiferous tubule, a Leydig cell, a tubule epithelial cell, a macula densa cell, a glomerular endothelial cell, a podocyte, a mesangial cell, a parietal epithelial cell, an immortalized cell (e.g. a 3T3 cell, a A549 cell, a HeLa cell, a HEK 293 cell, a HEK 293T cell, a Huh7 cell, a Jurkat cell, a OK cell, a Ptk2 cell, a Vero cell), a patient-derived cell (e.g., a tumor cell), a T cell, a peripheral blood mononuclear cell (PBMC), and/or an induced pluripotent stem cell (iPSC).

In some embodiments, the method further includes using a peristaltic pump to seed live cells within the at least one internal passage; and using the peristaltic pump to perfuse media through the at least one internal passage.

In some embodiments, a lower volumetric flow rate is used for seeding live cells within the at least one internal passage than for perfusing media through the at least one internal passage.

In another aspect, the present disclosure is directed to a bioactive coating comprising: collagen type I in a range from about 0.2% to about 8.0% by volume; collagen type IV in a range from about 4.0% to about 40.0% by volume; fibronectin in a range from about 2.0% to about 90.0% by volume; and DPBS (1×) in a range from about 0.5% to about 95.0% by volume.

In another aspect, the present disclosure is directed to a bioactive coating for use in coating two-dimensional surfaces comprising: collagen type I in a range from about 0.2% to about 0.6% by volume; collagen type IV in a range from about 4.0% to about 13.0% by volume; fibronectin in a range from about 2.0% to about 7.0% by volume; and DPBS (1×) in a range from about 50.0% to about 95.0% by volume.

In another aspect, the present disclosure is directed to a bioactive coating for use in coating three-dimensional surfaces comprising collagen type I in a range from about 2.3% to about 8.0% by volume; collagen type IV in a range from about 12.0% to about 40.0% by volume; fibronectin in a range from about 35.0% to about 90.0% by volume; and DPBS (1×) in a range from about 0.5% to about 3.0% by volume.

In some embodiments, the vasculature described herein comprises micropores.

In some embodiments, the micropores comprise a diameter of about 40 μm to about 60 μm (e.g., about 35 μm to about 65 μm) (e.g., about 30 μm to about 70 μm) determined by the thickness of the channel walls—and is fixed at 100, 150, or 200 μm.

In some embodiments, the micropores comprise a length of 100 μm.

In some embodiments, the micropores comprise a length of 150 μm.

In some embodiments, the micropores comprise a length of 200 μm.

In some embodiments, the scaffold is functionalized using the method(s) described herein.

In another aspect, the present disclosure is directed to an organ-on-a-chip cartridge comprising: at least one fluid inlet, at least one fluid outlet, at least one chip slot, at least one chip slot inlet, at least one chip slot outlet, and multiple internal channels fluidly connecting the fluid inlet and/or the fluid outlet to the chip slot inlet and/or the chip slot outlet.

In some embodiments, the at least one chip inlet splits into two chip inlet sub-channels, and wherein the at least one chip outlet channel split into two chip outlet sub-channels.

In some embodiments, the cartridge includes a media reservoir.

In another aspect, the present disclosure is directed to an organ-on-a-chip platform assembly comprising: a well plate, a cartridge comprising at least one fluid inlet, at least one fluid outlet, at least one chip slot, at least one chip slot inlet, at least one chip slot outlet, and multiple internal channels fluidly connecting the fluid inlet and/or the fluid outlet to the chip slot inlet and/or the chip slot outlet, wherein the cartridge is configured to be inserted into at least one well of the well plate; at least one chip supported by the at least one chip slot and the at least one well of the well plate, and a cover configured to be seated on top of the cartridge and to cover the at least one chip.

In some embodiments, the cartridge further comprises a media reservoir.

In some embodiments, the cartridge includes: a first chip slot, a first fluid inlet, a first fluid outlet, and first multiple internal channels fluidly connecting the first fluid inlet and/or the first fluid outlet to the first chip slot inlet and/or the first chip slot outlet, a second chip slot, a second fluid inlet, a second fluid outlet, and second multiple internal channels fluidly connecting the second fluid inlet and/or the second fluid outlet to the second chip slot inlet and/or the second chip slot outlet.

In some embodiments, the assembly includes a first biological fluid disposed within and/or flowing through a first chip inserted in a first chip slot; and a second biological fluid disposed within and/or flowing through a second chip inserted in the second chip slot, wherein the first biological fluid is different than the second biological fluid.

In some embodiments, the assembly includes imaging inserts, wherein the imaging inserts secure and/or set the orientation of the at least one chip.

In another aspect, the present disclosure is directed to a system comprising: a multi-part assembly comprising: at least one inlet flow line configured to deliver a fluid to an interior volume of the multi-part assembly; at least one outlet flow line configured to deliver the fluid from the interior volume of the multi-part assembly; a chip housed within the interior volume multi-part assembly, the chip comprising: at least one inlet flow passage disposed therein and fluidly coupled to the at least one inlet flow line; and at least one outlet flow passage disposed therein and fluidly coupled to the at least one outlet flow line, wherein the at least one inlet flow passage transitions to the at least one outlet flow passage within an interstitial space disposed within the chip.

In some embodiments, each of the multi-part assembly and the chip are formed via an additive manufacturing process.

In some embodiments, each part of the multi-part assembly is composed of a metallic or a polymer material, the chip is composed of a hydrogel material, and each part of the multi-part assembly is composed of a harder material than the hydrogel material.

In some embodiments, each of the at least one inlet flow passage and the at least one outlet flow passage comprises at least two inlet or outlet flow passages, thereby forming at least two unconnected fluid flow passages through the chip, and each of the at least two unconnected fluid flow passages contains a different fluid.

In some embodiments, each of the at least one inlet flow passage and the at least one outlet flow passage comprises a single respective inlet or outlet portion which branches into a network of connected flow passages, the network of inlet flow passages fluidly connected to the corresponding network of outlet flow passages.

In some embodiments, at least one of the at least one inlet passage and the at least one outlet passage comprises at least one micropore disposed therein in a portion of the passage disposed within the interstitial space.

In some embodiments, the at least one micropore comprises an internal diameter in a range from about 40 μm to about 60 μm.

In some embodiments, the system includes at least one precursor comprising acrylated-PEG1k-NHS disposed on the chip.

In some embodiments, the at least one precursor further comprises a photoinitiator.

In some embodiments, the system includes at least one bioactive coating comprising at least one of at least one of gelatin methacrylate (GelMA), collagen methacrylate (ColMA), and collagen type I.

In some embodiments, the system includes at least one live cell disposed within the interstitial space and/or attached to an interior surface of the at least one inlet flow passage and/or the at least one outlet flow passage.

In some embodiments, the at least one live cell comprises at least one of an endothelial cell, a biliary endothelial cell, a cholangiocyte, a liver parenchymal cell, a hepatocyte (HC), a primary human hepatocyte (PHH), a heptic stellate cell (HSCs), a Kupffer cell (KC), a liver sinusoidal endothelial cell (LSEC), a mucous cell, a parietal cell, a chief cell, an endocrine cell (e.g., a G cell, a D cell, a enterochromaffin cell, a EC-like cell, a X/A cell), a columnar epithelial cell, a cardiac fibroblast (CF), a cardiomyocyte, a smooth muscle cell, an enterocyte, a goblet cell, a Paneth cell, a stem cell, a neuron, a glia, a keratinocyte, a melanocyte, a Merkel cell, a Langerhan cell, a germ cell, a stromal cell, a seminiferous tubule, a Leydig cell, a tubule epithelial cell, a macula densa cell, a glomerular endothelial cell, a podocyte, a mesangial cell, a parietal epithelial cell, an immortalized cell (e.g. a 3T3 cell, a A549 cell, a HeLa cell, a HEK 293 cell, a HEK 293T cell, a Huh7 cell, a Jurkat cell, a OK cell, a Ptk2 cell, a Vero cell), a patient-derived cell (e.g., a tumor cell), a T cell, a peripheral blood mononuclear cell (PBMC), and/or an induced pluripotent stem cell (iPSC).

In some embodiments, the system includes a fluid reservoir fluidly coupled downstream of the at least one inlet flow line and upstream of the at least one inlet flow passage.

In some embodiments, the system includes a pump disposed downstream of the fluid reservoir and upstream of the at least one inlet flow passage.

In some embodiments, the system includes a covalent linker attached to the hydrogel material; and collagen attached to the covalent linker.

In another aspect, the present disclosure is directed to a method of functionalizing a hydrogel surface, the method comprising: providing at least one hydrogel surface; precoating the at least one hydrogel surface with a precursor; irradiating the pre-coated surface; coating the irradiated surface with a bioactive coating comprising at least one of gelatin methacrylate (GelMA), collagen methacrylate (ColMA), and collagen type I; performing at least one post-coating step to enable bioconjugation of the bioactive coating with the coated surface.

In some embodiments, the at least one post-coating step comprises at least one of incubating, sterilizing, irradiating, and washing the coated surface.

In some embodiments, the at least one precursor comprises acrylated-PEG1k-NHS.

In some embodiments, irradiating the pre-coated surface comprises irradiating the pre-coated surface with a light source activated at a wavelength of 405 nm.

In some embodiments, wherein the at least one precursor comprises a cytocompatible photoinitiator.

In some embodiments, the system includes at least one sampling port and/or fluid sampling line fluidly coupled to at least one of the reservoirs, the outlet flow line, the outlet flow passage, the interstitial space, and/or another system flow passage.

In some embodiments, the system includes a removable top cover or lid enabling access to the interior volume, wherein the interstitial space being accessible when the top cover or lid is removed.

BRIEF DESCRIPTION OF THE DRAWINGS

FIG. 19 illustrates a view of organ chips within a platform assembly, according to aspects of the present embodiments.

FIGS. 20A, 20B, and 20C illustrate views of vasculature configurations, according to aspects of the present embodiments.

FIG. 55B depicts HUVEC cells attached to a surface coated with AN14 hydrogel containing polyethylene glycol diacrylate and gelatin methacrylate. FIG. 55C depicts HUVEC cells attached to a surface coated with AN14 hydrogel containing polyethylene glycol diacrylate and gelatin methacrylate, primed with NHS1 and coated with collagen type I (Col1) and fibronectin (F). FIG. 55D depicts HUVEC cells attached to a surface coated with AN14 hydrogel containing polyethylene glycol diacrylate and gelatin methacrylate, primed with NHS1 and coated with collagen type IV and fibronectin. FIG. 55E depicts HUVEC cells attached to a surface coated with synthetic hydrogel primed with NHS and coated with Col1 and fibronectin. FIG. 55F depicts HUVEC cells attached to a surface coated with SYNT hydrogel primed with NHS1 and coated with collagen type IV and fibronectin.

FIG. 60A illustrates the lumen/vasculature inlet and FIG. 60B illustrates the lumen/vasculature outlet. Both have been washed with medium, according to aspects of the present embodiments.

FIG. 60C illustrates the lumen/vasculature inlet and FIG. 60D illustrates the lumen/vasculature outlet. Neither has been washed with medium, according to aspects of the present embodiments.

FIG. 61A depicts GFP expressing cells attached throughout a vasculature of a structure described herein. FIG. 61B depicts cells growing within a vasculature, visualized by cell-specific markers Ve-Cadherin (red) 993, CD31 (purple) 995, and Hoechst (blue) 997.

DETAILED DESCRIPTION OF THE DISCLOSURE

Definitions

Figure 1:
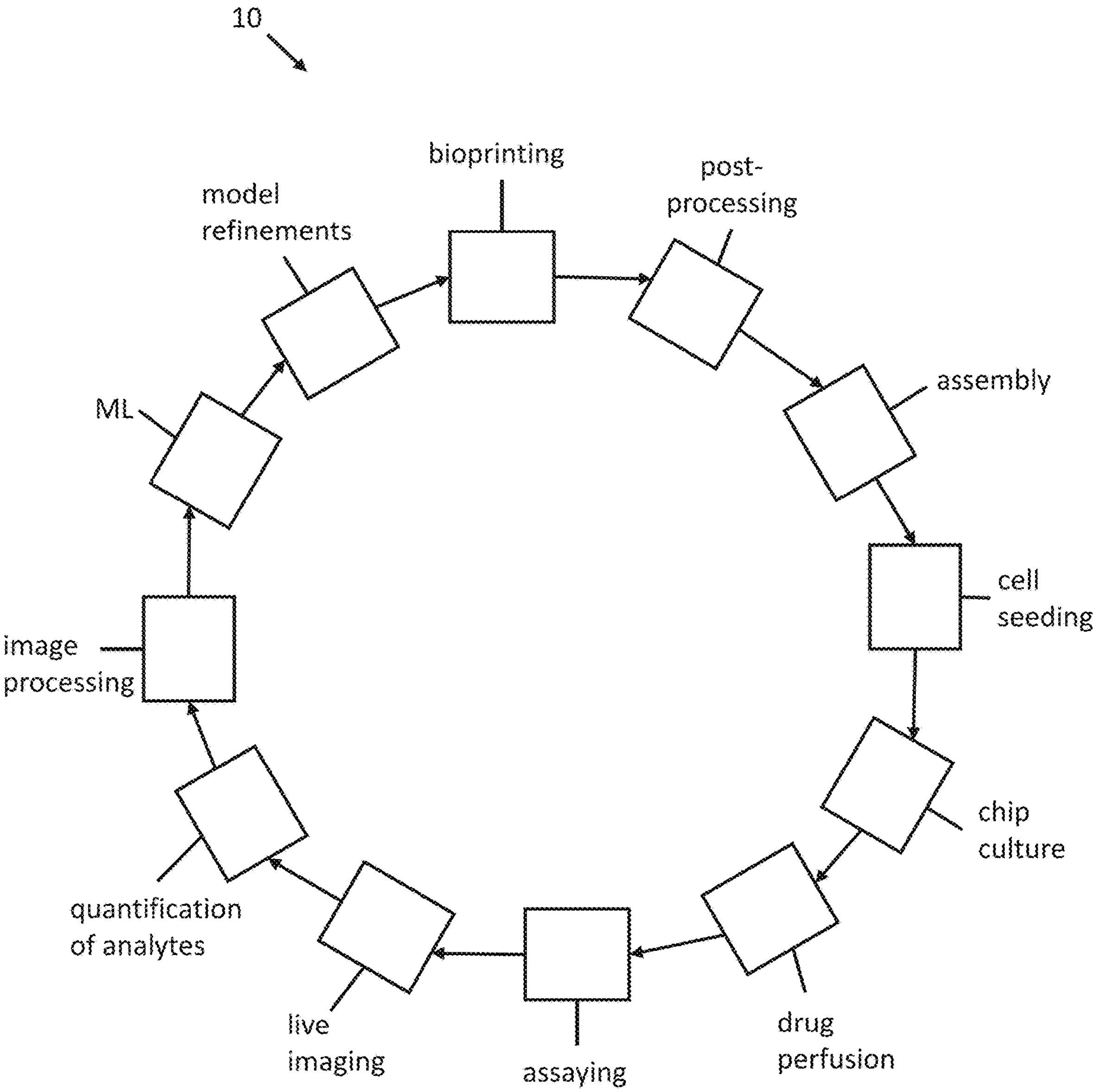
FIG. 1 illustrates an ecosystem for creating organ-on-a-chip and other biological models, according to aspects of the present embodiments.

In order for the present disclosure to be more readily understood, certain terms are defined below. Unless defined otherwise herein, technical and scientific terms used herein have the same meaning as commonly understood by one of ordinary skill in the art to which this disclosure is related.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

It is to be noted that the term "a" or "an" entity refers to one or more of that entity; for example, "a cell" is understood to represent one or more cells. As such, the terms "a" (or "an"), "one or more," and "at least one" can be used interchangeably herein.

Agent: As used herein, the term "agent", may refer to a compound, molecule, or entity of any chemical class including, for example, a small molecule, polypeptide, nucleic acid, saccharide, lipid, metal, or a combination or complex thereof. In some embodiments, the term "agent" may refer to a compound, molecule, or entity that comprises a polymer. In some embodiments, the term may refer to a compound or entity that comprises one or more polymeric moieties. In some embodiments, the term "agent" may refer to a compound, molecule, or entity that is substantially free of a particular polymer or polymeric moiety. In some embodiments, the term may refer to a compound, molecule, or entity that lacks or is substantially free of any polymer or polymeric moiety.

Aliphatic: As used herein, "aliphatic" means a straight-chain (i.e., unbranched) or branched, substituted or unsubstituted hydrocarbon chain that is completely saturated or that contains one or more units of unsaturation, or a monocyclic hydrocarbon, bicyclic hydrocarbon, or polycyclic hydrocarbon that is completely saturated or that contains one or more units of unsaturation that has a single point of attachment to the rest of the molecule. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Associated: Two events or entities are "associated" with one another, as that term is used herein, if the presence, level, degree, type and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of, susceptibility to, severity of, stage of, etc. the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, electrostatic, magnetism, and combinations thereof.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" or "bioactive" refers to a characteristic of any agent that has activity in a biological system, and particularly in an organism. For instance, an agent that, when administered to an organism, has a biological or physiological effect on that organism, is considered to be biologically active. In some embodiments, a "bioactive" interacts with a biological system and/or organism. In some embodiments, a "bioactive" interacts with an organism and a surface. In some embodiments, a "bioactive" is sandwiched between a surface (e.g., glass, plastic) and an organism (e.g., cell). In some embodiments, a "bioactive" is permeable to components of a biological system (e.g., cell, macromolecule, steroid, lipophilic molecule, polar molecule). In some embodiments, a "bioactive" interacts with focal adhesions of a cell (e.g., macromolecule assemblies). In some embodiments, a "bioactive" facilitates interaction within a cell microenvironment that consists of other cells and an extracellular matrix. In some embodiments, a "bioactive" regulates cell polarization. In some embodiments, a "bioactive" regulates cell protrusion. In some embodiments, a "bioactive" regulates cell migration.

Biological Sample: As used herein, the term "biological sample" typically refers to a sample obtained or derived from a biological source (e.g., a tissue or organism or cell culture) of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Biomarker: The term "biomarker" is used herein, consistent with its use in the art, to refer to a to an entity, event, or characteristic whose presence, level, degree, type, and/or form, correlates with a particular biological event or state of interest, so that it is considered to be a "marker" of that event or state. To give but a few examples, in some embodiments, a biomarker may be or comprise a marker for a particular disease state, or for likelihood that a particular disease, disorder or condition may develop, occur, or reoccur. In some embodiments, a biomarker may be or comprise a marker for a particular disease or therapeutic outcome, or likelihood thereof. Thus, in some embodiments, a biomarker is predictive, in some embodiments, a biomarker is prognostic, and in some embodiments, a biomarker is diagnostic of the relevant biological event or state of interest. A biomarker may be or comprise an entity of any chemical class, and may be or comprise a combination of entities. For example, in some embodiments, a biomarker may be or comprise a nucleic acid, a polypeptide, a lipid, a carbohydrate, a small molecule, an inorganic agent (e.g., a metal or ion), or a combination thereof. In some embodiments, a biomarker is a cell surface marker. In some embodiments, a biomarker is intracellular. In some embodiments, a biomarker is detected outside of cells (e.g., is secreted or is otherwise generated or present outside of cells, e.g., in a body fluid such as blood, urine, tears, saliva, cerebrospinal fluid, etc. In some embodiments, a biomarker may be or comprise a genetic or epigenetic signature. In some embodiments, a biomarker may be or comprise a gene expression signature.

Bioprinting: The term "bioprinting," as used herein, refers to 3D printing or additive manufacturing with biocompatible materials such as hydrogels onto which live cells may be stably adhered and/or otherwise functionalized.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Conservative and non-conservative substitution: A "conservative" amino acid substitution is one in which one amino acid residue is replaced with another amino acid residue having a similar side chain. Families of amino acid residues having similar side chains have been defined in the art, including basic side chains (e.g., lysine (K), arginine (R), histidine (H)); acidic side chains (e.g., aspartic acid (D), glutamic acid (E)); uncharged polar side chains (e.g., glycine (G); asparagine (N), glutamine (Q), serine (S), threonine (T), tyrosine (Y), cysteine (C)); nonpolar side chains (e.g., alanine (A), valine (V), leucine (L), isoleucine (I), proline (P), phenylalanine (F), menine (M), tryptophan (W), beta-branched side chains (e.g., threonine (T), valine (V), isoleucine (I)); and aromatic side chains (e.g., tyrosine (Y), phenylalanine (F), tryptophan (W), histidine (H)). For example, substitution of a phenylalanine for a tyrosine is a conservative substitution. In some embodiments, conservative amino acid substitutions in the sequence of a ligand confer or improve specific binding of the ligand a target of interest. In some embodiments, conservative amino acid substitutions in the sequences of a ligand do not reduce or abrogate the binding of the ligand to a target of interest. In some embodiments, conservative amino acid substitutions do not significantly affect specific binding of a ligand to a target of interest. Methods of identifying nucleotide and amino acid conservative substitutions and non-conservative substitutions which confer, alter or maintain selective binding affinity are known in the art (see, e.g., Brummell, Biochem. 32:1180-1187 (1993); Kobayashi, Protein Eng. 12(10):879-884 (1999); and Burks, PNAS 94:412-417 (1997)). In some embodiments, non-conservative amino acid substitutions in the sequence of a ligand confer or improve specific binding of the ligand a target of interest. In some embodiments, non-conservative amino acid substitutions in the sequences of a ligand do not reduce or abrogate the binding of the ligand to a target of interest. In some embodiments, non-conservative amino acid substitutions do not significantly affect specific binding of a ligand to a target of interest.

Engineered: In general, the term "engineered" refers to the aspect of having been manipulated by the hand of man. For example, a polynucleotide is considered to be "engineered" when two or more sequences that are not linked together in that order in nature are manipulated by the hand of man to be directly linked to one another in the engineered polynucleotide and/or when a particular residue in a polynucleotide is non-naturally occurring and/or is caused through action of the hand of man to be linked with an entity or moiety with which it is not linked in nature. For example, in some embodiments described and/or utilized herein, an engineered polynucleotide comprises a regulatory sequence that is found in nature in operative association with a first coding sequence but not in operative association with a second coding sequence, is linked by the hand of man so that it is operatively associated with the second coding sequence. Comparably, a polypeptide may be considered to be "engineered" if encoded by or expressed from an engineered polynucleotide, and/or if produced other than natural expression in a cell. Analogously, a cell or organism is considered to be "engineered" if it has been subjected to a manipulation, so that its genetic, epigenetic, and/or phenotypic identity is altered relative to an appropriate reference cell such as otherwise identical cell that has not been so manipulated. In some embodiments, the manipulation is or comprises a genetic manipulation, so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). In some embodiments, an engineered cell is one that has been manipulated so that it contains and/or expresses a particular agent of interest (e.g., a protein, a nucleic acid, and/or a particular form thereof) in an altered amount and/or according to altered timing relative to such an appropriate reference cell. As is common practice and is understood by those in the art, progeny of an engineered polynucleotide or cell are typically still referred to as "engineered" even though the actual manipulation was performed on a prior entity.

"Improve," "increase", "inhibit" or "reduce": As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single individual) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Interstitial space: As used herein, the term "interstitial space" refers to a void wherein a cell in a fluid(s) and/or a polymer (e.g., a hydrogel) are seeded to create a tissue.

Interstitial infill: As used herein, the term "interstitial infill" refers to a polymer anchor and/or structure (e.g., hydrogel) that enables creation of a two-dimensional or three-dimensional tissue through stimulation of cell association.

In vitro: The term "in vitro" as used herein refers to events that occur in an artificial environment, e.g., in a test tube or reaction vessel, in cell culture, etc., rather than within a multi-cellular organism.

In vivo: as used herein refers to events that occur within a multi-cellular organism, such as a human and a non-human animal. In the context of cell-based systems, the term may be used to refer to events that occur within a living cell (as opposed to, for example, in vitro systems).

Linker: as used herein, is used to refer to that portion of a multi-element agent that connects different elements to one another.

Operably linked: The term "operably linked," as used herein, indicates that two or more components are arranged such that the components function normally and allow the possibility that at least one of the components can mediate a function that is exerted upon at least one of the other components. Two molecules are "operably linked" whether they are attached directly or indirectly.

Optionally Substituted: As described herein, compounds may sometimes contain "optionally substituted" moieties. In general, the term "substituted," whether preceded by the term "optionally" or not, means that one or more hydrogens of the designated moiety are replaced with a suitable substituent. "Substituted" applies to one or more hydrogens that are either explicit or implicit from the structure (e.g.,

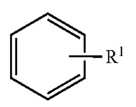

refers to at least

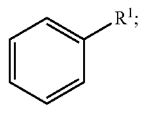

; and

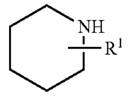

refers to at least

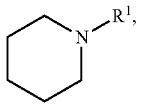

,

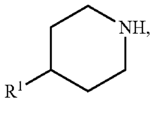

,

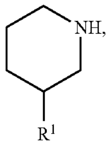

, or

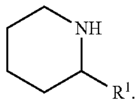

.

Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. Suitable monovalent substituents on a substitutable carbon atom of an "optionally substituted" group are independently halogen; $—(CH_2)_{0-4}R^{\circ}$; $—(CH_2)_{0-4}OR^{\circ}$; $—O(CH_2)_{0-4}R^{\circ}$, $—O—(CH_2)_{0-4}C(O)OR^{\circ}$; $—(CH_2)_{0-4}CH(OR^{\circ})_2$; $—(CH_2)_{0-4}SR^{\circ}$; $—(CH_2)_{0-4}Ph$, which may be substituted with $R^{\circ}$; $—(CH_2)_{0-4}O(CH_2)_{0-1}Ph$ which may be substituted with $R^{\circ}$; $—CH{=}CHPh$, which may be substituted with $R^{\circ}$; $—(CH_2)_{0-4}O(CH_2)_{0-1}$-pyridyl which may be substituted with $R^{\circ}$; $—NO_2$; —CN; $—N_3$; $—(CH_2)_{0-4}N(R^{\circ})_2$; $—(CH_2)_{0-4}N(R^{\circ})C(O)R^{\circ}$; $—N(R^{\circ})C(S)R^{\circ}$; $—(CH_2)_{0-4}N(R^{\circ})C(O)NR^{\circ}_2$; $—N(R^{\circ})C(S)NR^{\circ}_2$; $—(CH_2)_{0-4}N(R^{\circ})C(O)OR^{\circ}$; $—N(R^{\circ})N(R^{\circ})C(O)R^{\circ}$; $—N(R^{\circ})N(R^{\circ})C(O)NR^{\circ}_2$; $—N(R^{\circ})N(R^{\circ})C(O)OR^{\circ}$; $—(CH_2)_{0-4}C(O)R^{\circ}$; $—(CH_2)_{0-4}C(O)CH_2R^{\circ}$; $—C(S)R^{\circ}$; $—(CH_2)_{0-4}C(O)OR^{\circ}$; $—(CH_2)_{0-4}C(O)SR^{\circ}$; $—(CH_2)_{0-4}C(O)OSiR^{\circ}_3$; $—(CH_2)_{0-4}OC(O)R^{\circ}$; $—OC(O)(CH_2)_{0-4}SR—$, $SC(S)SR^{\circ}$; $—(CH_2)_{0-4}SC(O)R^{\circ}$; $—(CH_2)_{0-4}C(O)NR^{\circ}_2$; $—C(S)NR^{\circ}_2$; $—C(S)SR^{\circ}$; $—SC(S)SR^{\circ}$, $—(CH_2)_{0-4}OC(O)NR^{\circ}_2$; $—C(O)N(OR^{\circ})R^{\circ}$; $—C(O)C(O)R^{\circ}$; $—C(O)CH_2C(O)R^{\circ}$; $—C(NOR^{\circ})R^{\circ}$; $—(CH_2)_{0-4}SSR^{\circ}$; $—(CH_2)_{0-4}S(O)_2R^{\circ}$; $—(CH_2)_{0-4}S(O)_2OR^{\circ}$; $—(CH_2)_{0-4}OS(O)_2R^{\circ}$; $—S(O)_2NR^{\circ}_2$; $—(CH_2)_{0-4}S(O)R^{\circ}$; $—N(R^{\circ})S(O)_2NR^{\circ}_2$; $—N(R^{\circ})S(O)_2R^{\circ}$; $—N(OR^{\circ})R^{\circ}$; $—C(NH)NR^{\circ}_2$; $—P(O)_2R^{\circ}$; $—P(O)R^{\circ}_2$; $—OP(O)R^{\circ}_2$; $—OP(O)(OR^{\circ})_2$; $SiR^{\circ}_3$; $—(C_{1-4}$ straight or branched alkylene$)O—N(R^{\circ})_2$; or $—(C_{1-4}$ straight or branched alkylene$)C(O)O—N(R^{\circ})_2$, wherein each $R^{\circ}$ may be substituted as defined below and is independently hydrogen, $C_{1-6}$ aliphatic, $—CH_2Ph$, $—O(CH_2)_{0-1}Ph$, $—CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below. Suitable monovalent substituents on R° (or the ring formed by taking two independent occurrences of R° together with their intervening atoms), are independently halogen, $—(CH_2)_{0-2}R^{●}$, -(haloR●), $—(CH_2)_{0-2}OH$, $—(CH_2)_{0-2}OR^{●}$, $—(CH_2)_{0-2}CH(OR^{●})_2$; —O(haloR●), —CN, $—N_3$, $—(CH_2)_{0-2}C(O)R^{●}$, $—(CH_2)_{0-2}C(O)OH$, $—(CH_2)_{0-2}C(O)OR^{●}$, $—(CH_2)_{0-2}SR^{●}$, $—(CH_2)_{0-2}SH$, $—(CH_2)_{0-2}NH_2$, $—(CH_2)_{0-2}NHR^{●}$, $—(CH_2)_{0-2}NR^{●}_2$, $—NO_2$, $—SiR^{●}_3$, $—OSiR^{●}_3$, $—C(O)SR^{●}$, $—(C_{1-4}$ straight or branched alkylene)C(O)OR●, or —SSR● wherein each R● is unsubstituted or where preceded by "halo" is substituted only with one or more halogens, and is independently selected from $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include ═O and ═S. Suitable divalent substituents on a saturated carbon atom of an "optionally substituted" group include the following: ═O ("oxo"), ═S, $═NNR^*_2$, ═NNHC(O)R*, ═NNHC(O)OR*, $═NNHS(O)_2R^*$, ═NR*, ═NOR*, $—O(C(R^*_2))_{2-3}O—$, or $—S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $—O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable substituents on the aliphatic group of R* include halogen, —R●, -(haloR●), —OH, —OR●, —O(haloR●), —CN, —C(O)OH, —C(O)OR●, $—NH_2$, —NHR●, $—NR^{●}_2$, or $—NO_2$, wherein each R● is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur. Suitable substituents on a substitutable nitrogen of an "optionally substituted" group include $—R^†$, $—NR^†_2$, $—C(O)R^†$, $—C(O)CH_2R^†$, $—C(O)OR^†$, $—C(O)C(O)R^†$, $—C(O)CH_2C(O)R^†$, $—S(O)_2R^†$, $—S(O)_2NR^†_2$, $—C(S)NR^†_2$, $—C(NH)NR^†_2$, or $—N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur. Suitable substituents on the aliphatic group of $R^†$ are independently halogen, —R●, -(haloR●), —OH, —OR●, —O(haloR●), —CN, —C(O)OH, —C(O)OR●, $—NH_2$, —NHR●, $—NR^{●}_2$, or $—NO_2$, wherein each R● is unsubstituted or where preceded by "halo" is substituted only with one or more halogens, and is independently $C_{1-4}$ aliphatic, $—CH_2Ph$, $—O(CH_2)_{0-1}Ph$, or a 5-6-membered saturated, partially unsaturated, or aryl ring having 0-4 heteroatoms independently selected from nitrogen, oxygen, or sulfur.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Patient: As used herein, the term "patient" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the patient is receiving or has received certain therapy to diagnose and/or to treat a disease, disorder, or condition.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Physiological conditions: as used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

Polypeptide: The term "polypeptide" as used herein refers to a sequential chain of amino acids linked together via peptide bonds. The term is used to refer to an amino acid chain of any length, but one of ordinary skill in the art will understand that the term is not limited to lengthy chains and can refer to a minimal chain comprising two amino acids linked together via a peptide bond. As is known to those skilled in the art, polypeptides may be processed and/or modified.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" refers to the multiple polypeptides that are physically coupled and function together as the discrete unit.

Prodrug: As used herein, the term "prodrug" refers to a compound that is a drug precursor which, following administration, releases (e.g., is converted into) the drug in vivo via a chemical or physiological process (e.g., via cleavage as a result of exposure to a particular pH or through action of a particular enzyme or enzymes).

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Small molecule: As used herein, the term "small molecule" means a low molecular weight organic and/or inorganic compound. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not and/or does not comprise a protein or polypeptide (e.g., is not an oligopeptide or peptide). In some embodiments, a small molecule is not and/or does not comprise a polynucleotide (e.g., is not an oligonucleotide). In some embodiments, a small molecule is not and/or does not comprise a polysaccharide; for example, in some embodiments, a small molecule is not a glycoprotein, proteoglycan, glycolipid, etc.). In some embodiments, a small molecule is not a lipid. In some embodiments, a small molecule is a modulating agent (e.g., is an inhibiting/inhibitory agent or an activating agent). In some embodiments, a small molecule is biologically active. In some embodiments, a small molecule is detectable (e.g., comprises at least one detectable moiety). In some embodiments, a small molecule is a therapeutic agent. Those of ordinary skill in the art, reading the present disclosure, will appreciate that certain small molecule compounds described herein may be provided and/or utilized in any of a variety of forms such as, for example, crystal forms, salt forms, protected forms, pro-drug forms, ester forms, isomeric forms (e.g., optical and/or structural isomers), isotopic forms, etc. Those of skill in the art will appreciate that certain small molecule compounds have structures that can exist in one or more stereoisomeric forms. In some embodiments, such a small molecule may be utilized in accordance with the present disclosure in the form of an individual enantiomer, diastereomer or geometric isomer, or may be in the form of a mixture of stereoisomers; in some embodiments, such a small molecule may be utilized in accordance with the present disclosure in a racemic mixture form. Those of skill in the art will appreciate that certain small molecule compounds have structures that can exist in one or more tautomeric forms. In some embodiments, such a small molecule may be utilized in accordance with the present disclosure in the form of an individual tautomer, or in a form that interconverts between tautomeric forms. Those of skill in the art will appreciate that certain small molecule compounds have structures that permit isotopic substitution (e.g., $^{2}H$ or $^{3}H$ for H; $^{11}C$, $^{13}C$ or $^{14}C$ for $^{12}C$; $^{13}N$ or $^{15}N$ for $^{14}N$; $^{17}O$ or $^{18}O$ for $^{16}O$; $^{36}Cl$ for XXC; $^{18}F$ for XXF; 131I for XXXI; etc.). In some embodiments, such a small molecule may be utilized in accordance with the present disclosure in one or more isotopically modified forms, or mixtures thereof. In some embodiments, reference to a particular small molecule compound may relate to a specific form of that compound. In some embodiments, a particular small molecule compound may be provided and/or utilized in a salt form (e.g., in an acid-addition or base-addition salt form, depending on the compound); in some such embodiments, the salt form may be a pharmaceutically acceptable salt form. In some embodiments, where a small molecule compound is one that exists or is found in nature, that compound may be provided and/or utilized in accordance in the present disclosure in a form different from that in which it exists or is found in nature. Those of ordinary skill in the art will appreciate that, in some embodiments, a preparation of a particular small molecule compound that contains an absolute or relative amount of the compound, or of a particular form thereof, that is different from the absolute or relative (with respect to another component of the preparation including, for example, another form of the compound) amount of the compound or form that is present in a reference preparation of interest (e.g., in a primary sample from a source of interest such as a biological or environmental source) is distinct from the compound as it exists in the reference preparation or source. Thus, in some embodiments, for example, a preparation of a single stereoisomer of a small molecule compound may be considered to be a different form of the compound than a racemic mixture of the compound; a particular salt of a small molecule compound may be considered to be a different form from another salt form of the compound; a preparation that contains only a form of the compound that contains one conformational isomer ((Z) or (E)) of a double bond may be considered to be a different form of the compound from one that contains the other conformational isomer ((E) or (Z)) of the double bond; a preparation in which one or more atoms is a different isotope than is present in a reference preparation may be considered to be a different form; etc.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Systemic: The phrases "systemic administration," "administered systemically," "peripheral administration," and "administered peripherally" as used herein have their art-understood meaning referring to administration of a compound and/or composition such that it enters the ecosystem.

Variant and Mutant: The term "variant" is usually defined in the scientific literature and used herein in reference to an organism that differs genetically in some way from an accepted standard, "Variant" can also be used to describe phenotypic differences that are not genetic (King and Stansfield, 2002, A dictionary of genetics, 6th ed., New York, New York, Oxford University Press.

The term "mutation" is defined by most dictionaries and used herein in reference to the process that introduces a heritable change into the structure of a gene (King & Stansfield, 2002) thereby producing a "mutant." The term "variant" is increasingly being used in place of the term "mutation" in scientific and non-scientific literature. The terms are used interchangeably herein.

"Vasculature" or "Vascularized" or "Vascular": As used herein, the terms "vasculature", "vascularized", and "vascular" refer to a single vessel or a network (i.e., a two-dimensional network, a three-dimensional network) of vessels that enable distribution of drugs, biologics, biological fluids, and/or other substances to a cell.

"Ecosystem"

Among other things the present disclosure describes an ecosystem for designing, building, and refining physical models or platforms that replicate the functioning of organs (for example, human organs) that may be used to for drug discovery and for assessing the effectiveness of various therapies. FIG. 1 illustrates an ecosystem 10 for creating organ-on-a-chip and other biological models, according to aspects of the present embodiments. The ecosystem 10 may include bioprinting equipment (for example, 3D printers that print using biological materials, bio-inks, etc.), conventional (non-bio) 3D printers (for example, that print using polymers, metals, ceramics, etc.), post-processing equipment such as heat treat ovens, autoclaves, rinse stations, cell seeding equipment (such as pipettes for seeding live cells in bioprinted scaffolds), cell culture equipment such as bioreactors, drug perfusion equipment (including pumps, filtration equipment, flow channels, valves), assaying equipment for performing assays on perfused cells, live imaging equipment, sensors and/or kits for quantification of analytes, image processing equipment (such as computers including memory and processors), machine learning capabilities (including cloud/network-based machine learning algorithms, local algorithms, CPU, GPU, and/or tensor processing unit (TPU)-based algorithms, etc.), and computer equipment and software for designing and refining computer models to be printed as physical models, etc. The ecosystem 10 may also include equipment for glass room, clean rooms for cell incubation, shaker plates used in post-processing of printed components, refrigerators for storing bio-inks, PCR (polymerase chain reaction) equipment for amplifying cells, next generation sequencing equipment, flow cytometry equipment, analytical equipment, diagnostic tooling, microscopy equipment, incubators, and other equipment. In some embodiments, bioprinting methodologies, systems, and technologies described herein may be overlapping with, similar to, substantially similar to, and/or identical to those described in U.S. Pat. Nos. 10,639,880 and/or 10,828,833.

Scaffold

Polymer Composition

The present disclosure provides technologies that utilize a polymer moiety (and/or materials, such as bioprinted entities, generated from them, and/or ecosystems that include them), for example to model an organ system (e.g., a diseased or healthy organ), including in diagnostic applications (e.g., to identify and validate a new disease target). In some aspects, the present disclosure provides methods to generate an ecosystem, including a polymer (e.g., a hydrogel), that includes control of environmental factors used for assaying synthetic tissue and/or organ models, real-time and/or continuous tracking of biomarkers via sensors, an ability to rapidly image tissues and/or cells, processing of assay data, machine learning tools for diagnosing results, and updating of scaffold print files such that updated models can be reprinted, assays may be rerun, and the results may be reanalyzed.

The present disclosure teaches that, in some embodiments, a bioprinted entity provided and/or utilized in accordance with the present disclosure includes a polymer moiety, such as a hydrogel moiety (e.g., PEGDA) and a coating moiety (e.g., a polypeptide), covalently linked to one another, optionally via a linker.

Indeed, in some aspects, the present disclosure provides improvements to useful polymers achieved by conjugating them to a coating moiety (e.g., a polypeptide) as described herein to facilitate association of a cell with the bioprinted entity. In some embodiments, the present disclosure provides conjugates of a polymer moiety that show improved cellular distribution relative to a comparable preparation of the same polymer moiety when not so conjugated. Those skilled in the art, reading the present disclosure, will appreciate that conjugates as provided and/or utilized herein are typically produced by linking a coating moiety (e.g., a polypeptide) as described herein with a preparation of a polymer moiety. Those skilled in the art will further appreciate that such polymer moiety preparations are typically not perfectly uniform compositions but rather include some structural diversity of the polymers within them. Those skilled in the art will appreciate that polymer preparations (including, e.g., as may be purchased commercially or prepared) are typically characterized by a molecular weight, or molecular weight range, which is typically representative of an average or median molecular weight of polymer in the preparation.

Still further, those skilled in the art will appreciate that polymer moieties are typically characterized by a polydispersity index, reflecting the weight average divided by the number average molecular weight (Mw/Mn), which provides an assessment of the molecular weight distribution in a polymer moiety.

In some embodiments, conjugates as described and/or utilized herein are prepared from polymer moiety with a PDI within a range of about 1 to about 5. In some embodiments, conjugates as described above and/or utilized herein are prepared from polymer moieties with a PDI of about 1 to about 3. In some embodiments, conjugates as described above and/or utilized herein are prepared from polymer moieties with a PDI of about 3 to about 5. In some embodiments, conjugates as described and/or utilized herein are prepared from a polymer moiety with a PDI of about 1 to about 2.

In some embodiments, a polymer moiety may be characterized by an optimal diffusion coefficient, reflecting the diffusivity of a solute with hydrodynamic radius in a liquid, wherein it provides an assessment of the rate of diffusion of one material through another. In some embodiments, a polymer moiety as described and/or utilized herein may have a diffusion coefficient of about 5 $\mu m^2/sec$ to about 120 $\mu m^2/sec$.

The present disclosure particularly teaches that provided technologies are particularly applicable to (e.g., beneficial when applied to) polymer moieties that are acrylated hydrogel moieties, such as PEGDA.

In some embodiments, the present disclosure provides an insight that certain polymer moieties surprisingly can impart to a conjugate as described herein an ability to exhibit a desired cell distribution.

In some embodiments, the present disclosure provides an insight that certain bioprinted entities exhibit a desired cell distribution.

In those embodiments that may comprise a plurality of polymer moieties, such polymer moieties may, in some embodiments all be the same; in other embodiments, a provided system may comprise a plurality of distinct polymer moieties.

For example, in some embodiments, a polymer moiety useful in accordance with the present disclosure is characterized by a particular degree of interaction with a cell, for example, when associated (e.g., linked) with a particular coating moiety (e.g., a polypeptide).

In some embodiments, a bioprinted entity may be or comprise an optionally substituted polymer moiety. In some embodiments, a polymer moiety is optionally substituted with $-(CH_2)_{0-4}C(O)CH_2R^\circ$. In some embodiments, a polymer moiety is optionally substituted with $-C(O)CH_2R^\circ$. In some embodiments, a polymer moiety is optionally substituted with $-C(O)CH_2R^\circ$, wherein $R^\circ$ is $C_{1-6}$ aliphatic. In some such embodiments, $R^\circ$ is an unsaturated $C_{1-6}$ alkyl. In further embodiments, $R^\circ$ is $CH_2$.

In some embodiments, a polymer moiety is optionally substituted with $-C(O)CH_2R^\dagger$.

In some embodiments, a polymer moiety is optionally substituted with $-C(O)CH_2R^\dagger$, wherein $R^\dagger$ is $C_{1-6}$ aliphatic. In some such embodiments, $R^\dagger$ is an unsaturated $C_{1-6}$ alkyl. In further embodiments, $R^\dagger$ is $CH_2$.

In some embodiments, a polymer moiety is optionally substituted with at least one

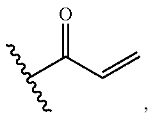 [SMILES: *C(=O)C=C]

, wherein “ ” represents a point of attachment to the polymer moiety.

In some embodiments, a polymer moiety is optionally substituted with at least one

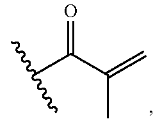 [SMILES: *C(=O)C(=C)C]

wherein "" represents a point of attachment to the polymer moiety.

In some embodiments, a polymer moiety is optionally substituted with at least one

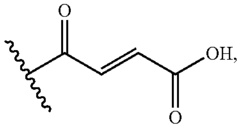 [SMILES: *C(=O)/C=C/C(=O)O]

wherein "" represents a point of attachment to the polymer moiety.

In some embodiments, a polymer moiety may be an acrylated, methacrylated, or diacrylated hydrogel.

In some embodiments, a bioprinted entity may be or comprise a polymer moiety selected from the group comprising PEGDA, alginate, gelatin, GelMA, ColMA, hyaluronic acid, and/or PEG.

Coating Moieties

In some embodiments, the present disclosure provides and/or utilizes conjugates (and/or materials, such as hydrogels, generated from them, and/or systems that include them) which comprise one or more polymer and coating moieties (e.g., a polypeptide), optionally associated with one another via a linker(s).

In some embodiments, the present disclosure provides and/or utilizes conjugates (and/or materials, such as hydrogels, generated from them, and/or systems that include them) which comprise one or more polymer and coating moieties, optionally associated with one another via a linker(s), wherein the coating moiety is selected from a group consisting of a polypeptide, a small molecule, a peptidomimetic, a lipid, a lipid nanoparticle, a nucleic acid, a (poly)saccharide, or a combination thereof.

In some embodiments, the present disclosure provides and/or utilizes conjugates (and/or materials, such as hydrogels, generated from them, and/or systems that include them) which comprise one or more polymer and coating moieties, optionally associated with one another via a linker(s), wherein the coating moiety is a polypeptide.

In some embodiments, the present disclosure provides an insight that certain polypeptides surprisingly can impart to a conjugate as described herein an ability to exhibit a desired cell distribution.

In those embodiments that may comprise a plurality of polypeptides, such polypeptides may, in some embodiments all be the same; in other embodiments, a provided system may comprise a plurality of distinct polypeptides.

For example, in some embodiments, a polypeptide useful in accordance with the present disclosure is characterized by a particular degree of interaction with a cell, for example, when associated (e.g., linked) with a particular polymer moiety.

Those skilled in the art, reading the present disclosure, will appreciate that, in some embodiments, interaction of a cell with a bioprinted entity comprising a particular polymer moiety may be adjusted, for example through linkage of a plurality of polypeptides, which may be the same or different and which, individually or together, may be considered or constitute a bioprinted entity as described herein.

In some embodiments, a polypeptide as described herein may, for example, be selected from the group consisting of a collagen, a fibrin, an integrin, a selectin, a cadherin, a member of the immunoglobulin superfamily (IgSF) (e.g., a nectin, a mucin), a laminin, Matrigel, an extracellular matrix (ECM) protein, an antibody, an antibody fragment, etc. In some embodiments, a polypeptide is a collagen. In some embodiments, a polypeptide is a fibrin. In some embodiments, a polypeptide is an integrin. In some embodiments, a polypeptide is a selectin. In some embodiments, a polypeptide is a cadherin. In some embodiments, a polypeptide is an IgSF. In some embodiments, a polypeptide is a nectin. In some embodiments, a polypeptide is a fibronectin. In some embodiments, a polypeptide is a mucin. In some embodiments, a polypeptide is a laminin. In some embodiments, a polypeptide is a Matrigel. In some embodiments, a polypeptide is an ECM protein. In some embodiments, a polypeptide is an antibody. In some embodiments, a polypeptide is an antibody fragment.

In some embodiments, a polypeptide as described above and herein may be naturally occurring. In some embodiments, a polypeptide as described above and herein may be engineered. In some such embodiments, an engineered polypeptide may have one or more conservative amino acid substitutions. In some such embodiments, an engineered polypeptide may have one or more non-conservative amino acid substitutions. In further embodiments, an engineered polypeptide may have a combination of one or more conservative and/or non-conservative amino acid substitutions.

In some embodiments, the present disclosure provides and/or utilizes conjugates (and/or materials, such as hydrogels, generated from them, and/or systems that include them) which comprise one or more polymer and coating moieties, optionally associated with one another via a linker(s), wherein the coating moiety is a small molecule.

In some embodiments, the present disclosure provides an insight that certain small molecules surprisingly can impart to a conjugate as described herein an ability to exhibit a desired cell distribution.

In those embodiments that may comprise a plurality of small molecules, such small molecules may, in some embodiments all be the same; in other embodiments, a provided system may comprise a plurality of distinct small molecules.

For example, in some embodiments, a small molecule useful in accordance with the present disclosure is characterized by a particular degree of interaction with a cell, for example, when associated (e.g., linked) with a particular polymer moiety.

Those skilled in the art, reading the present disclosure, will appreciate that, in some embodiments, interaction of a cell with a bioprinted entity comprising a particular polymer moiety may be adjusted, for example through linkage of a plurality of small molecules, which may be the same or different and which, individually or together, may be considered or constitute a bioprinted entity as described herein.

In some embodiments, the present disclosure provides and/or utilizes conjugates (and/or materials, such as hydrogels, generated from them, and/or systems that include them) which comprise one or more polymer and coating moieties, optionally associated with one another via a linker (s), wherein the coating moiety is a peptidomimetic.

In some embodiments, the present disclosure provides an insight that certain peptidomimetics surprisingly can impart to a conjugate as described herein an ability to exhibit a desired cell distribution.

In those embodiments that may comprise a plurality of peptidomimetics, such peptidomimetics may, in some embodiments all be the same; in other embodiments, a provided system may comprise a plurality of distinct peptidomimetics.

For example, in some embodiments, a peptidomimetic useful in accordance with the present disclosure is characterized by a particular degree of interaction with a cell, for example, when associated (e.g., linked) with a particular peptidomimetic moiety.

Those skilled in the art, reading the present disclosure, will appreciate that, in some embodiments, interaction of a cell with a bioprinted entity comprising a particular peptidomimetic moiety may be adjusted, for example through linkage of a plurality of peptidomimetics, which may be the same or different and which, individually or together, may be considered or constitute a bioprinted entity as described herein.

In some embodiments, the present disclosure provides and/or utilizes conjugates (and/or materials, such as hydrogels, generated from them, and/or systems that include them) which comprise one or more polymer and coating moieties, optionally associated with one another via a linker(s), wherein the coating moiety is a lipid.

In some embodiments, the present disclosure provides an insight that certain lipids surprisingly can impart to a conjugate as described herein an ability to exhibit a desired cell distribution.

In those embodiments that may comprise a plurality of lipids, such lipids may, in some embodiments all be the same; in other embodiments, a provided system may comprise a plurality of distinct lipids.

For example, in some embodiments, a lipid useful in accordance with the present disclosure is characterized by a particular degree of interaction with a cell, for example, when associated (e.g., linked) with a particular polymer moiety.

Those skilled in the art, reading the present disclosure, will appreciate that, in some embodiments, interaction of a cell with a bioprinted entity comprising a particular polymer moiety may be adjusted, for example through linkage of a plurality of lipids, which may be the same or different and which, individually or together, may be considered or constitute a bioprinted entity as described herein.

In some embodiments, the present disclosure provides and/or utilizes conjugates (and/or materials, such as hydrogels, generated from them, and/or systems that include them) which comprise one or more polymer and coating moieties, optionally associated with one another via a linker(s), wherein the coating moiety is a lipid nanoparticle.

In some embodiments, the present disclosure provides an insight that certain lipid nanoparticles surprisingly can impart to a conjugate as described herein an ability to exhibit a desired cell distribution.

In those embodiments that may comprise a plurality of lipid nanoparticles, such lipid nanoparticles may, in some embodiments all be the same; in other embodiments, a provided system may comprise a plurality of distinct lipid nanoparticles.

For example, in some embodiments, a lipid nanoparticle useful in accordance with the present disclosure is characterized by a particular degree of interaction with a cell, for example, when associated (e.g., linked) with a particular polymer moiety.

Those skilled in the art, reading the present disclosure, will appreciate that, in some embodiments, interaction of a cell with a bioprinted entity comprising a particular polymer moiety may be adjusted, for example through linkage of a plurality of lipid nanoparticles, which may be the same or different and which, individually or together, may be considered or constitute a bioprinted entity as described herein.

In some embodiments, a lipid nanoparticle as described above and herein may comprise a payload. In some embodiments, the payload comprises a naturally occurring and/or engineered nucleic acid. In some such embodiments, an engineered nucleic acid may have one or more conservative substitutions. In some such embodiments, an engineered nucleic acid may have one or more non-conservative substitutions. In further embodiments, an engineered nucleic acid may have a combination of one or more conservative and/or non-conservative substitutions. In some embodiments, the nucleic acid may be selected from a group consisting of DNA, siRNA, mRNA, tRNA, rRNA, etc. In some embodiments, the nucleic acid is DNA. In some embodiments, the nucleic acid is siRNA. In some embodiments, the nucleic acid is mRNA. In some embodiments, the nucleic acid is tRNA. In some embodiments, the nucleic acid is rRNA.

In some embodiments, the present disclosure provides and/or utilizes conjugates (and/or materials, such as hydrogels, generated from them, and/or systems that include them) which comprise one or more polymer and coating moieties, optionally associated with one another via a linker(s), wherein the coating moiety is a nucleic acid (e.g., DNA, siRNA, mRNA, tRNA, rRNA).

In some embodiments, the present disclosure provides an insight that certain nucleic acids surprisingly can impart to a conjugate as described herein an ability to exhibit a desired cell distribution.

In those embodiments that may comprise a plurality of nucleic acids, such nucleic acids may, in some embodiments all be the same; in other embodiments, a provided system may comprise a plurality of distinct nucleic acids.

For example, in some embodiments, a nucleic acid useful in accordance with the present disclosure is characterized by a particular degree of interaction with a cell, for example, when associated (e.g., linked) with a particular polymer moiety.

Those skilled in the art, reading the present disclosure, will appreciate that, in some embodiments, interaction of a cell with a bioprinted entity comprising a particular polymer moiety may be adjusted, for example through linkage of a plurality of nucleic acids, which may be the same or different and which, individually or together, may be considered or constitute a bioprinted entity as described herein.

In some embodiments, a coating moiety comprises a naturally occurring and/or engineered nucleic acid. In some such embodiments, an engineered nucleic acid may have one or more conservative substitutions. In some such embodiments, an engineered nucleic acid may have one or more non-conservative substitutions. In further embodiments, an engineered nucleic acid may have a combination of one or more conservative and/or non-conservative substitutions. In some embodiments, the nucleic acid may be selected from a group consisting of DNA, siRNA, mRNA, tRNA, rRNA, etc. In some embodiments, the nucleic acid is DNA. In some embodiments, the nucleic acid is siRNA. In some embodiments, the nucleic acid is mRNA. In some embodiments, the nucleic acid is tRNA. In some embodiments, the nucleic acid is rRNA.

In some embodiments, the present disclosure provides and/or utilizes conjugates (and/or materials, such as hydrogels, generated from them, and/or systems that include them) which comprise one or more polymer and coating moieties, optionally associated with one another via one or more linker(s), wherein the coating moiety is a (poly) saccharide.

In some embodiments, the present disclosure provides an insight that certain (poly)saccharides surprisingly can impart to a conjugate as described herein an ability to exhibit a desired cell distribution.

In those embodiments that may comprise a plurality of (poly)saccharides, such (poly)saccharides may, in some embodiments all be the same; in other embodiments, a provided system may comprise a plurality of distinct (poly) saccharides.

For example, in some embodiments, a (poly)saccharide useful in accordance with the present disclosure is characterized by a particular degree of interaction with a cell, for example, when associated (e.g., linked) with a particular polymer moiety.

Those skilled in the art, reading the present disclosure, will appreciate that, in some embodiments, interaction of a cell with a bioprinted entity comprising a particular polymer moiety may be adjusted, for example through linkage of a plurality of (poly)saccharides, which may be the same or different and which, individually or together, may be considered or constitute a bioprinted entity as described herein.

Linkers

In some embodiments, a conjugate, as described in the present disclosure, comprises one or more linkers.

For example, in some embodiments, a conjugate includes a linker which conjugates a polymer moiety and a coating moiety (e.g., a polypeptide).

In some embodiments, a linker moiety is referred to as "L". In some embodiments, a linker may be cleavable or degradable under biological conditions. In some embodiments, a linker may be non-cleavable and/or non-degradable under biological conditions. In some embodiments, a linker may degrade via hydrolysis or enzymatic reaction. In some embodiments, a linker may be cleavable through application of a cleavage promoter (e.g., an electrical, chemical, and/or enzymatic stimulus). In some embodiments, a linker degrades (e.g., over and/or within a specified period of time, such as within hours, days, weeks, or months) after administration of the system.

In some embodiments, a linker may be associated with a moiety as described herein (e.g., with a polymer moiety, a polypeptide, and/or an "other" moiety) via chemical conjugation; in some embodiments chemical conjugation may be or comprise click chemistry. Thus, in some embodiments, a conjugate as described and/or utilized herein may be formed by and/or may participate in a chemical linkage reaction, e.g., a click chemistry reaction.

In some embodiments, conjugation of two or more moieties with one another can be mediated by a chemical reaction that involves amine-reactive click chemistry. In some embodiments, conjugation of two or more moieties with one another can be mediated by a chemical reaction that involves an N-hydroxysuccinimide (NHS). In some embodiments, conjugation of two or more moieties with one another can be mediated by an NHS-ester click chemistry reaction. In some embodiments, conjugation of two or more moieties with one another can be mediated by an NHS-ester click chemistry reaction at physiological conditions.

In some embodiments, a linker is

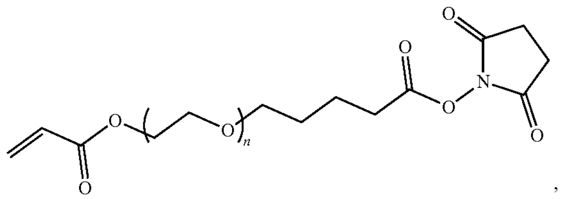

, wherein n is 0-100;

wherein the NHS-ester portion of the linker forms a covalent bond with a free amine on a coating moiety; and wherein the acrylate portion of the linker forms a covalent bond with a polymer moiety.

In some embodiments, a linker is acrylated polyethylene glycol succinimidyl valerate (acrylated PEG SVA).

In some embodiments, a linker is PEG-NHS.

In some embodiments, a linker may be a bond.

In some embodiments, L is polyethylene glycol (PEG). In some embodiments, L may be an ethylene diamine, e.g., a polyethylene glycol diamine, etc.

In some embodiments, L comprises a moiety which results from a "click" reaction. In some embodiments, L comprises a triazole. In some embodiments, L comprises an imine. In some embodiments, L comprises an oxime. In some embodiments, L comprises a hydrazine. In some embodiments, L comprises a moiety which results from a nucleophilic addition. In some embodiments, L comprises a moiety which results from a Michael addition. In some embodiments, L comprises a thiol-ene.

In some embodiments, L is an optionally substituted $C_{1-6}$ alkylene chain wherein one, two, or three methylene units of L are optionally and independently replaced by —NH—, —O—, —S—, —S(O)—, —$S(O)_2$—, or —C(O)—. A variety of techniques may be used for conjugating or associating the polymer moiety to a coating moiety (e.g., a polypeptide).

Cells

The present disclosure teaches that, in some embodiments, a bioprinted entity provided and/or utilized in accordance with the present disclosure includes a polymer moiety, such as a hydrogel moiety (e.g., PEGDA) a coating moiety (e.g., a polypeptide), covalently linked to one another, optionally via a linker (e.g., acrylated PEG SVA), wherein the coating moiety facilitates the association of a cell.

In some embodiments, a cell associated with the bioprinted entity may be selected from a naturally occurring cell and/or an engineered cell. In some embodiments, a cell associated with the bioprinted entity may be a naturally occurring cell. In some embodiments a cell associated with the bioprinted entity may be an engineered cell. In some embodiments, one or more cells associated with the bioprinted entity may be a combination of a naturally occurring and an engineered cell.

In some embodiments, a cell associated with the bioprinted entity and/or seeded therein is selected from a group consisting of an endothelial cell, a biliary endothelial cell, a cholangiocyte, a liver parenchymal cell, a hepatocyte (HC), a primary human hepatocyte (PHH), a hepatic stellate cell (HSCs), a Kupffer cell (KC), a liver sinusoidal endothelial cell (LSEC), a mucous cell, a parietal cell, a chief cell, an endocrine cell (e.g., a G cell, a D cell, a enterochromaffin cell, a EC-like cell, a X/A cell), a columnar epithelial cell, a cardiac fibroblast (CF), a cardiomyocyte, a smooth muscle cell, an enterocyte, a goblet cell, a Paneth cell, a stem cell, a neuron, a glia, a keratinocyte, a melanocyte, a Merkel cell, a Langerhans cell, a germ cell, a stromal cell, a seminiferous tubule, a Leydig cell, a tubule epithelial cell, a macula densa cell, a glomerular endothelial cell, a podocyte, a mesangial cell, a parietal epithelial cell, an immortalized cell (e.g. a 3T3 cell, a A549 cell, a HeLa cell, a HEK 293 cell, a HEK 293T cell, a Huh7 cell, a Jurkat cell, a OK cell, a Ptk2 cell, a Vero cell), a patient-derived cell (e.g., a tumor cell), a T cell, a peripheral blood mononuclear cell (PBMC), and/or an induced pluripotent stem cell (iPSC).

In some embodiments, a cell associated with the bio-printed entity is an endothelial cell.

In some embodiments, a cell associated with the bio-printed entity is a biliary endothelial cell.

In some embodiments, a cell associated with the bio-printed entity is a cholangiocyte.

In some embodiments, a cell associated with the bio-printed entity is a liver parenchymal cell.

In some embodiments, a cell associated with the bio-printed entity is a hepatocyte (HC).

In some embodiments, a cell associated with the bio-printed entity is a primary human hepatocyte (PHH).

In some embodiments, a cell associated with the bio-printed entity is a hepatic stellate cell (HSCs).

In some embodiments, a cell associated with the bio-printed entity is a Kupffer cell (KC).

In some embodiments, a cell associated with the bio-printed entity is a liver sinusoidal endothelial cell (LSEC).

In some embodiments, a cell associated with the bio-printed entity is a mucous cell.

In some embodiments, a cell associated with the bio-printed entity is a parietal cell.

In some embodiments, a cell associated with the bio-printed entity is a chief cell.

In some embodiments, a cell associated with the bio-printed entity is an endocrine cell (e.g., a G cell, a D cell, an enterochromaffin cell, a EC-like cell, a X/A cell).

In some embodiments, a cell associated with the bio-printed entity is a columnar epithelial cell.

In some embodiments, a cell associated with the bio-printed entity is a cardiac fibroblast (CF).

In some embodiments, a cell associated with the bio-printed entity is a cardiomyocyte.

In some embodiments, a cell associated with the bio-printed entity is a smooth muscle cell.

In some embodiments, a cell associated with the bio-printed entity is an enterocyte.

In some embodiments, a cell associated with the bio-printed entity is a goblet cell.

In some embodiments, a cell associated with the bio-printed entity is a Paneth cell.

In some embodiments, a cell associated with the bio-printed entity is a stem cell.

In some embodiments, a cell associated with the bio-printed entity is a neuron.

In some embodiments, a cell associated with the bio-printed entity is a glia.

In some embodiments, a cell associated with the bio-printed entity is a keratinocyte.

In some embodiments, a cell associated with the bio-printed entity is a melanocyte.

In some embodiments, a cell associated with the bio-printed entity is a Merkel cell.

In some embodiments, a cell associated with the bio-printed entity is a Langerhans cell.

In some embodiments, a cell associated with the bio-printed entity is a germ cell.

In some embodiments, a cell associated with the bio-printed entity is a stromal cell.

In some embodiments, a cell associated with the bio-printed entity is a seminiferous tubule.

In some embodiments, a cell associated with the bio-printed entity is a Leydig cell.

In some embodiments, a cell associated with the bio-printed entity is a tubule epithelial cell.

In some embodiments, a cell associated with the bio-printed entity is a macula densa cell.

In some embodiments, a cell associated with the bio-printed entity is a glomerular endothelial cell.

In some embodiments, a cell associated with the bio-printed entity is a podocyte.

In some embodiments, a cell associated with the bio-printed entity is a mesangial cell.

In some embodiments, a cell associated with the bio-printed entity is a parietal epithelial cell.

In some embodiments, a cell associated with the bio-printed entity is an immortalized cell (e.g., a 3T3 cell, a A549 cell, a HeLa cell, a HEK 293 cell, a HEK 293T cell, a Huh7 cell, a Jurkat cell, an OK cell, a Ptk2 cell, a Vero cell).

In some embodiments, a cell associated with a bioprinted entity is a patient-derived cell (e.g., a tumor cell).

In some embodiments, a cell associated with a bioprinted entity is a T cell.

In some embodiments, a cell associated with a bioprinted entity is a peripheral blood mononuclear cell (PBMC).

In some embodiments, a cell associated with a bioprinted entity is an induced pluripotent stem cell (iPSC).

In some embodiments, a cell associated with the bio-printed entity is a combination of one or more cells as described above and herein. In some embodiments, a combination of cells may comprise an endothelial cell and/or a cell other than an endothelial cell. In some embodiments, a combination of cells may comprise a liver parenchymal cell, a PHH, and/or an endothelial cell.

Those skilled in the art, reading the present disclosure, will appreciate that, in some embodiments, interaction of a cell with a bioprinted entity comprising a particular polymer moiety may be adjusted, for example through linkage of a plurality of cells, which may be the same or different.

In some embodiments, a cell associated with a bioprinted entity as described above and herein forms a tissue.

Scaffold Formation

In some embodiments, a bioprinted entity comprises a biocompatible resin and a bioprinted vascularized scaffold. In some such embodiments, a bioprinted entity comprises at least one chamber into which a cell in media may be pipetted.

In some embodiments, the vascularized scaffold may go through the chambers. In some embodiments, aspects of the vascularized scaffold may be controlled (e.g., wall thickness, lumen diameter, porosity, architecture) to provide alternate properties. It is also understood that the vascularized scaffold may comprise more than one independent network (e.g., vasculature, a bile duct). In some embodiments, bio-printing methodologies, systems, and technologies described herein may be overlapping with, similar to, substantially similar to, and/or identical to those described in U.S. Pat. Nos. 10,639,880 and/or 10,828,833.

Figure 28:
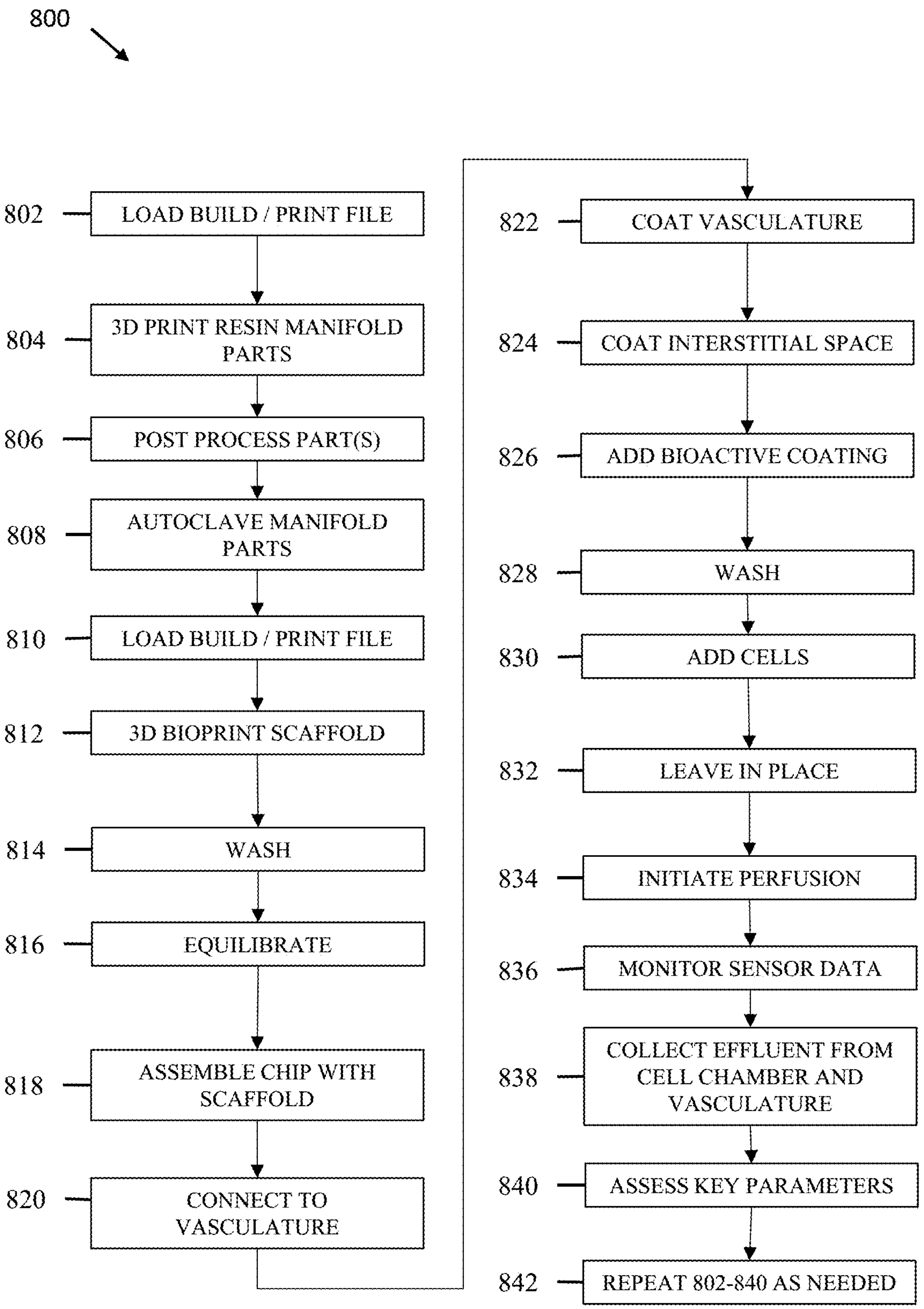
FIG. 28 illustrates a method of creating, seeding, and operating an organ on a chip platform, according to aspects of the present embodiments.

FIG. 28 illustrates a method 800 of creating, seeding, and operating an organ on a chip platform, according to aspects of the present embodiments. At step 802, the method 800 may include loading an electronic build or print file onto a 3D printer (for example, a printer that uses digital light processing (DLP) to print polymer parts). At step 804, the method 800 may include 3D printing (i.e., additively manufacturing) resin manifold parts. At step 806, the method 800 may include post processing steps (such as deburring to remove any abnormalities, smoothing, finishing steps, etc.). At step 808, the method 800 may include autoclaving the printed parts to help encourage and expedite curing. At step 810, the method 800 may include loading an electronic build or print file onto a 3D printer (for example, a 3D-bio printer that uses DLP to print bioactive parts). At step 812, the method 800 may include 3D printing (i.e., additively manufacturing) bioprinted scaffolding. At steps 814 and 816, the method 800 may include washing and equilibrating the bioprinted scaffolding. At step 816, the method 800 may include assembling the bioprinted scaffolding within a hydrogel chip (for example, via an access port in the chip). At step 820, the method 800 may include connecting the vasculature to a system (i.e., perfusion system, flow rig, bioreactor, etc.) that fluidly couples flow lines such that bio-fluids may flow through the vasculature. At step 822, the method 800 may include coating the internal walls of the vasculature with a chemical linker. At step 824, the method 800 may include coating the interstitial space with a chemical linker.

Referring still to FIG. 28, the method may include washing the internal walls of the vasculature and the interstitial space, after the chemical linker is added. At step 828, the method 800 may include adding a bioactive molecular coating to the interior walls of the vasculature and the interstitial space, which again then may be washed leaving behind a homogenous layer of coating. At step 832, the method 800 may include leaving the cells in place for a period of time (for example, 2 hours, 4 hours, 6 hours, 8 hours, 10 hours, overnight, 12 hours, 16 hours, 24 hours, 48 hours, etc.) allowing the cells to attached to the respective surfaces. At step 834, the method 800 may include initiating perfusion. At step 836, the method 800 may include monitoring sensor data. At step 838, the method 800 may include collecting effluent flow from the cell chamber and vasculature. At step 840, the method 800 may include assessing key parameters. At step 842, the method 800 may include repeating any of the previous steps.

Figure 29:
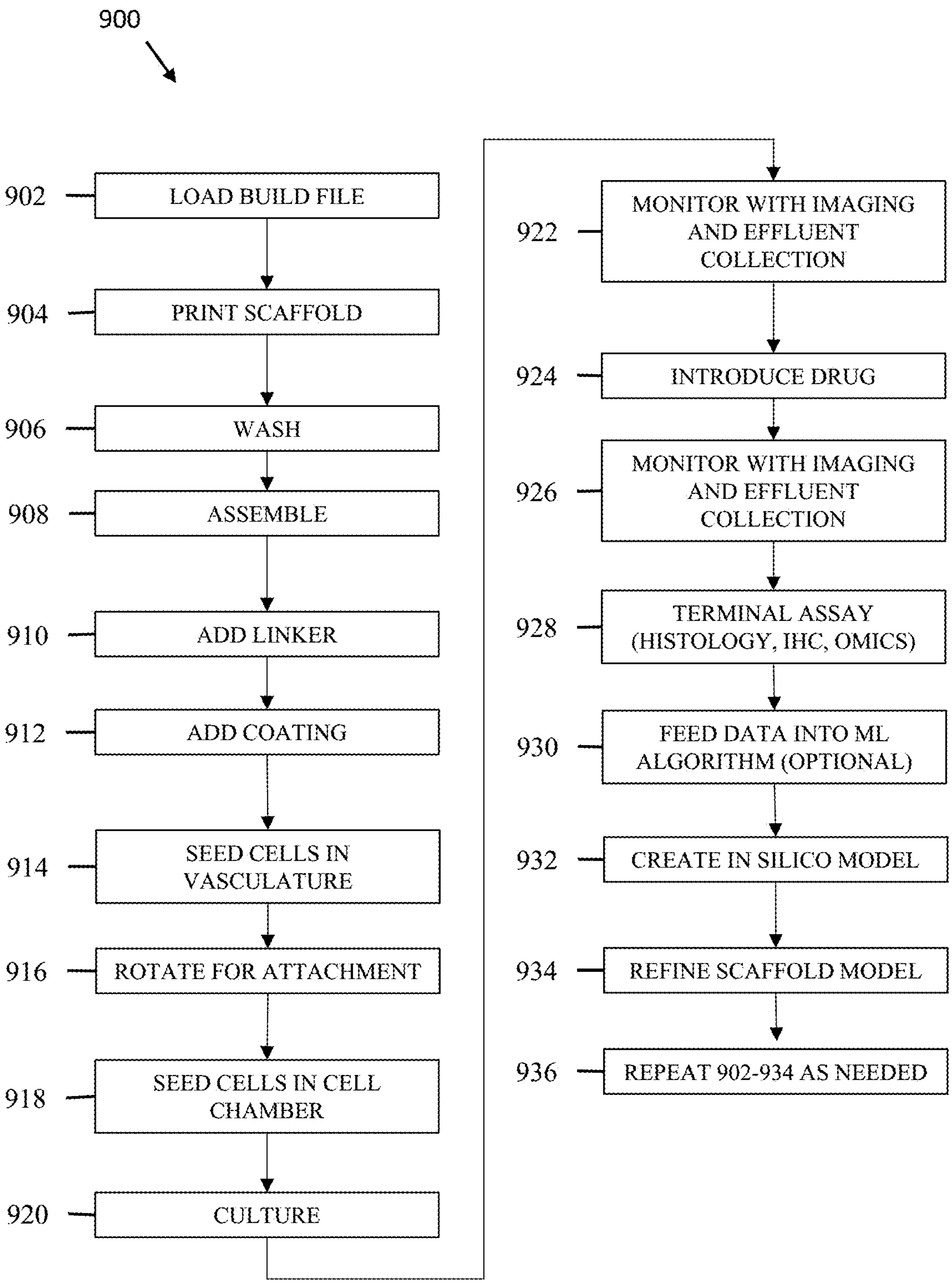
FIG. 29 illustrates a method of creating, seeding, and operating an organ on a chip platform, according to aspects of the present embodiments.
Figure 30:
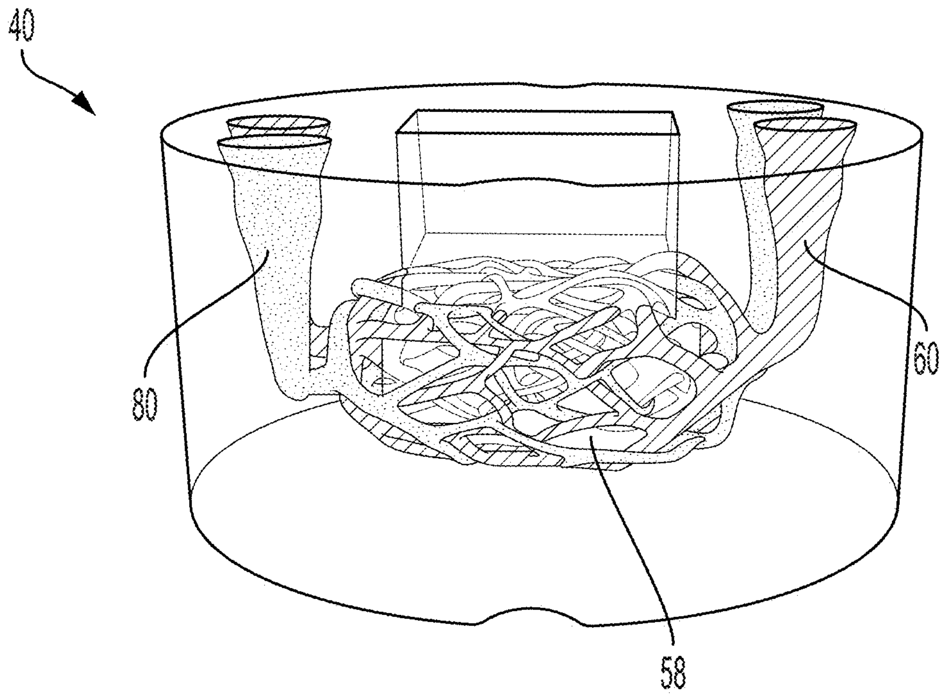
FIG. 30 illustrates a liver-on-a-chip model, according to aspects of the present embodiments.
Figure 31:
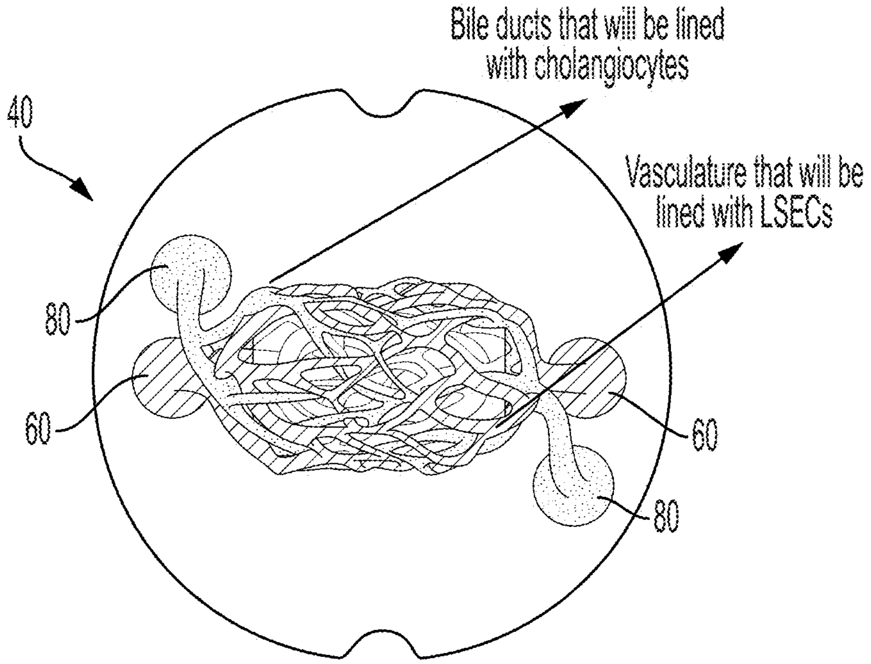
FIG. 31 illustrates a liver-on-a-chip model, according to aspects of the present embodiments.
Figure 32:
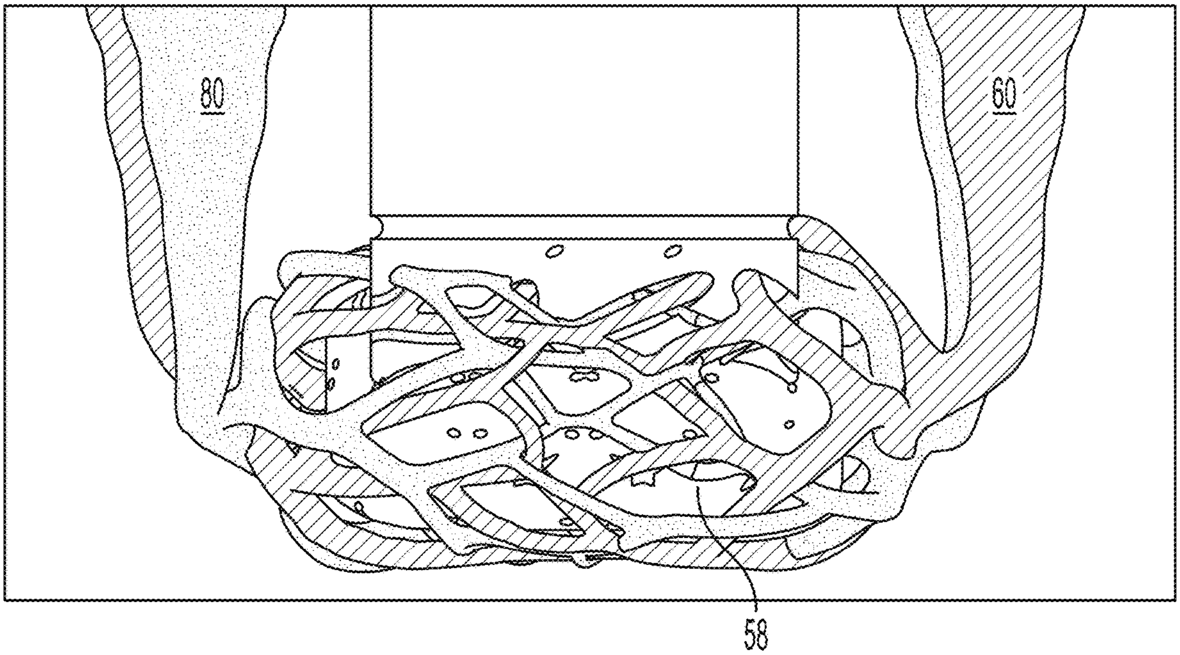
FIG. 32 illustrates a liver-on-a-chip model, according to aspects of the present embodiments.
Figure 33:
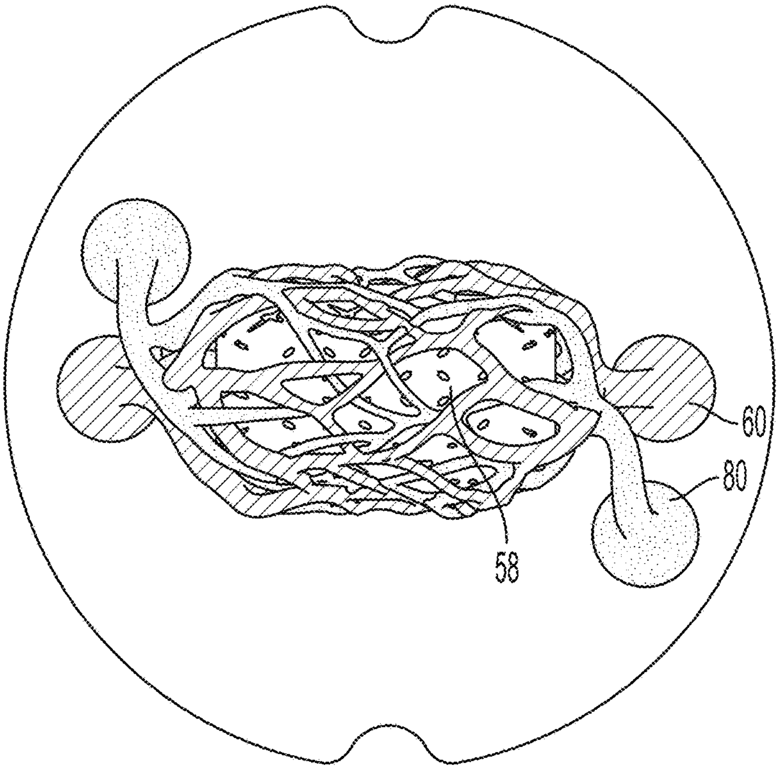
FIG. 33 illustrates a liver-on-a-chip model, according to aspects of the present embodiments.
Figure 34:
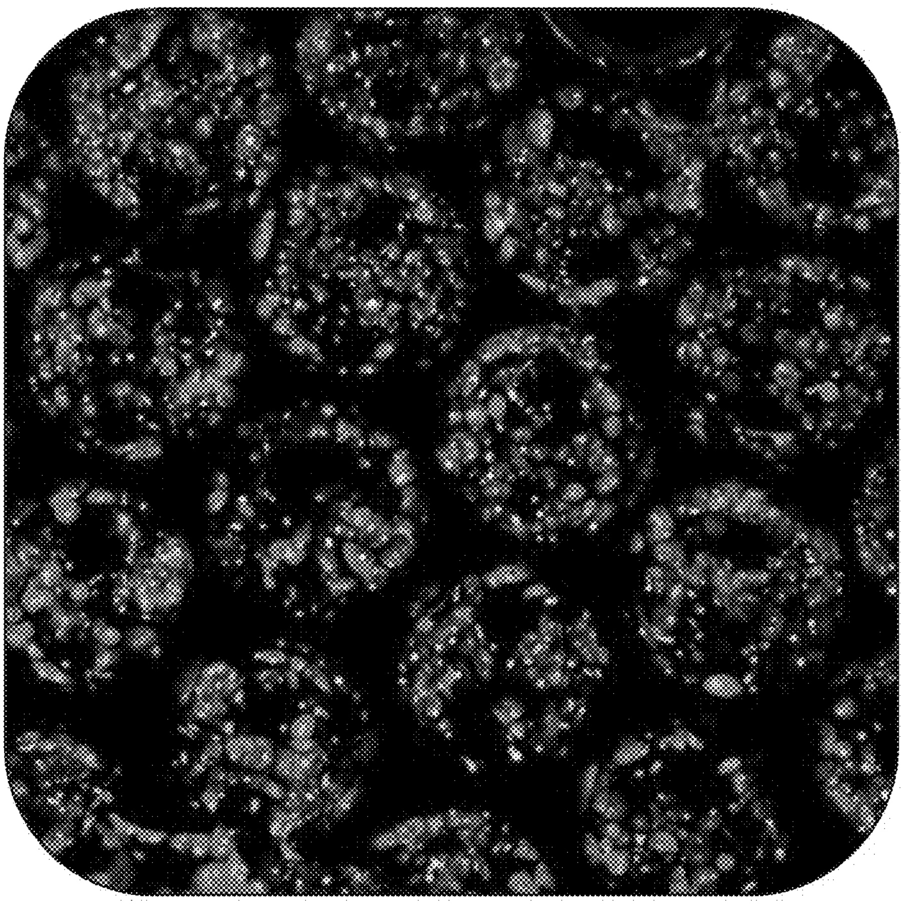
FIG. 34 illustrates fluorescent imaging of liver-on-a-chip tissue, according to aspects of the present embodiments.
Figure 35:
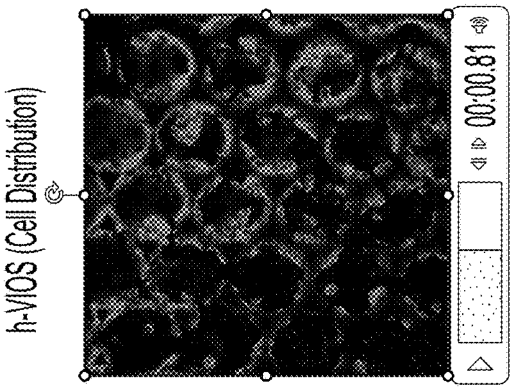
FIG. 35 illustrates fluorescent imaging of liver-on-a-chip tissue, according to aspects of the present embodiments.
Figure 36:
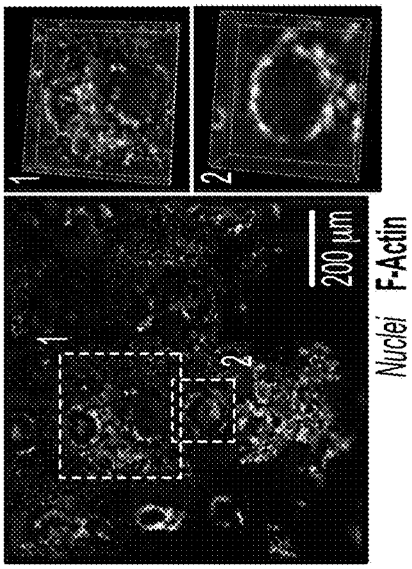
FIG. 36 illustrates fluorescent imaging of liver-on-a-chip tissue, according to aspects of the present embodiments.
Figure 37A:
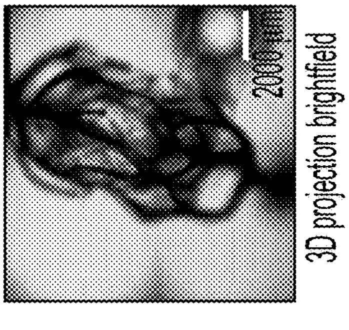
FIGS. 37A-37E illustrate fluorescent imaging of liver-on-a-chip vasculature, according to aspects of the present embodiments.
Figure 37B:
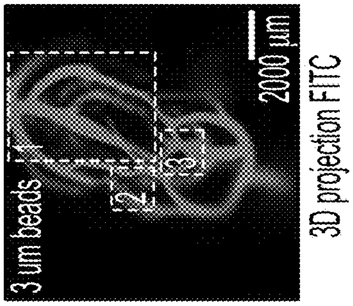
Figure 37C:
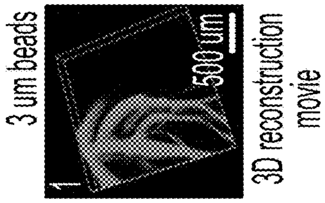
Figure 37D:
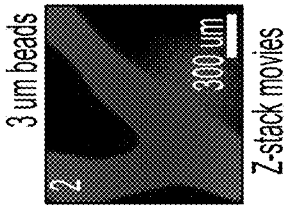
Figure 37E:
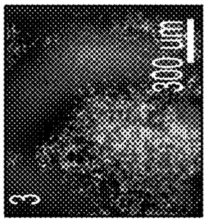

FIG. 29 illustrates a method 900 of creating, seeding, and operating an organ on a chip platform, according to aspects of the present embodiments. Several of the steps of the method 900 shown in FIG. 29 are similar to or the same as steps of method 800 illustrated in FIG. 28. At step 916, the method 900 may include rotating the printed platform to encourage cell attachment. At step 922, the method 900 may include monitoring the process concurrent with imaging and effluent collection. At step 924, the method 900 may include introducing a drug through the vasculature (such that, in some embodiments, it may transport across the vasculature walls into the cells in the interstitial space). At step 926, the method 900 may include monitoring the process concurrent with imaging and effluent collection following introduction of the drug(s). At step 928, the method 900 may include performing one or more terminal assays (for example, histology, IHC, omics, etc.). At step 930, the method 900 may include feeding data into a machine learning (ML) algorithm. At step 932, the method 900 may include creating an in silico model. At step 932, the method 900 may include refining the geometry of the scaffold model (i.e., to be reprinted) based on the in silico model. At step 936, the method 900 may include repeating any of the previous steps.

Figure 2:
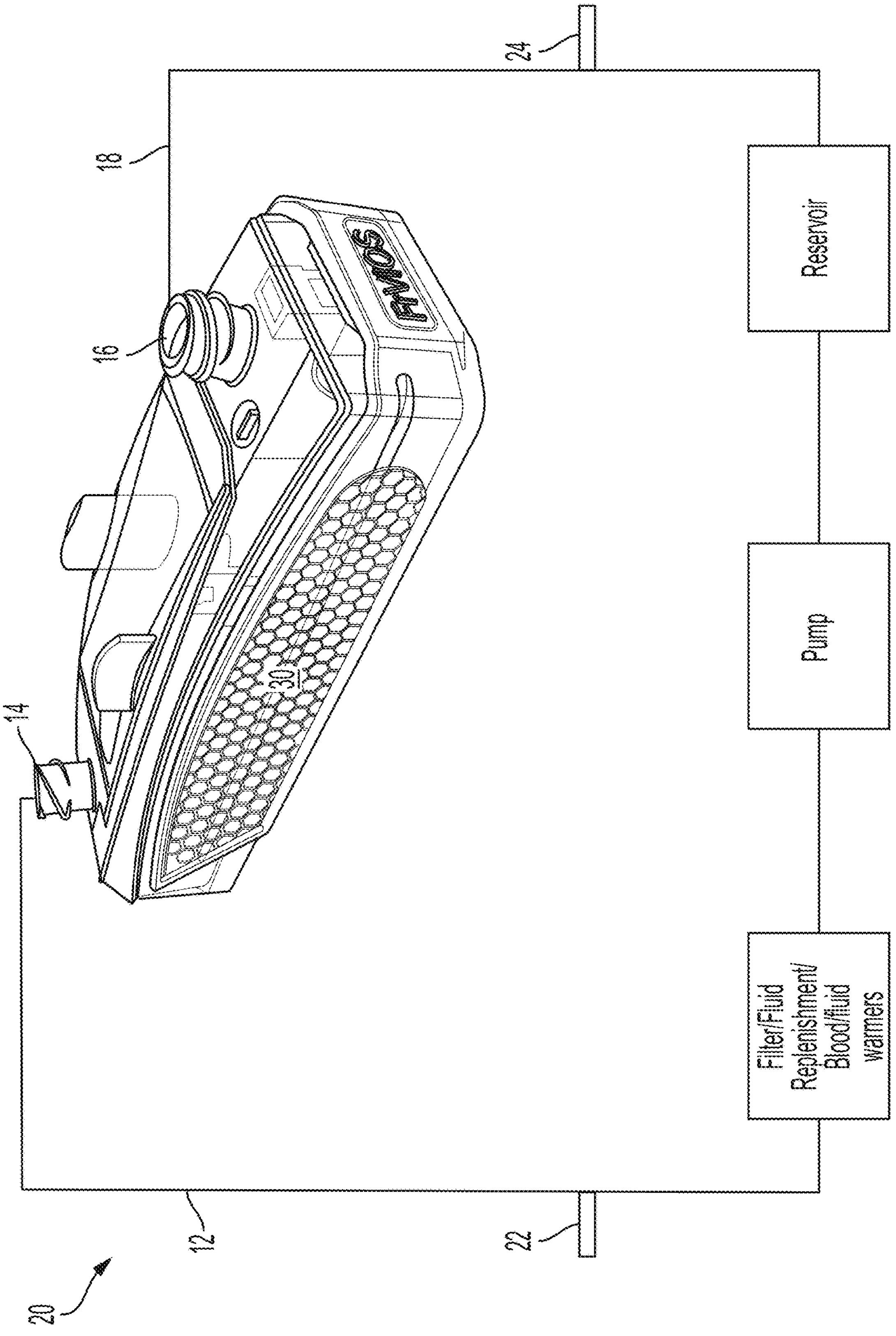
FIG. 2 illustrates a platform for modeling organ-on-a-chip and other biological models, according to aspects of the present embodiments.

FIG. 2 illustrates a system 20 and platform 30 for modeling organ-on-a-chip and other biological models, according to aspects of the present embodiments. The system 20 may include a platform 30 (for example, a 3D printed assembly as described herein) as well as other components such as an inlet line 12 coupled to an inlet port 14 (or inlet flow line) of the platform 30, and outlet lint 18 coupled to an outlet port 16 (or outlet flow line) of the platform, one or more sensors 22, 24 disposed in the inlet and/or outlet lines 12, 18, a reservoir, a pump, and other potential components such as filters, fluid replenishment systems, blood/fluid warmers, etc. The platform 30 may include one or more internal chips that include internal vasculatures and are fluidly coupled to the inlet and outlet ports 14, 16. The system 20 may be used, for example, to perfuse organs and/or to study the functioning of organs in a simulated and active (i.e., including live cells) environment.

Figure 3:
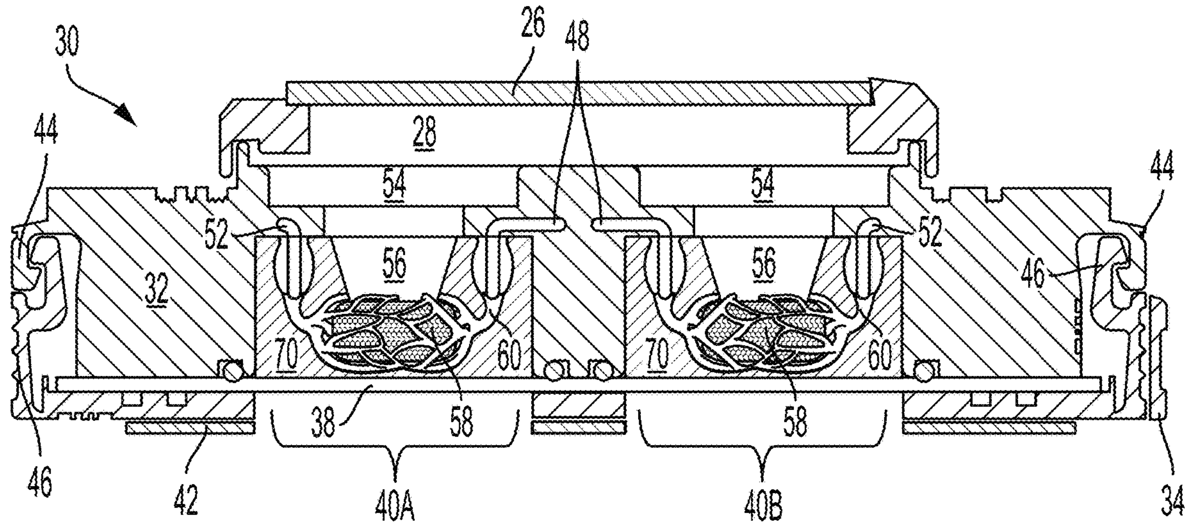
FIG. 3 illustrates a side view of platform for modeling organ-on-a-chip and other biological models, according to aspects of the present embodiments.
Figure 4:
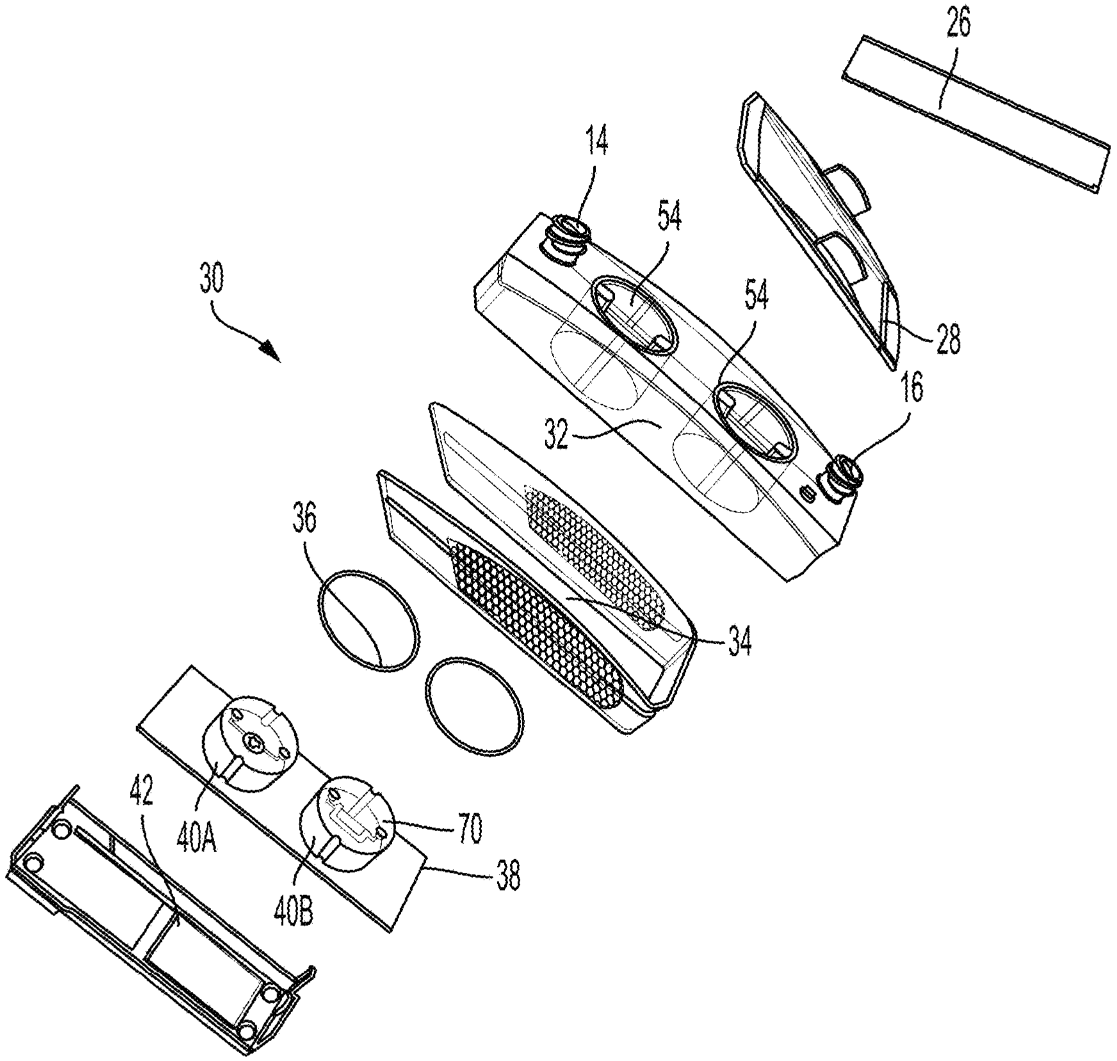
FIG. 4 illustrates a platform assembly, according to aspects of the present embodiments.

FIG. 3 illustrates a side view of platform 30 for modeling organ-on-a-chip and other biological models, according to aspects of the present embodiments. FIG. 4 illustrates a platform assembly 30, according to aspects of the present embodiments. The platform/platform assembly may include a base 42, a glass based 38 configured to be seated in the base 42 and to support one or more chips 40A, 40B, O-rings 36 for sealing the chips 40A, 40B to a glass cover 26, a clip 34 laterally slidable across a case 32, and a cover retainer 28 for holding the glass cover 26 in place. The fluid inlet 14 and fluid outlet 16 are visible in FIG. 4. With the exception of the chips 40A, 40B, the glass base 42, the glass cover 26, and the O-rings 36, each of the other components of the platform assembly 30 (i.e., the base 42, the clip 34, the case 32, and the cover 28) may be formed via 3D printing and may be composed of a polymer material.

Referring again to FIG. 3, the platform 30 (specifically the base 42) may include a base clip 46 that is shaped to be engaged with a corresponding case clip 44 (i.e., integrally formed with the case 32) for holding the base 42 to the case 32. In some embodiments, the platform may include a base and case clips 46, 44 on each end. Each of the chips 40A, 40B may be disposed within the case 32 via corresponding recesses 54 disposed within the case 32. Each chip 40A, 40B may include an internal 3D printed scaffold 70 with an internal vasculature 60 disposed therein. The scaffold 70 may be formed of hydrogel material. The vasculature 60 may include a vasculature inlet 48 and a vasculature outlet 52, both being fluidly coupled (via microchannels disposed within the case 32 (not shown)) to the respective fluid inlet 14 and fluid outlet 16 disposed in the case 32. The vasculature 60 may include a network of flow passages fluidly connecting the vasculature inlet 48 (or inlet flow passage 48) and vasculature outlet 52 (or outlet flow passage 52), and geometrically defining the boundaries of an interstitial space defined therewithin. The platform 30 and chips 40A, 40B, may further comprise an interstitial infill 58 that includes an internal structure (for example, a 3D-printed repeating structure) enabling active cells to be seed thereto. Cells may be added into the interstitial space via an access port 56 disposed within the scaffold 70.

Figure 5:
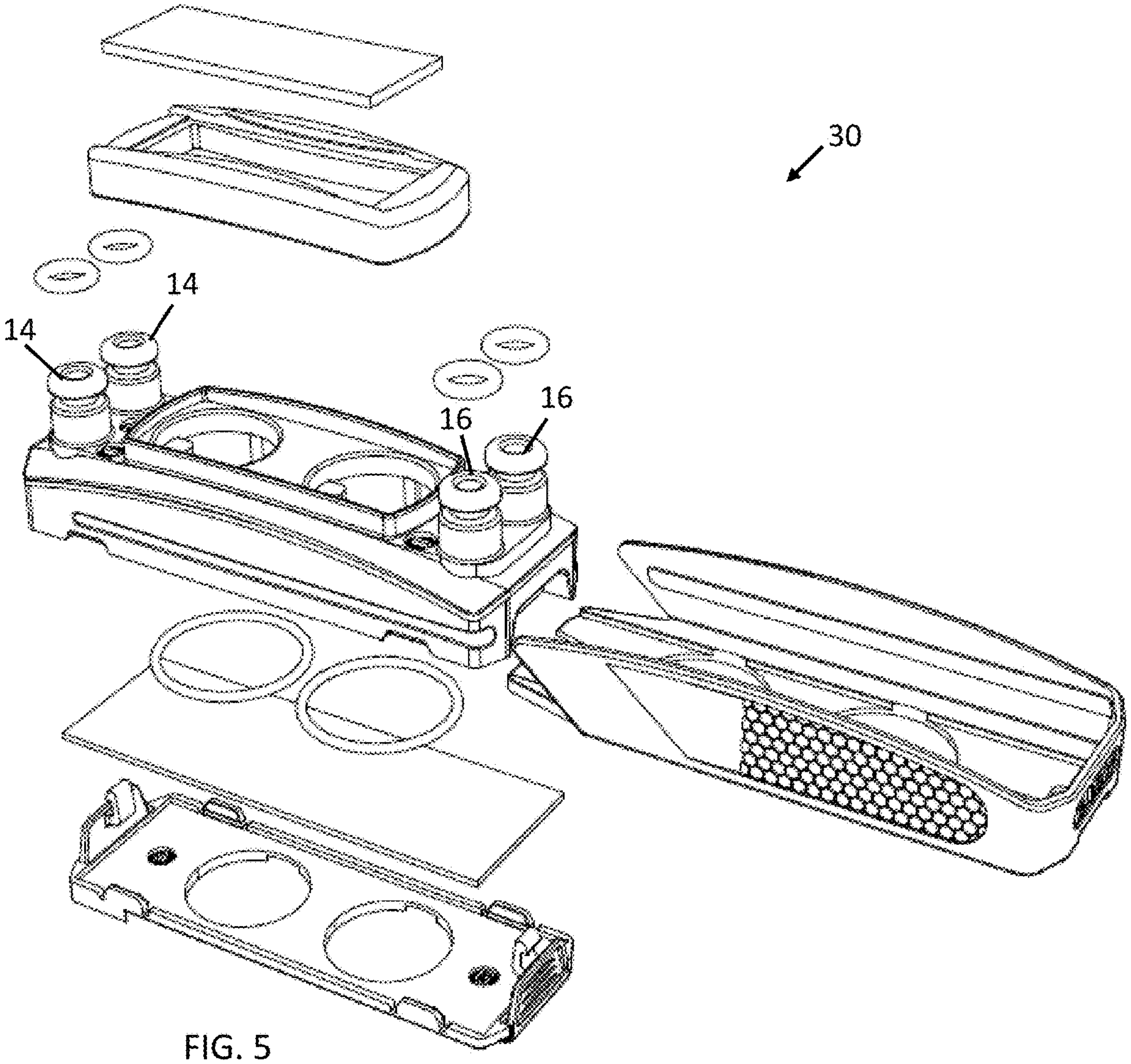
FIG. 5 illustrates a platform assembly, according to aspects of the present embodiments.

FIG. 5 illustrates a platform assembly 30, according to aspects of the present embodiments. In the embodiment of FIG. 5, the platform 30 includes two fluid inlets 14 and two fluid outlets 16. This configuration enables different fluids to be routed to the two cells. This configuration also enables two different fluids to be routed to each of the two cells, as further described herein in connection with FIGS. 30-33.

Figure 6:
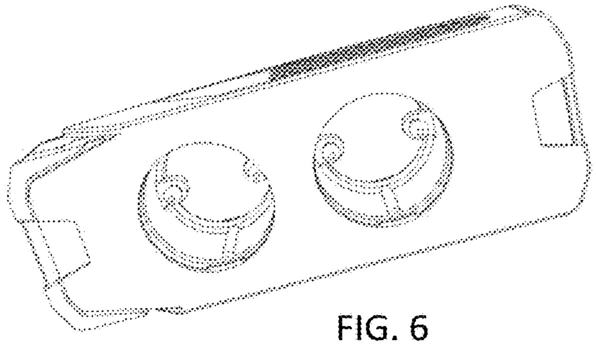
FIG. 6 illustrates a bottom view of a platform assembly, according to aspects of the present embodiments.

FIG. 6 illustrates a bottom view of a platform assembly 30, according to aspects of the present embodiments. The platform may be configured to accommodate different numbers of cells including but not limited to 1, 2, 3, 4, 5, 8, 10, 15, 16, 20, 50, 100, 1000, and more than 1000 cells.

Figure 7:
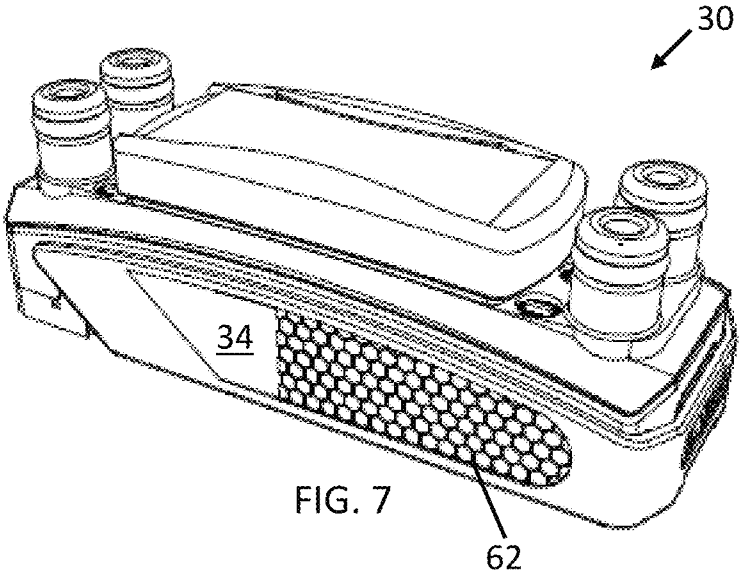
FIG. 7 illustrates a perspective view of a platform assembly, according to aspects of the present embodiments.

FIG. 7 illustrates a perspective view of a platform assembly 30, according to aspects of the present embodiments. In the illustration of FIG. 7, a grip surface 62 is disposed in the clip 34 to help facilitate sliding the clip 34 on and off.

Figure 8:
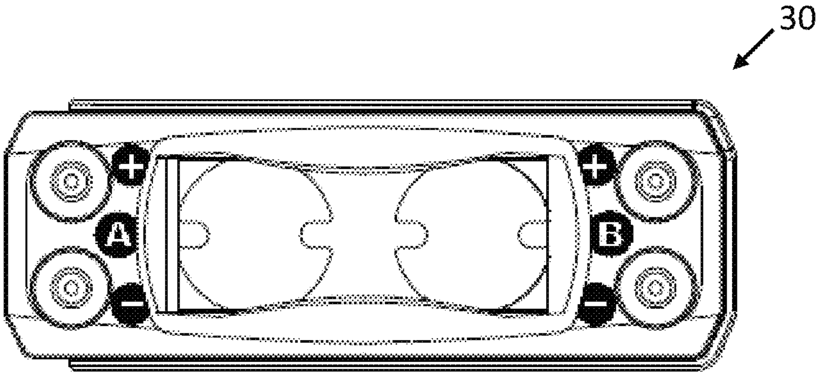
FIG. 8 illustrates atop view of a platform assembly, according to aspects of the present embodiments.

FIG. 8 illustrates atop view of a platform assembly, according to aspects of the present embodiments.

Figure 9:
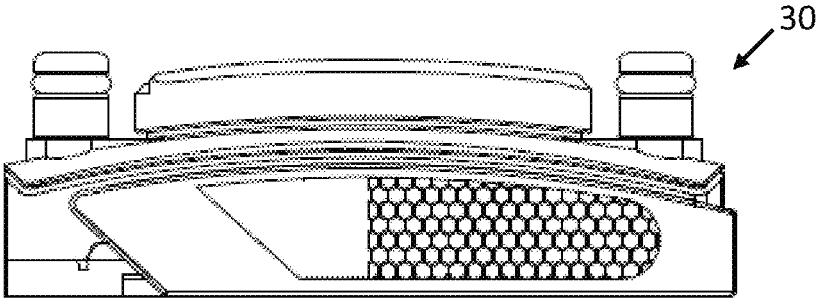
FIG. 9 illustrates a side view of a platform assembly, according to aspects of the present embodiments.

FIG. 9 illustrates a side view of a platform assembly, according to aspects of the present embodiments.

Figure 10:
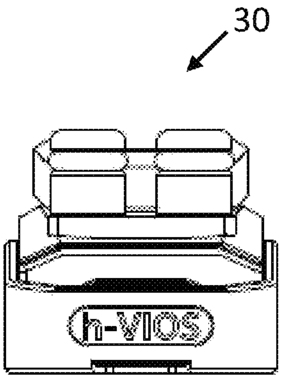
FIG. 10 illustrates a front view of a platform assembly, according to aspects of the present embodiments.

FIG. 10 illustrates a front view of a platform assembly, according to aspects of the present embodiments.

Figure 11:
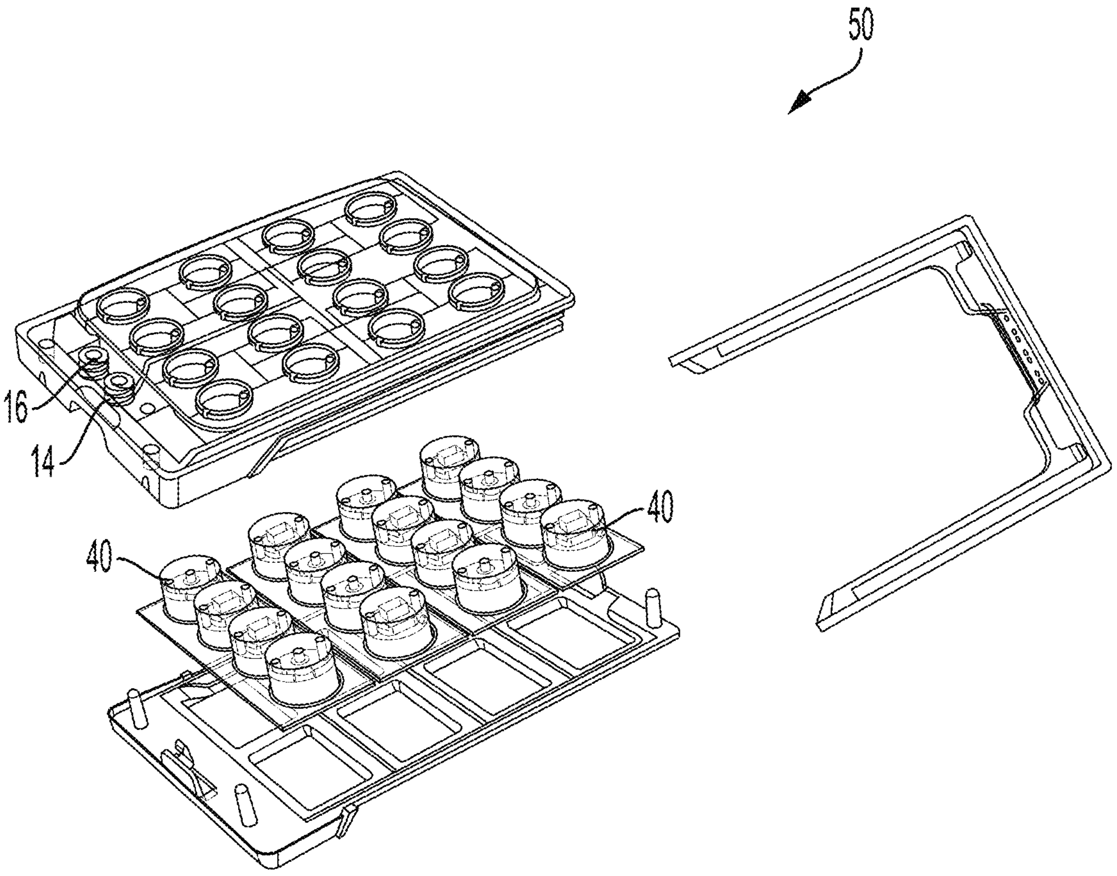
FIG. 11 illustrates a view of a platform assembly, according to aspects of the present embodiments.

FIG. 11 illustrates a view of a platform assembly 50, according to aspects of the present embodiments. The platform assembly 50 includes a 4×4 grid of recesses enabling 16 cells to be disposed therein. In some embodiments, the platform 30 includes an internal micro-fluid framework that acts as a manifold such that fluids can be route to and from each of the (in this case) 16 cells 40, via only a single fluid inlet 14 and a single fluid outlet 16.

Figure 12A:
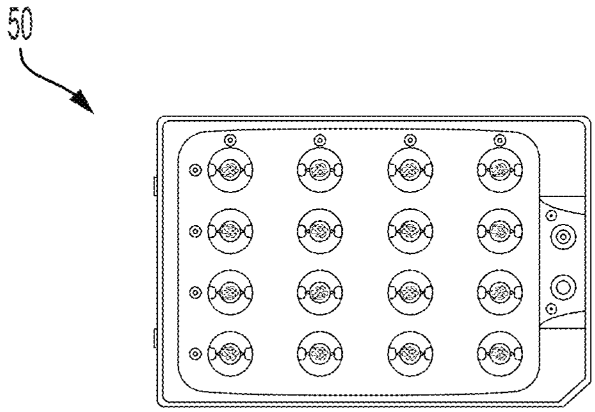
FIGS. 12A and 12B illustrate views of a platform assembly, according to aspects of the present embodiments.
Figure 12B:
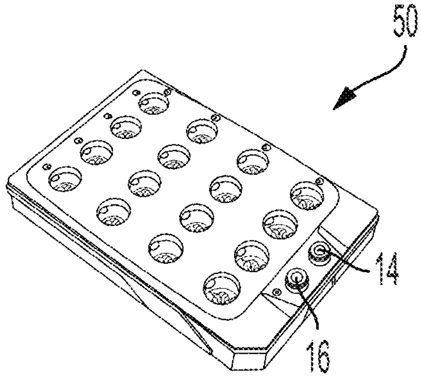

FIGS. 12A and 12B illustrate views of a platform assembly, according to aspects of the present embodiments.

Figure 13:
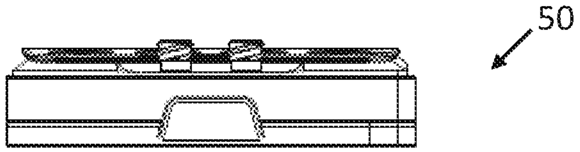
FIG. 13 illustrates a view of a platform assembly, according to aspects of the present embodiments.

FIG. 13 illustrates a view of a platform assembly, according to aspects of the present embodiments.

Figure 14:
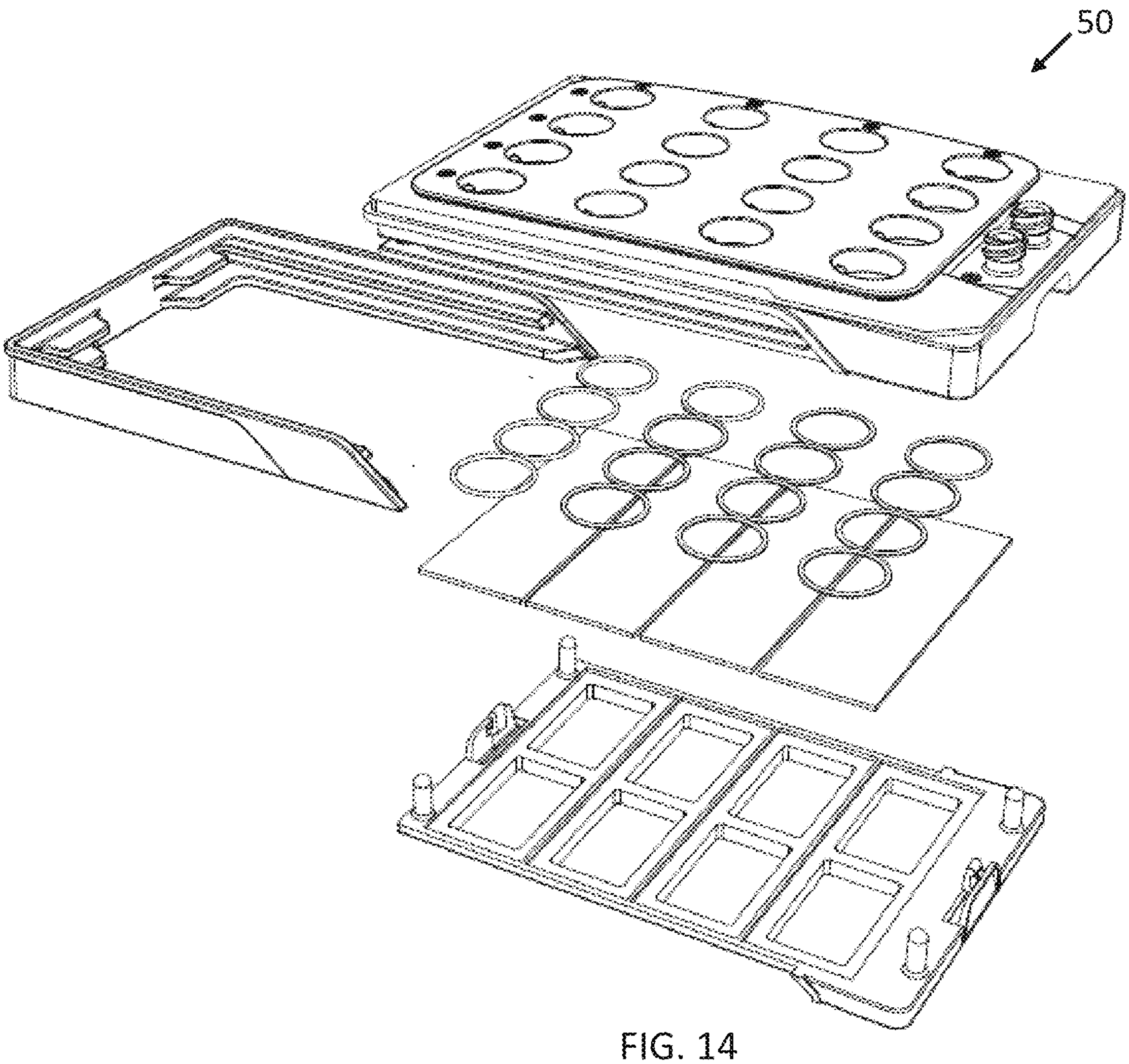
FIG. 14 illustrates a view of a platform assembly, according to aspects of the present embodiments.
Figure 15A:
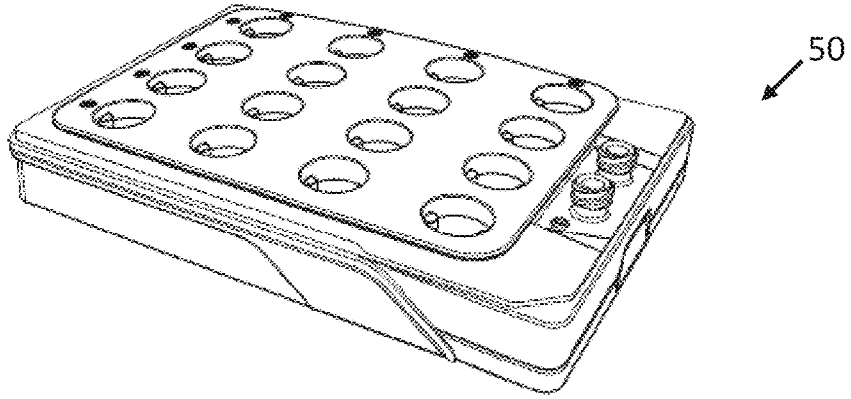
FIGS. 15A, 15B, 15C, and 15D illustrate views of a platform assembly, according to aspects of the present embodiments.
Figure 15B:
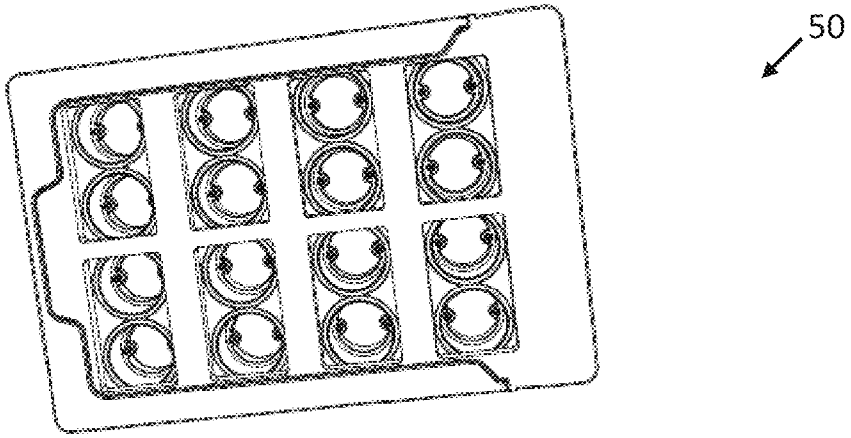
Figure 15C:
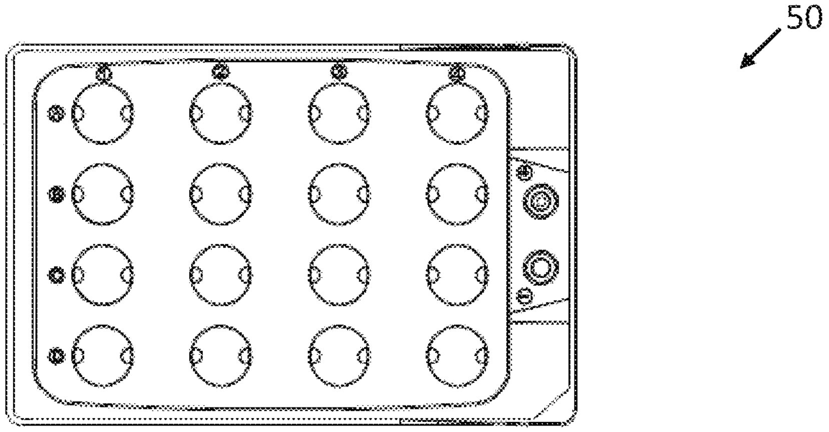
Figure 15D:
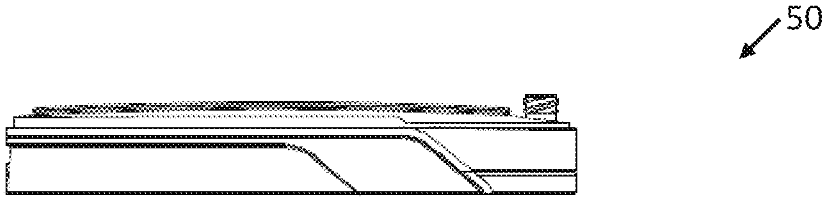

FIG. 14 illustrates a view of a platform assembly, according to aspects of the present embodiments.

FIGS. 15A, 15B, 15C, and 15D illustrate views of a platform assembly, according to aspects of the present embodiments.

Figure 16:
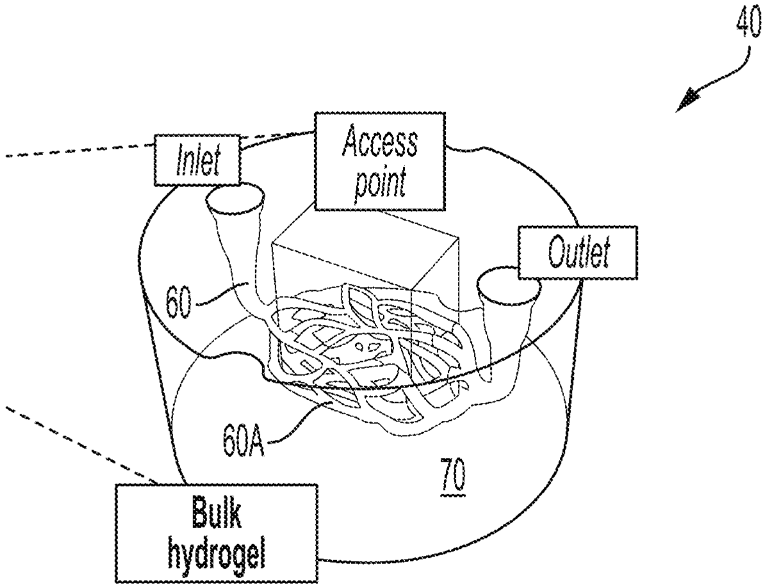
FIG. 16 illustrates a view of an organ chip, according to aspects of the present embodiments.

FIG. 16 illustrates a view of an organ chip 60, according to aspects of the present embodiments. As shown in FIG. 16, the vasculature 60 disposed within the hydrogel scaffold 70 of the chip 40 may have a larger diameter at each of the inlet and outlets, and may include a plurality or network of smaller vasculature passages 60A connecting therebetween. In some embodiments, the internal diameter of the vasculature decreases from the vasculature inlet to a center of the cell 40, and then increases from the center of the cell to the vasculature outlet.

Figure 17:
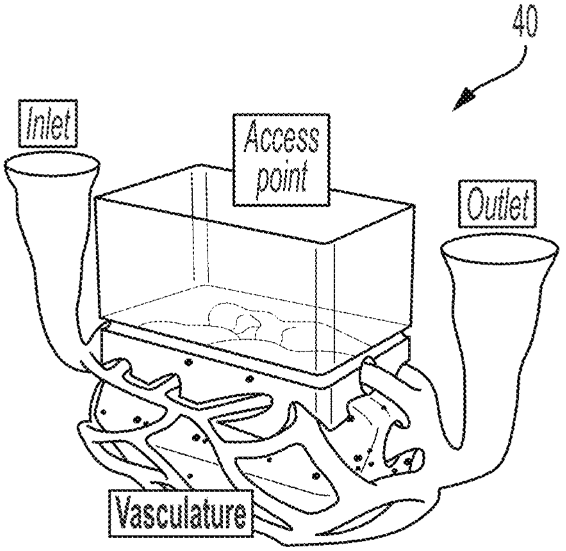
FIG. 17 illustrates a view of an organ chip, according to aspects of the present embodiments.

FIG. 17 illustrates a view of an organ chip, according to aspects of the present embodiments.

Figure 18:
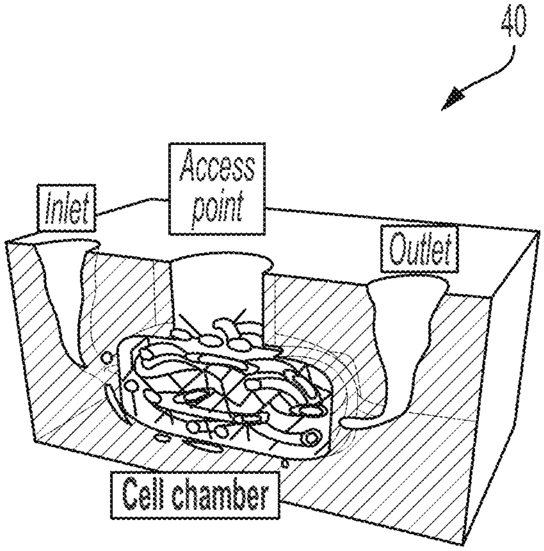
FIG. 18 illustrates a view of an organ chip, according to aspects of the present embodiments.

FIG. 18 illustrates a view of an organ chip, according to aspects of the present embodiments.

FIG. 19 illustrates a view of organ chips 40A, 40B within a platform 30 assembly, according to aspects of the present embodiments. The platform 30 may include a first chip 40A that includes a scaffold including a vasculature that is representative of a tumor, and a second chip 40B that includes a scaffold including a vasculature that is representative of a liver. The platform 30 may include one or more sensors 64 disposed within the vasculature, within the interstitial space, as well as in other potential locations such as in the inlet and outlet lines 12, 18 (shown in FIG. 2). The one or more sensors 64 may include sensors for measuring luminescence, colorimetry, electrochemical activity, fluorescence, and/or metabolic activity.

FIGS. 20A, 20B, and 20C illustrate views of vasculature configurations, according to aspects of the present embodiments. In the configuration shown in FIG. 20A, the vasculature 60 includes a single passageway or channel through the interstitial infill 58. The vasculature 60 may take a serpentine path making several turns (for example 90, 180, 270, and/or other number of degree turns) through the interstitial infill 58. In the configuration shown in FIG. 20B, the scaffold 70 may include multiple vasculatures 60 (or channels, or passageways), each vasculature 60 including an internal network of connections or passageways disposed within the interstitial infill 58 between a vasculature inlet and a vasculature outlet. In the configuration shown in FIG. 20B, the multiple vasculatures 60 may not connect to each other. In the configuration shown in FIG. 20C, the scaffold 70 may include an open vasculature 60 where passageways connect to adjacent passageways within the interstitial infill 58 forming a two dimensional and/or three dimensional interconnected vascular 60.

Figure 21A:
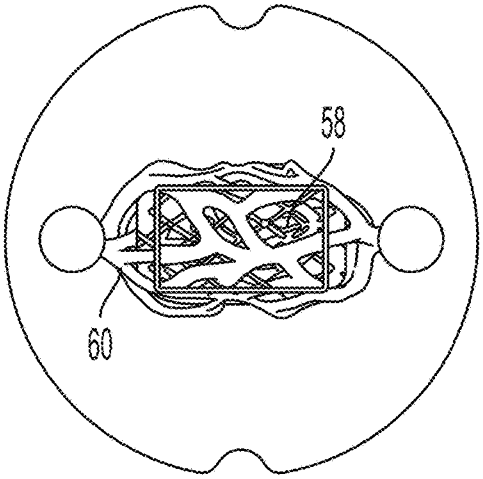
FIGS. 21A and 21B illustrate views of vasculature configurations, according to aspects of the present embodiments.
Figure 21B:
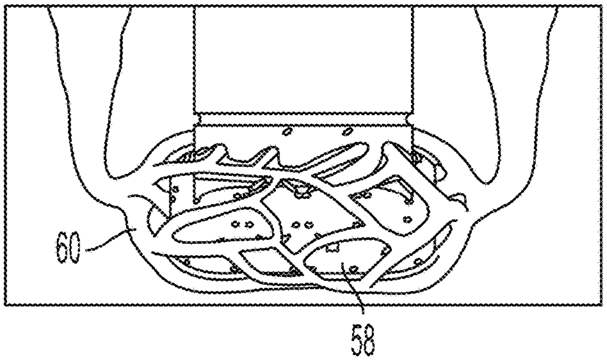
Figure 22:
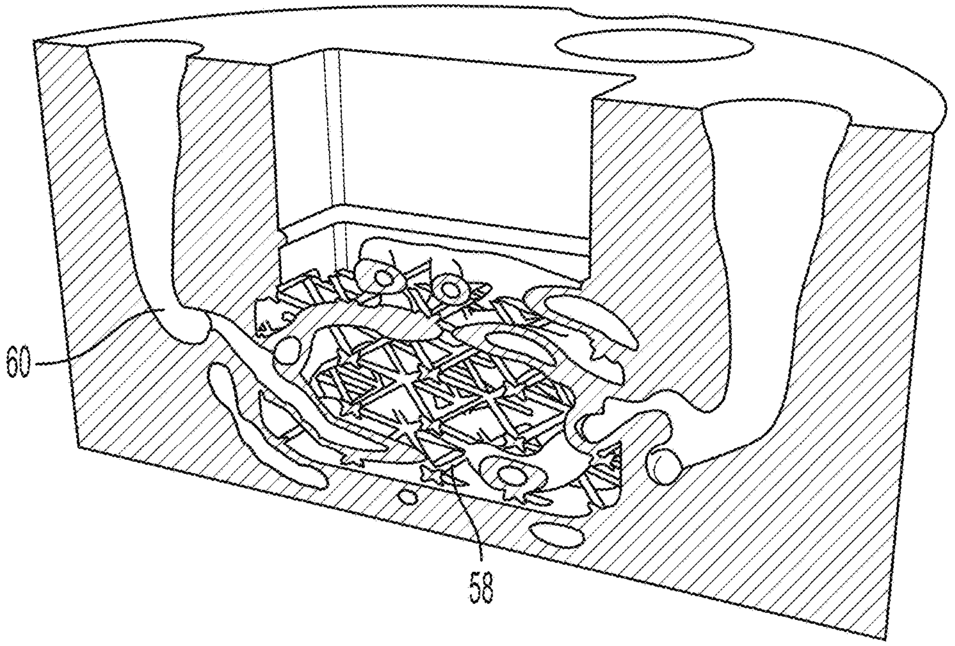
FIG. 22 illustrates a view of a vasculature configuration, according to aspects of the present embodiments.

FIGS. 21A, 21B and 22 illustrate views of vasculature configurations 60, according to aspects of the present embodiments. In the embodiments illustrated in FIGS. 21A, 21B and 22, the interstitial infill 58 includes a repeating lattice structure or framework.

Figure 23A:
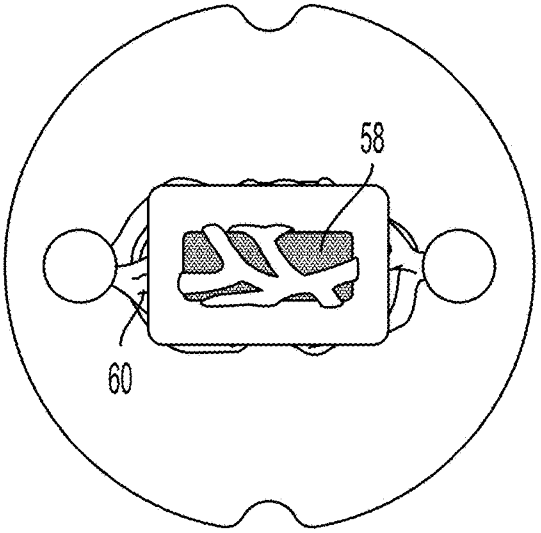
FIGS. 23A and 23B illustrate views of vasculature configurations, according to aspects of the present embodiments.
Figure 23B:
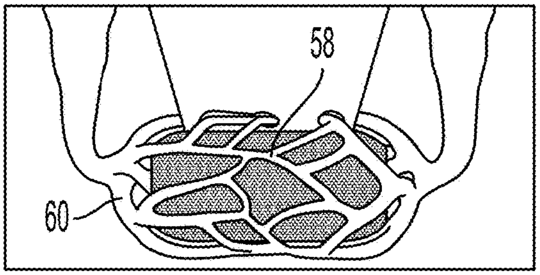
Figure 24:
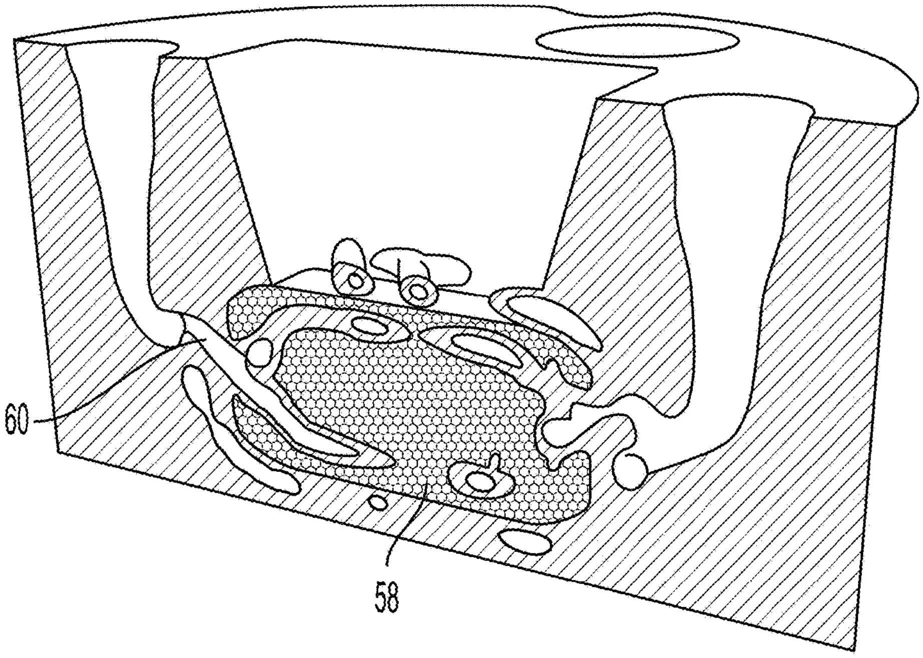
FIG. 24 illustrates a view of a vasculature configuration, according to aspects of the present embodiments.

FIGS. 23A, 23B, 24 illustrate views of vasculature configurations 60, according to aspects of the present embodiments. In the embodiments illustrated in FIGS. 23A, 23B and 24, the interstitial infill 58 includes a plurality of packed and interconnected microspheres.

Figure 25:
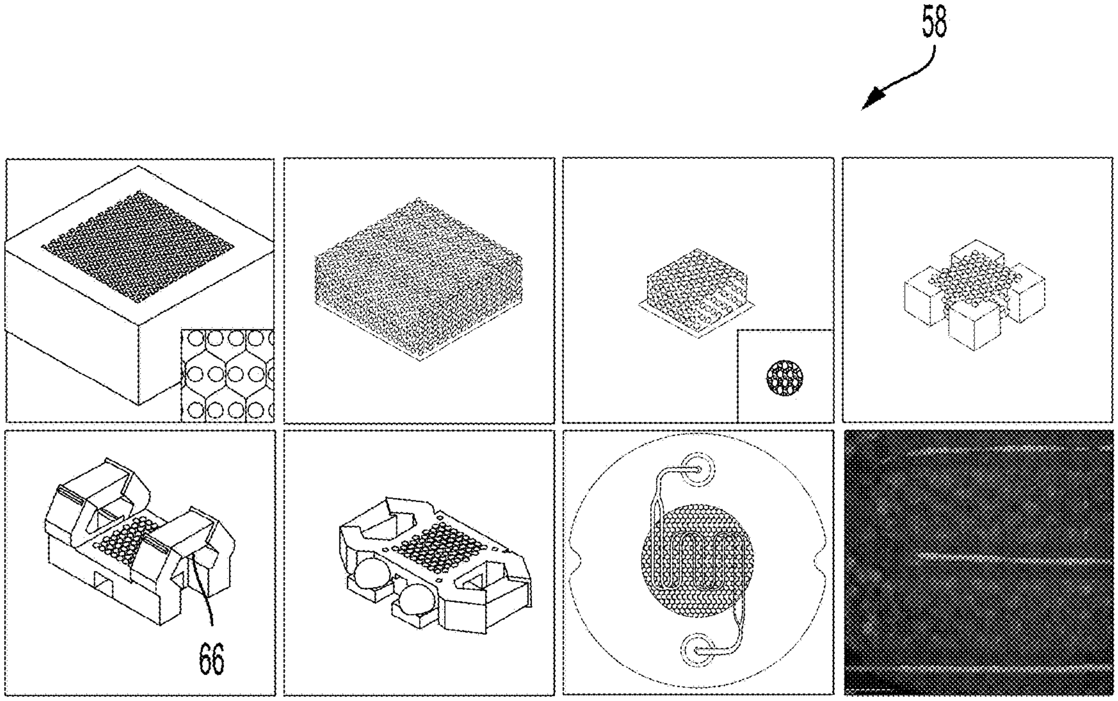
FIG. 25 illustrates views of interstitial infill, according to aspects of the present embodiments.

FIG. 25 illustrates views of interstitial infill 58, according to aspects of the present embodiments. In some configurations, the interstitial infill 58 may include one or more integral handles 66 and/or other features to facilitate handling of the interstitial infill 58.

Figure 26A:
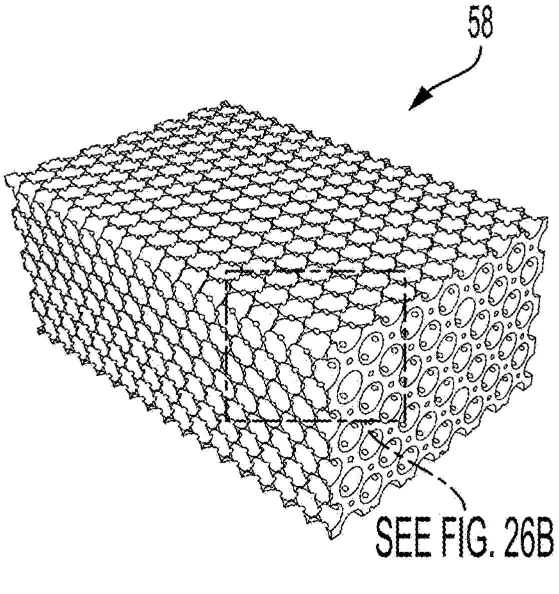
FIGS. 26A and 26B illustrate a view of interstitial infill, according to aspects of the present embodiments.
Figure 26B:
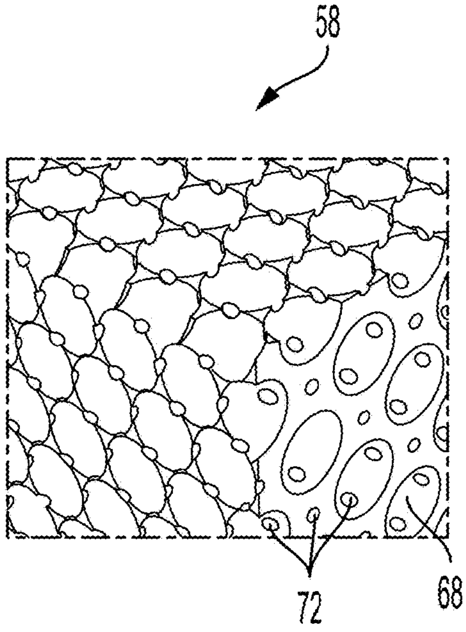

FIGS. 26A and 26B illustrate a view of interstitial infill 58, according to aspects of the present embodiments. In the embodiments illustrated in FIGS. 26A and 26B, the interstitial infill may include a lattice of interconnected spherical pores 68, connected via a plurality of interconnects 72. In some embodiments, the spherical pores 68 are connected to every adjacent spherical pore 68 via the interconnects 72. In some embodiments, the spherical pores 68 are not connected to every adjacent spherical pore 68 but are connected to 1) at least two adjacent spherical pores 68 in the same horizontal plane, 2) at least one adjacent spherical pore 68 in the next vertical layer higher of spherical pores, and 3) at least one adjacent spherical pore 68 in the next vertical layer lower of spherical pores. Accordingly, in some embodiments, each spherical pore 68 is connected to at least 4 adjacent spherical pores 68 via at least 4 corresponding interconnects 72.

Referring still to FIGS. 26A and 26B, in some embodiments, the framework 58 (or interstitial infill 58) illustrated in FIGS. 26A and 26B may be well suited for creating models of (e.g., synthetic) tissue such as liver tissue. In some embodiments, the each of the spherical pores 68 may have a diameter of about 300 μm (i.e., 300 microns) or from about 250 μm to about 350 μm, or from about 200 μm to about 400 μm, or from about 150 μm to about 450 μm. In some embodiments, each of the interconnects 72 may have a maximum dimension (i.e., diameter, length, major axis, etc.) of about 60 μm, or from about 55 μm to about 65 μm, or from about 50 μm to about 70 μm, or from about 45 μm to about 75 μm, or from about 40 μm to about 80 μm. The framework 58 (or interstitial infill 58) may be seeded with active cells via pipette. In some embodiments, the framework 58 (or interstitial infill 58) may be seeded with primary human hepatocyte and/or may be co-cultured with stellate cells and/or Kupffer cells. In some embodiments, the vasculature 60 that in which the framework 58 (or interstitial infill 58) is disposed may be seeded with sinusoidal endothelial cells. In some embodiments, the framework 58 (or interstitial infill 58) may also be disposed within a second vasculature (i.e., a bile duct) that is seeded with cholangiocytes lining the ducts (i.e., lining the interior vasculature 60 walls). In some embodiments, the framework 58 (or interstitial infill 58) is not vascularized (i.e., not disposed within a vasculature 60).

In some embodiments, the framework 58 (or interstitial infill 58) may be seeded at a density of from about 200,000 to about 1 million cell per chip.

Figure 27:
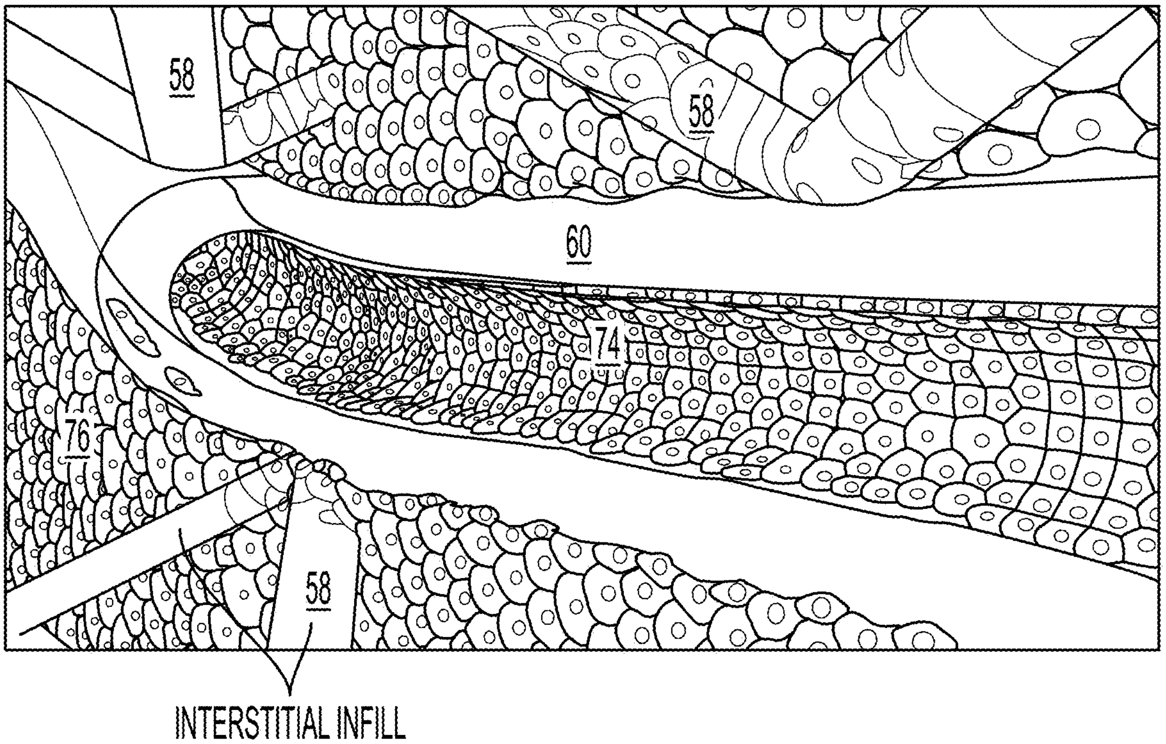
FIG. 27 illustrates a view of a vasculature and interstitial space seeded with active cells, according to aspects of the present embodiments.

FIG. 27 illustrates a view of a vasculature 60 and interstitial space seeded with active cells 76, 74, according to aspects of the present embodiments. The interstitial infill 58 is also shown in FIG. 27. In some embodiments, a first cell type 74 is seeded within the interior walls of the vascular 60 while a second cell type 76 is seeded in the interstitial space (and is supported by the interstitial infill 58).

Endothelial Coating, Seeding and Functionalization

Among other things, the present disclosure is directed to systems and methods for functionalizing and characterizing the inner walls of a complex, high-resolution, multi-planar vascular network of 3D-printed synthetic tissues using cell-specific ECM components aimed at instructing human umbilical vein endothelial cells (HUVECs) and/or for creating and maintaining an endothelialized vascular network for up to 21 days. The disclosed systems and methods can be used to functionalize surfaces of high-resolution 3-D printed constructs of synthetic origins with cell-specific ECM materials, by adopting a photo-reactive chemistry, including the ability to functionalize a complex multi-planar architecture of micron-scale channels, with extracellular matrix proteins of interest. The disclosed systems and methods enable the use of high resolution, high-fidelity printing methodologies (for example, via 3DS DLP printers FS10, FS20, and equivalents) in connection with methodologies that also enable cell-adhesion, thereby allowing for the generation of human-relevant data. When bioconjugated with the appropriate native ECM proteins, these vascularized tissues have applications that can include drug delivery, immuno-oncology, and in vitro modeling of drug-induced tissue injury, among other uses.

At a high level, the disclosed methods and systems may include providing a hydrogel or polymer chip, scaffold or vasculature network, coating the scaffold with ECM formulations via procedures to coat internal and external surfaces thereof, irradiating the coated surfaces to covalently bond the coating to the surfaces, seeding the coated surfaces with one or more bioactive coatings (i.e., acrylates), and irradiating the coated surfaces to enable functionalization of live cells thereon. Various assays can then be performed on the platform to mimic human in vivo conditions.

Figure 73:
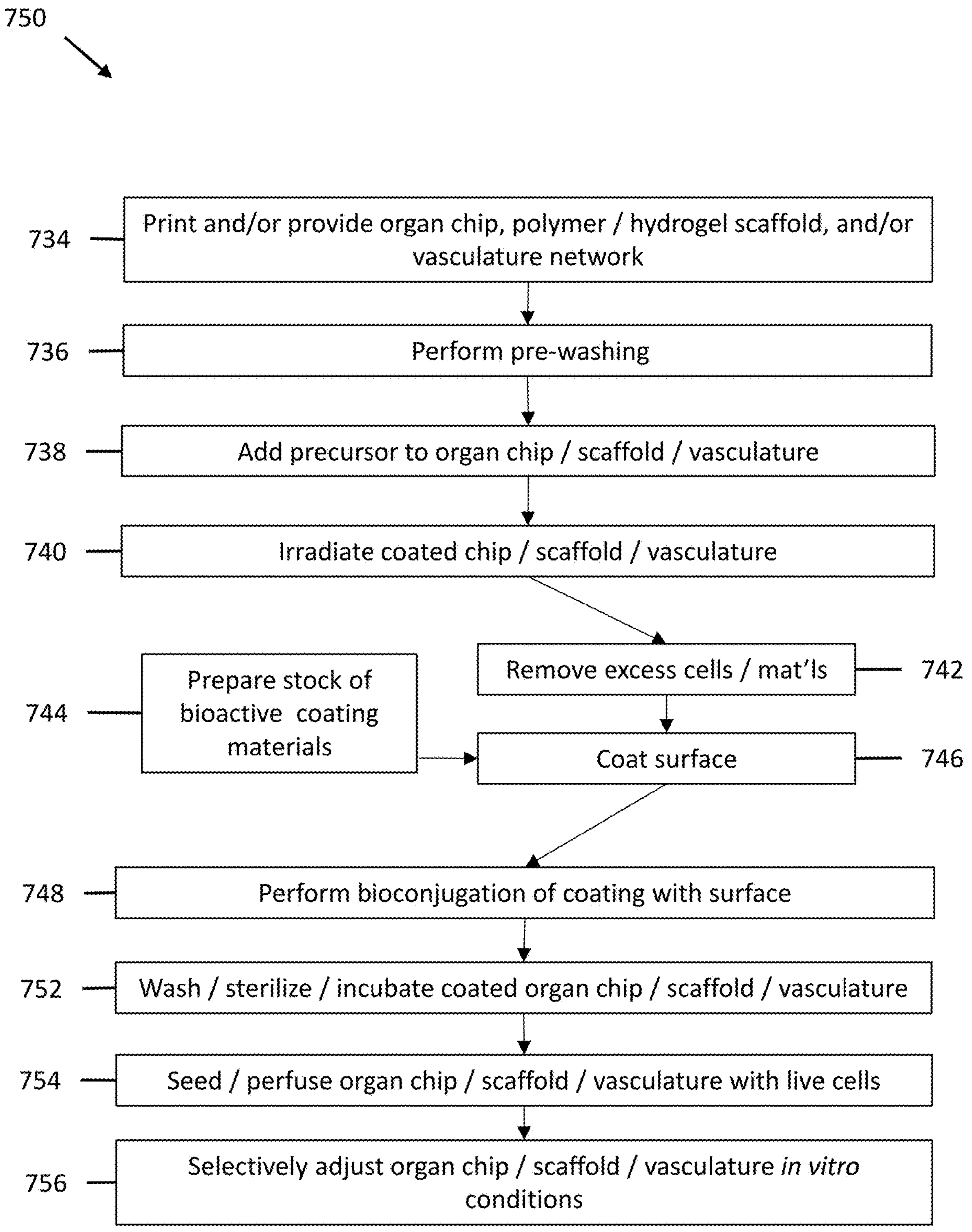
FIG. 73 illustrates a method of seeding and functionalizing a synthetic vascular network or other surface, according to aspects of the present embodiments.

The present disclosed methods can be used for functionalizing and characterizing the inner walls of a complex, high-resolution, multi-planar vascular network. FIG. 73 shows a method of coating surfaces of a complex, high-resolution, multi-planar vascular network, such that live cells may be functionalized thereon. At step 734, the method 750 may include printing the organ chip/scaffold/vasculature network as described herein. At step 736, the method 750 may include performing a pre-wash on the organ chip/scaffold/vasculature network. In some embodiments, step 736 may include briefly immersing (that is, for about 5 to about 10 seconds) on the organ chip/scaffold/vasculature network in a tub containing autoclaved Milli-Q at 37° C. to remove any excess bioink present on the print platform and on the surface any printed samples. In some embodiments, step 736 may be repeated one or more times. In some embodiments, step 736 may also include immersing any print samples, chips, etc. in autoclaved Milli-Q filled containers covered with foil to prevent undesired polymerization of unreacted acrylate groups due to stray light. In some embodiments, step 736 may include washing the chip/samples in autoclaved Milli-Q for 1 day and sterile DPBS for 1 day with media changes at least 3 times per day. At step 738, the method 750 may include adding precursor(s) to the organ chip/scaffold/vasculature network. In some embodiments, the precursor(s) may include acrylated-PEGTk-NHS (i.e., Acr-PEG-NHS). In some embodiments, the precursor(s) may include from about 1.5 mg/mL to about 4.0 mg/mL (for example, from about 2.0 mg/mL to about 3.5 mg/mL, from about 2.0 mg/mL to about 3.0 mg/mL, from about 2.25 mg/mL to about 2.75 mg/mL, and/or about 2.5 mg/mL) of Acr-PEG-NHS to 50 mM $NaHCO_3$. In some embodiments, precursor(s) may include from about 0.5% to about 3% of a water soluble, cytocompatible, photoinitiator (i.e., LAP).

Referring still to FIG. 73, at step 740, the method 750 may include irradiating the coated organ chip/scaffold/vasculature network/sample. In some embodiments, irradiating may include using an LED activated at a wavelength of 405 nm for about 5 to 15 minutes (i.e., about 8-12 minutes, i.e., about 10 minutes). In some embodiments, irradiating may include doing so for a sufficient period of time to covalently tether the precursor (i.e., Acr-PEG-NHS) to the surface of the organ chip/scaffold/vasculature network/sample. At step 742, the method 750 may include removing excess cells. In some embodiments, step 742 may include removing any excess Acr-PEG1k-NHS solution. At step 744, the method 750 may include preparing stock of one or more bioactive coatings (i.e., acrylates). In some embodiments, bioactive coatings (acrylates) may include GelMa, ColMA, collagen type 1 and/or acrylate-PEG. In some embodiments, preparation of ColMA stock may include: providing collagen methacrylate; making a 3 mg/mL stock using 100 mg of lyophilized ColMA and 33.3 mL of 20 mM acetic acid; manually shaking the mixture for about 2 hours (or until all of the collagen has dissolved and/or is no longer visible to the human eye); placing the mixture one ice intermittently to ensure the mixture does not exceed 4° C.; and placing the mixture in a refrigerator overnight to allow any bubbles to dissipate. In some embodiments, ColMA stock may include a concentration in a range from 50 μg/mL-200 μg/mL.

Referring still to FIG. 73, at step 746, the method 750 may include coating organ chip/scaffold/vasculature network with one or more bioactive coatings (i.e., acrylates). In some embodiments used in connection with bioconjugation of the surfaces with collagen type I, coating 746 may include adding about 10, 20, 100 or 200 μg/mL collagen-I to the surfaces and incubating for 2 hours at 37° C. followed by hydrating with water and sealing to prevent dehydration. In some embodiments used in connection with bioconjugation of the surfaces with ColMA, coating 746 may include adding a precursor solution containing ColMA 50, 100, or 250 μg/mL and from about 0.5% to about 3% of a water soluble, cytocompatible, photoinitiator (i.e., LAP) to the surfaces and incubating for 2 hours over ice, following by washing twice with PBS and irradiating at 405 nm for about 3-7 minutes (i.e., about 5 minutes). In some embodiments used in connection with bioconjugation of the surfaces with GelMA, coating 746 may include adding about 150 μL of precursor containing GelMA (in a weight percent range from about 2.5% to about 5%) and from about 0.5% to about 3% of a water soluble, cytocompatible, photoinitiator (i.e., LAP) to the surfaces and incubating for about 20-35 minutes (i.e., from about 25 to about 30 minutes) at 37° C., followed by hydrating and irradiating at 405 nm for 10 minutes (i.e., thereby covalently tethering GelMA to the hydrogel's surface via unreacted —$NH_2$ in the GelMA backbone and acrylate functionalization) as described herein. At step 748, the method 750 may include allowing bioconjugating of the bioactive coating to occur on the organ chip/scaffold/vasculature network surfaces. At step 752, the method 750 may include washing, sterilizing and/or incubating the bioconjugated organ chip/scaffold/vasculature network. In some embodiments, sterilization may include use of an ultraviolet light source activated at a wavelength of 254 nm for about 2 hours. In some embodiments, washing may include washing one or more times with PBS at a temperature range from about 37° C. to about 40° C. In some embodiments, incubation may include incubated for 2 hours at about 37° C. At step 754, the method 750 may include seeding and/or perfusing the surfaces and/or channels/flow passages/vasculatures/lumens with live cells, as described herein. At step 756, the method 750 may include selectively adjusting the in vitro conditions of the organ chip/scaffold/vasculature network according to the requirements of the assay being performed.

In some embodiments, cells (e.g., HepG2) attach to a functionalized surface (e.g., a surface having a thin coating of an acrylate such as GelMA, ColMA, acrylate-PEG) (as shown in FIGS. 52B, 53C, 53D, 54B, and 54C).

In some embodiments cells attach and migrate on a functionalized surface. In some embodiments, cells attach and divide (e.g., multiply) on a functionalized surface. In some embodiments, cells remain viable on a functionalized surface for at least 1 day, at least 3 days, at least 6 days, at least 7 days, at least 9 days, at least 12 days, at least 15 days, or at least 18 days.

In some embodiments, an interstitial space may for example, contain cells attached to a functionalized surface according to aspects of the present embodiments. For example, interstitial spaces, vasculatures, and other scaffolds or surfaces described herein may contain a functionalized surface with cells attached thereto.

In some embodiments cells attach to a functionalized surface of a vascular channel (e.g., lumen). In some embodiments, one cell (e.g., population of cells) attach to a functionalized surface of the interstitial space and a second cell (e.g., population of cells) attach to a functionalized surface of the vascular channel. In some embodiments, a cell can migrate across a functionalized surface. For example, a cell can migrate across a functionalized surface in response to a stimuli. Stationary cells or cells in migration can be visualized using microscopy and/or detection methods familiar to a skilled artisan.

In some embodiments, a medium (e.g., solution, buffer) can flow (e.g., be perfused) across a functionalized surface. For example, perfusing media across a layer of cells maintains viability of said cells. In some embodiments, a cell attached to a functionalized surface is selected from a group consisting of an endothelial cell, a biliary endothelial cell, a cholangiocyte, a liver parenchymal cell, a hepatocyte (HC), a primary human hepatocyte (PHH), a heptic stellate cell (HSCs), a Kupffer cell (KC), a liver sinusoidal endothelial cell (LSEC), a mucous cell, a parietal cell, a chief cell, an endocrine cell (e.g., a G cell, a D cell, a enterochromaffin cell, a EC-like cell, a X/A cell), a columnar epithelial cell, a cardiac fibroblast (CF), a cardiomyocyte, a smooth muscle cell, an enterocyte, a goblet cell, a Paneth cell, a stem cell, a neuron, a glia, a keratinocyte, a melanocyte, a Merkel cell, a Langerhan cell, a germ cell, a stromal cell, a seminiferous tubule, a Leydig cell, a tubule epithelial cell, a macula densa cell, a glomerular endothelial cell, a podocyte, a mesangial cell, a parietal epithelial cell, an immortalized cell (e.g. a 3T3 cell, a A549 cell, a HeLa cell, a HEK 293 cell, a HEK 293T cell, a Huh7 cell, a Jurkat cell, a OK cell, a Ptk2 cell, a Vero cell), a patient-derived cell (e.g., a tumor cell), a T cell, a peripheral blood mononuclear cell (PBMC), and/or an induced pluripotent stem cell (iPSC). In some embodiments, one cell type is attached to a functionalized surface. In some embodiments, multiple cell types are attached to a functionalized surface.

Figure 50A:
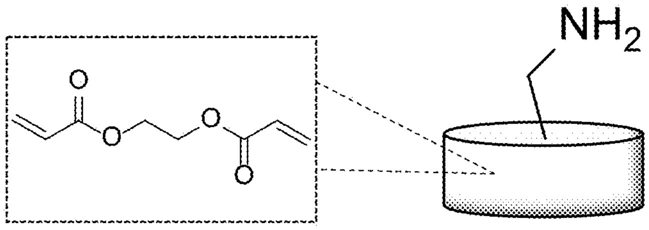
FIG. 50A is a diagram of an AN14 hydrogel having at least one amino group on a surface of the hydrogel, according to aspects of the present embodiments.
Figure 50B:
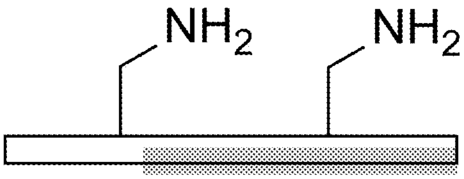
FIG. 50B is a diagram of a glass surface having a thin coating of 2.5% GelMA, according to aspects of the present embodiments.
Figure 50C:
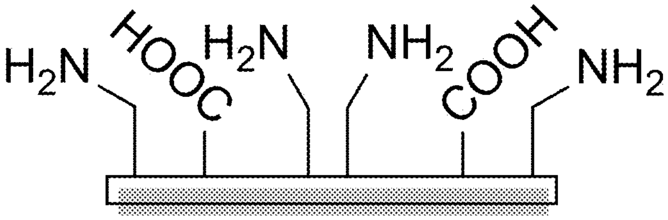
FIG. 50C is a diagram of a glass surface having a thin coating of 250 μg/ml ColMA, according to aspects of the present embodiments.

In some embodiments, an AN14 hydrogel containing polyethylene glycol diacrylate and gelatin methacrylate includes amino groups on a surface of the AN14 hydrogel that are capable of binding to a bioactive coating. FIG. 50A is a diagram of an AN14 hydrogel having at least one amino group on a surface of the hydrogel. In some embodiments, the AN14 hydrogel comprises less than 50% gelatin methacrylate, less than 40% gelatin methacrylate, less than 30% gelatin methacrylate, less than 25% gelatin methacrylate, less than 20% gelatin methacrylate, less than 15% gelatin methacrylate, less than 10% gelatin methacrylate, less than 5% gelatin methacrylate, or less than 3% gelatin methacrylate. In some embodiments, a functionalized surface is a glass surface that includes a coating of gelatin methacrylate ("GelMA") having amino groups capable of binding to a bioactive coating. FIG. 50B is a diagram of a glass surface having a thin coating of composed of 2.5% GelMA volume percent. The GelMA glass thin coating includes abundant amino groups on its surface. The GelMA glass thin coating is capable of intermolecular crosslinking with denatured collagen. In some embodiments, a GelMA glass thin coating has a degree of functionalization (DOF) of about 50%. In some embodiments, a functionalized surface is a glass surface that includes a coating of collagen methacrylate ("ColMA") having amino groups capable of binding to a bioactive coating. FIG. 50C is a diagram of a glass surface having a thin coating of 250 μg/ml ColMA. The ColMA glass thin coating includes amino groups on its surface and is capable of intermolecular crosslinking with fibrils. In some embodiments, the ColMA glass thin coating has a DOF of about 20%.

Figure 51A:
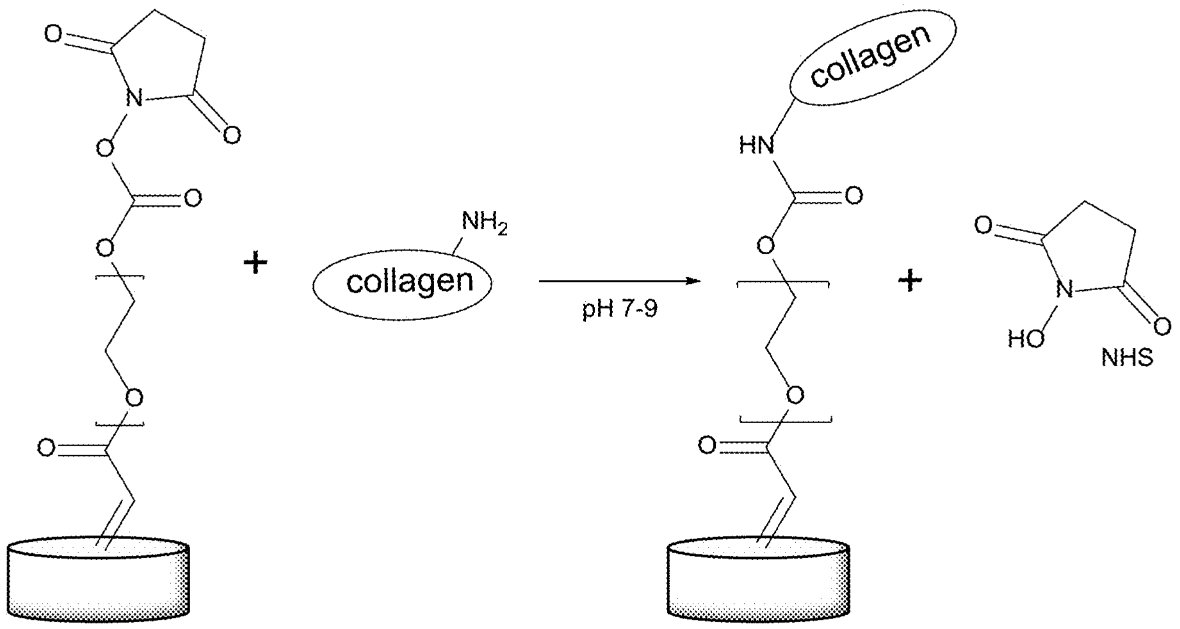
FIG. 51A is a diagram of a covalent linker incorporating an amine-reactive functional group tethered to a base polymer, according to aspects of the present embodiments.
Figure 51B:
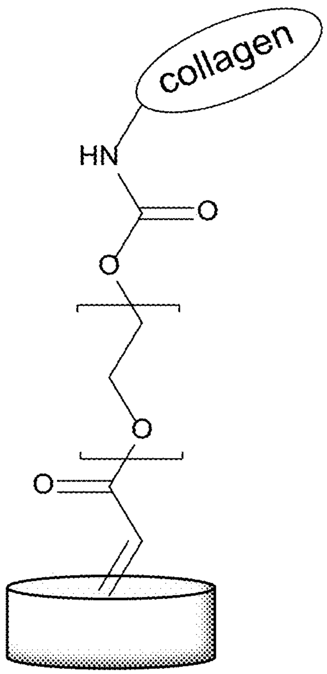
FIG. 51B illustrates an extracellular matrix (ECM) covalently bound to a base polymer via the covalent linker, according to aspects of the present embodiments.

In some embodiments, an acrylate-based hydrogel surface (e.g., a functionalized surface having a thin coating of an acrylate such as GelMA, ColMA, and/or polyethylene glycol diacrylate (PEGDA) is capable of binding to a bioactive coating within an extracellular matrix. In FIG. 51A, a covalent linker (e.g., GelMA, ColMA acrylate-PEG) incorporating an amine-reactive functional group (e.g., NHS) is tethered to a base polymer. The covalent linker is capable of reacting with an extracellular matrix ("ECM") protein (e.g., collagen). In some embodiments, the covalent linker reacts with an ECM protein at a pH of about 7-9. In this reaction, the protein forms a covalent bond with the covalent linker by replacing the amine-reactive functional group on the covalent linker. FIG. 51B shows the ECM covalently bound to a base polymer via the covalent linker.

Figure 52A:
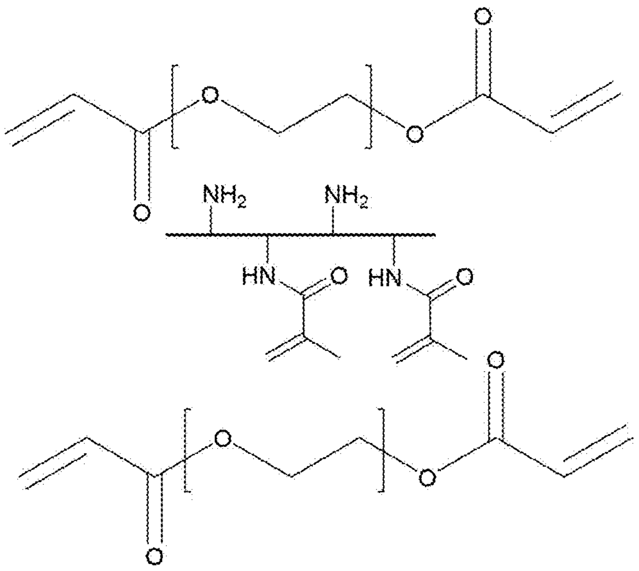
FIG. 52A shows a diagram of an AN14 hydrogel interacting with a bioactive coating, according to aspects of the present embodiments.
Figure 52B:
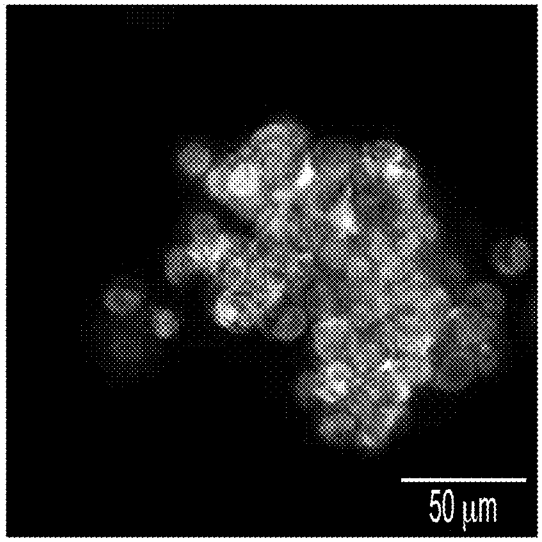
FIG. 52B depicts fluorescence images HepG2 attached to an A14 hydrogel that contains polyethylene glycol diacrylate and gelatin methacrylate (GelMA), according to aspects of the present embodiments.
Figure 53A:
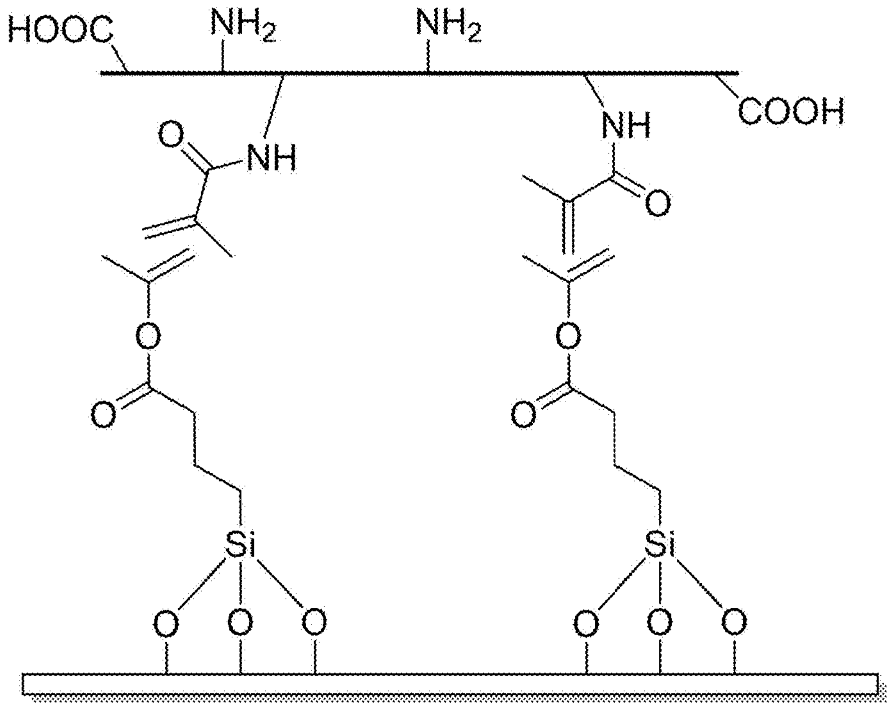
FIG. 53A illustrates a glass surface that is functionalized with a linker comprising an acrylate having a silyl group, according to aspects of the present embodiments.
Figure 53B:
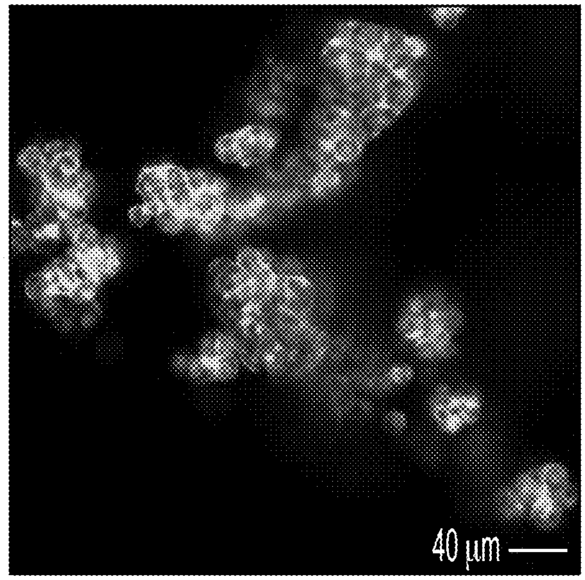
FIG. 53B shows a 2.5% GelMA glass thin coating having moderate fluorescence, according to aspects of the present embodiments.
Figure 53C:
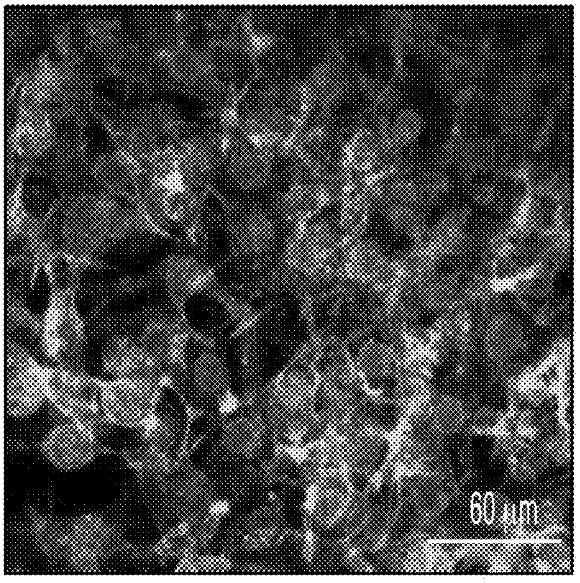
FIG. 53C shows a 250 μg/mL ColMA glass thin coating having moderate to high fluorescence, according to aspects of the present embodiments.
Figure 54A:
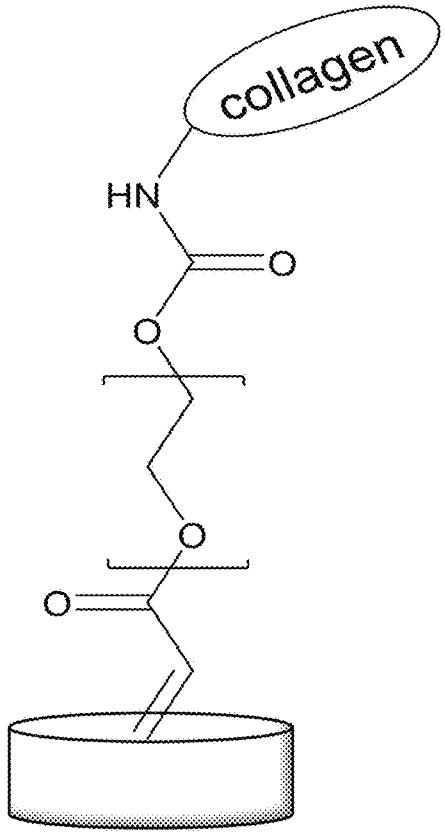
FIG. 54A shows a base polymer is functionalized with an acrylate that is covalently bound to a bioactive coating via photo crosslinking chemistry, according to aspects of the present embodiments.
Figure 54B:
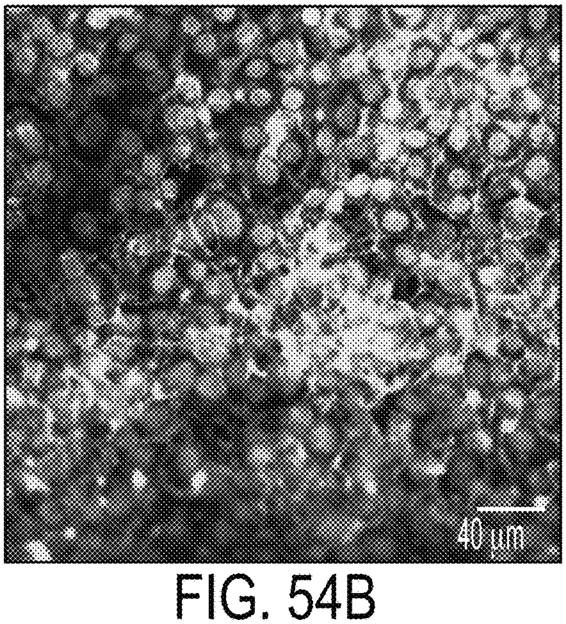
FIG. 54B shows the fluorescence of liver cancer cells attached to the functionalized base polymer at a concentration of 20 μg/ml of collagen, according to aspects of the present embodiments.
Figure 54C:
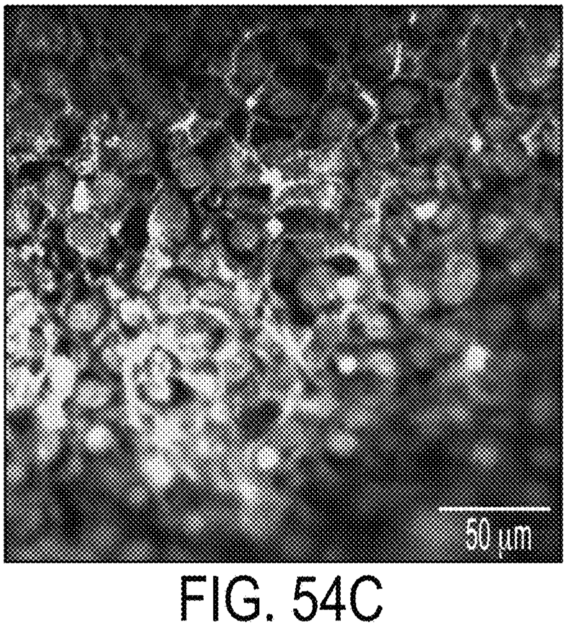
FIG. 54C shows the fluorescence of liver cancer cells attached to the functionalized base polymer at a concentration of 200 μg/ml of collagen, according to aspects of the present embodiments.
Figure 55A:
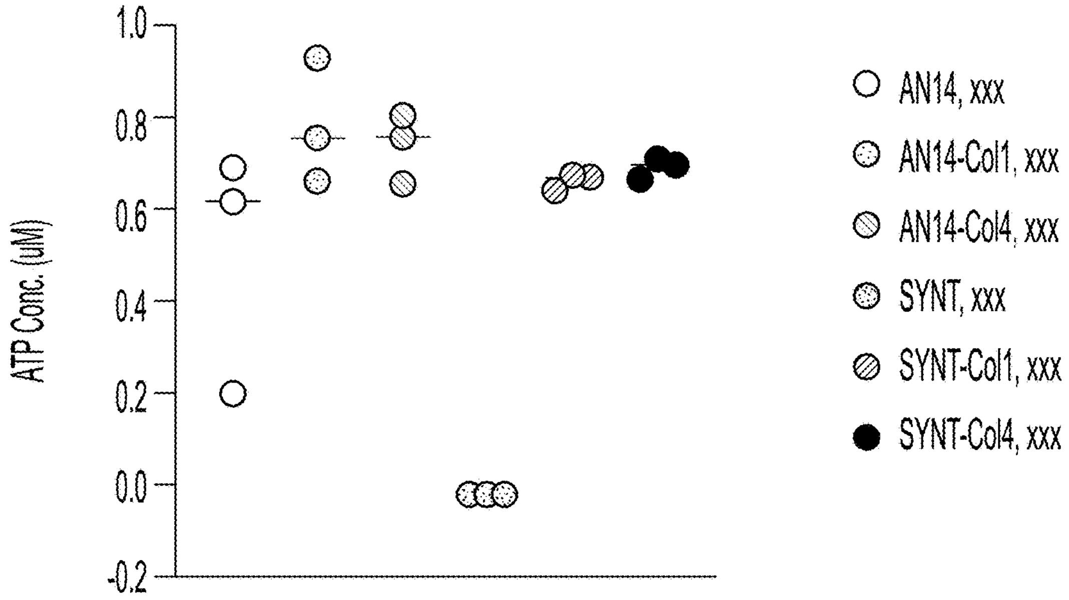
FIG. 55A is a dot plot depicting the results of an assay measuring ATP concentration of cells grown on surfaces described in FIGS. 45B-F, according to aspects of the present embodiments.
Figure 55B:
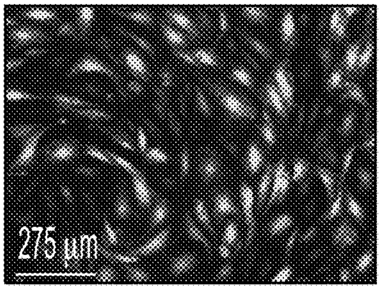
FIGS. 55B-F depict fluorescence microscopy images of HUVEC cells attached to coated and uncoated hydrogels, according to aspects of the present embodiments.
Figure 55C:
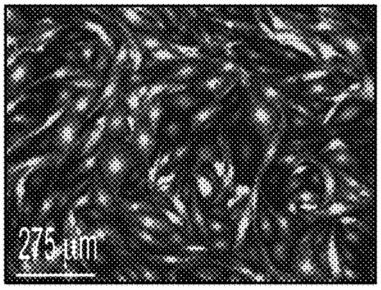
Figure 55D:
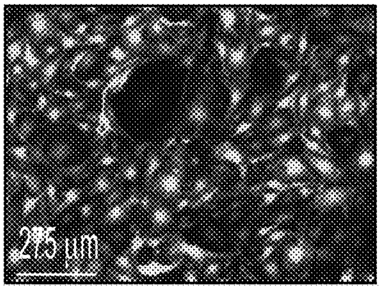
Figure 55E:
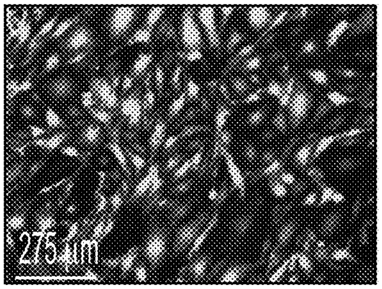
Figure 55F:
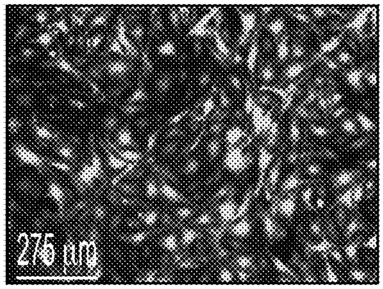
Figure 56A:
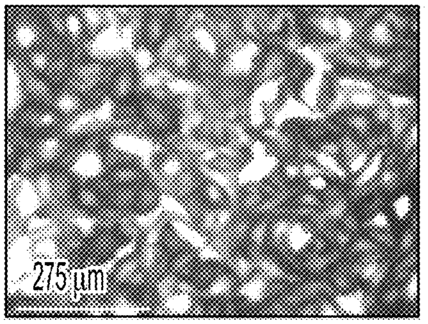
FIGS. 56A-C depict fluorescence microscopy images of HUVEC cells attached to a synthetic hydrogel containing PEGDA and coated with ECM proteins, on Days 1, 4, and 7, respectively, according to aspects of the present embodiments.
Figure 57A:
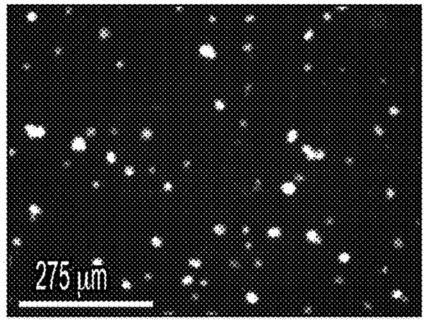
FIGS. 57A-C depict fluorescence microscopy images of HUVEC cells attached to a synthetic hydrogel containing PEGDA and not coated with ECM proteins, on Days 1, 4, and 7, respectively, according to aspects of the present embodiments.
Figure 56B:
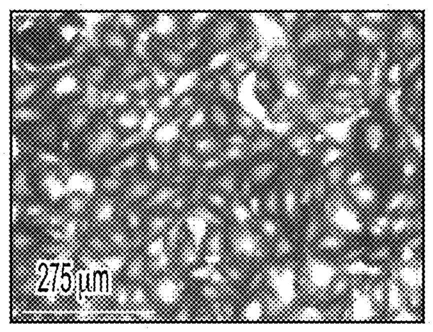
Figure 57B:
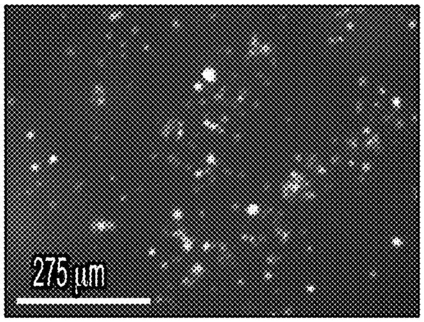
Figure 56C:
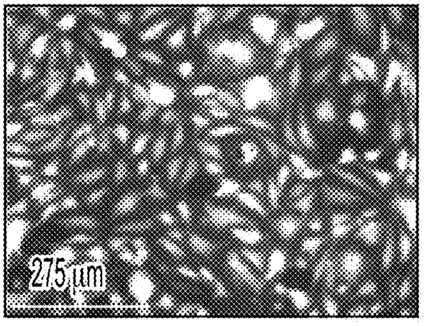
Figure 57C:
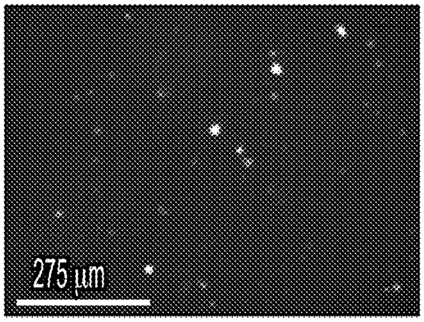
Figure 58:
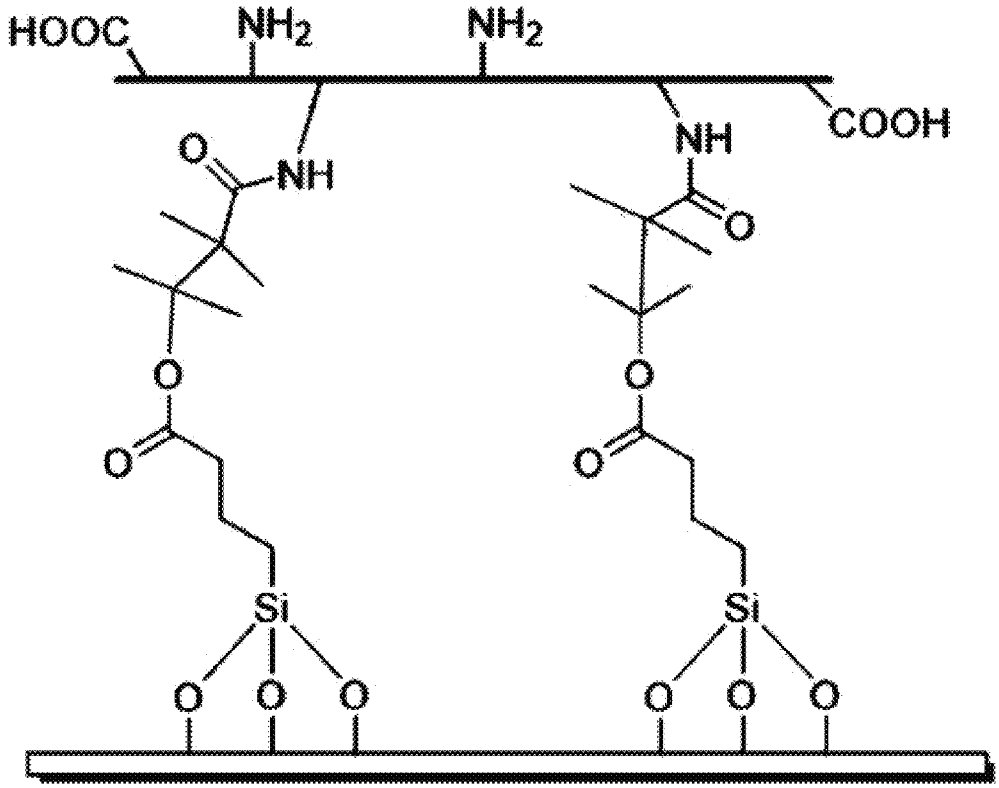
FIG. 58 illustrates the glass surface of 53A after functionalization, according to aspects of the present embodiments.
Figure 59A:
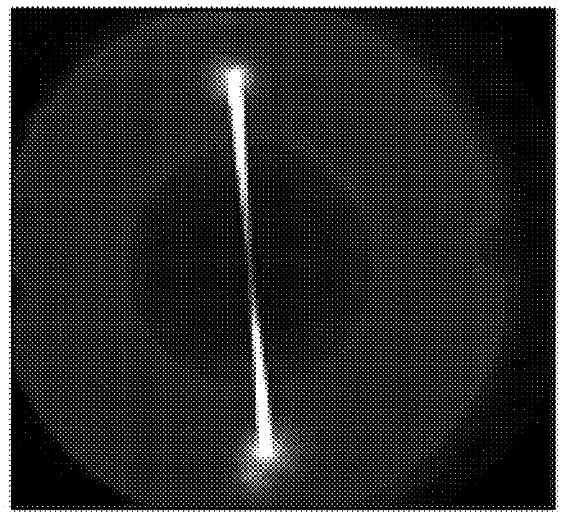
FIGS. 59A-B depict fluorescence microscopy images (24 h after seeding) of HUVEC cells attached to a 3-D printed lumen of ~200 μm diameter composed of a synthetic hydrogel (PEGDA-based) coated with ECM proteins, according to aspects of the present embodiments.
Figure 59B:
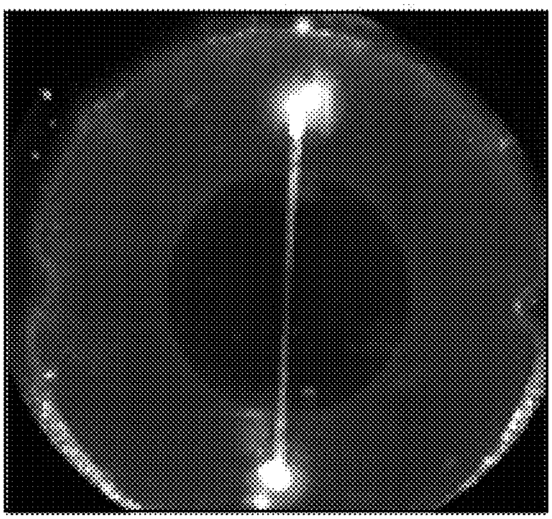
Figure 60A:
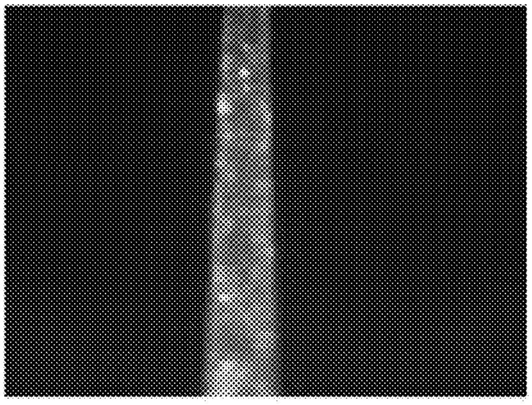
FIGS. 60A-B depict fluorescence microscopy images (4 h after seeding) of HUVEC cells attached to a 3-D printed lumen of ~200 μm diameter composed of a synthetic hydrogel (PEGDA-based) coated with ECM proteins.
Figure 60B:
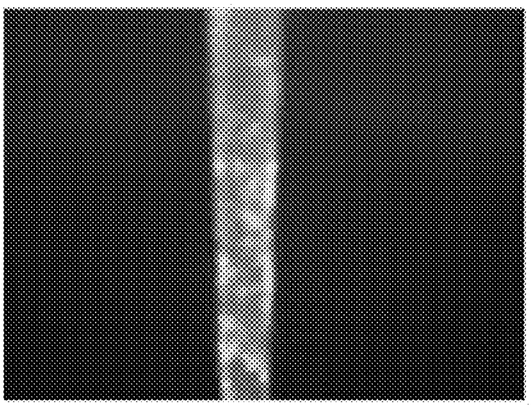
Figure 60C:
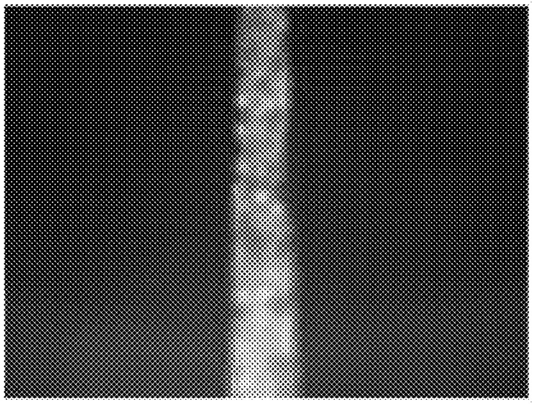
FIGS. 60C-D depict fluorescence microscopy images (4 h after seeding) of HUVEC cells attached to a 3-D printed lumen of ~200 μm diameter composed of a synthetic hydrogel (PEGDA-based) coated with ECM proteins.
Figure 60D:
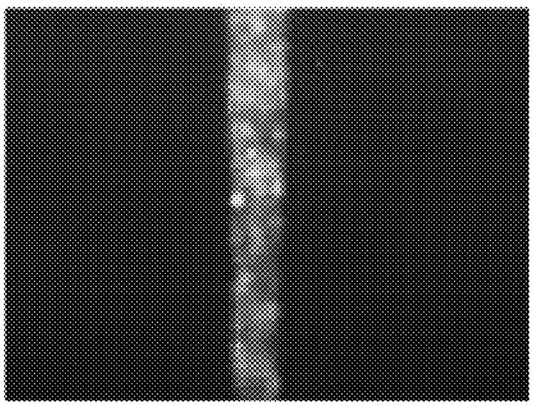
Figure 61A:
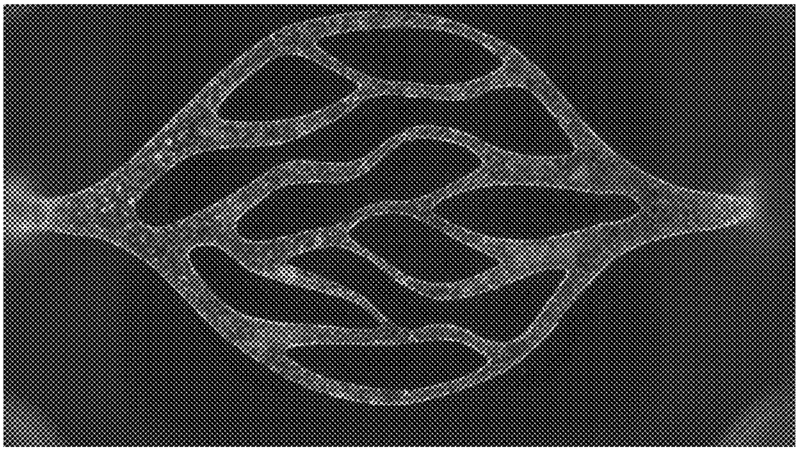
FIGS. 61A-61B depict endothelization of a structure described herein, according to aspects of the present embodiments.
Figure 61B:
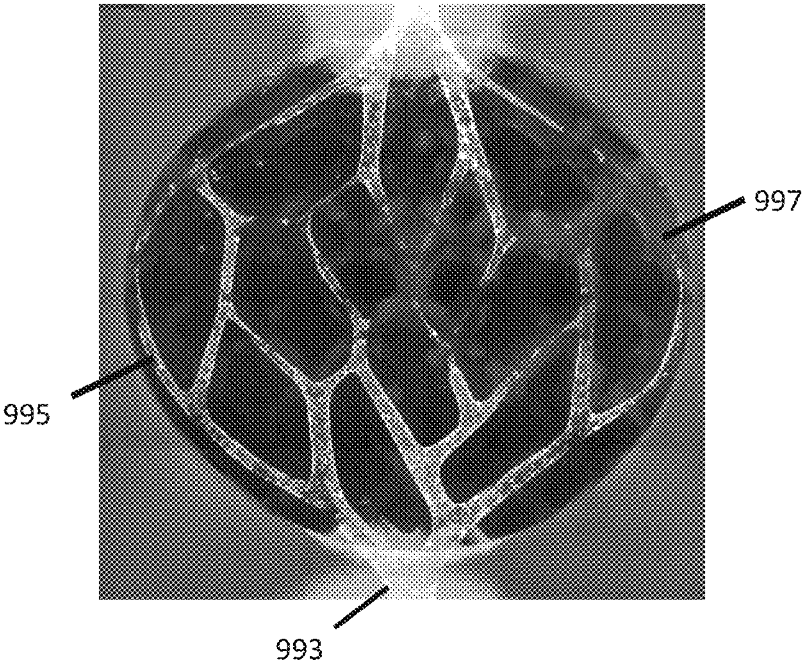

Embodiments of the present disclosure may bind cells to various surfaces through photoreactive chemistry. FIG. 52A shows a diagram of an AN14 hydrogel interacting with a bioactive coating. The bioactive coating is capable of binding to the amino groups on the hydrogel. FIGS. 52B, 53C, 53D, 54B, and 54C depict fluorescence images of liver cancer cells (HepG2) attached to various surfaces. HepG2 are imaged using fluorescence microscopy. HepG2 nuclei are stained in blue using DAPI and F-actin filaments are stained in green using Phalloidin. HepG2 cells are imaged day 1 after seeding on the surface. FIG. 52B depicts a fluorescence image of liver cancer cells attached to an AN14 hydrogel of the present disclosure through a bioactive coating. The fluorescence visible in FIG. 52B shows the AN14 hydrogel is capable of some cell attachment. In FIG. 53A, a glass surface is functionalized with a linker comprising an acrylate (e.g., GelMA, ColMA, polyethylene glycol diacrylate (PEGDA), etc.) having a silyl group. The silyl group of the acrylate is bound to the glass surface. The acrylate is capable of binding to a bioactive coating, thereby tethering the liver cancer cells to the functionalized glass surface via photoreactive chemistry. FIG. 58 illustrates the glass surface of 53A after functionalization. FIG. 53B shows a 2.5% GelMA glass thin coating having moderate fluorescence, indicating it is capable of moderate cell attachment. FIG. 53C shows a 250 μg/mL ColMA glass thin coating having moderate to high fluorescence, indicating a capability for moderate to high cell attachment. In FIG. 54A, a base polymer is functionalized with an acrylate (e.g., acrylate-PEG1k-NHS) that is covalently bound to a bioactive coating via photocrosslinking chemistry. In some embodiments, the base polymer is an AN14 hydrogel. In some embodiments, the bioactive coating is or comprises collagen ECM proteins. FIG. 54B shows the fluorescence of liver cancer cells attached to the functionalized base polymer at a concentration of 20 μg/ml of collagen, the attached liver cells having high fluorescence. FIG. 54C shows the fluorescence of liver cancer cells attached to the functionalized base polymer at a concentration of 200 μg/ml of collagen, the attached liver cells having high fluorescence. FIGS. 54B and 54C indicate that a functionalized base polymer of the present disclosure is capable of high cell attachment.

Coating Solutions & Formulations

According to aspects of the present disclosure, bioactive coatings may be used to encourage cell growth and binding to scaffold/vasculature surfaces. In some embodiments, coating solutions and formulations may include collagen type I, collagen type IV, fibronectin, and/or DPBS (1×) (that is, Dulbecco's Phosphate Buffered Saline (DPBS) 1×, or equivalent PBS). In some embodiments, coating solutions and formulations may include different relative amounts of these constituents depending on if the surface being coated is two-dimensional (2D) or includes a three-dimensional geometry (for example, 3D vasculatures and/or other three-dimensional scaffolds). Without wishing to be bound by theory, it is contemplated that a higher relative volume content of fibronectin may be beneficial when coating three-dimensional geometries (i.e., as compared to two-dimensional geometries) in order to promote binding and/or adhesion of bioactive cells with the surface, scaffold, and/or geometry being coated.

Table 1 below shows nominal volume per 1000 μL and corresponding volume percents for each of the four coating constituents (collagen type I, collagen type IV, fibronectin, and/or DPBS (1×)) for 2D surfaces and 3D surfaces/geometries. As can be seen in Table 1, fibronectin is present in a much higher volume percent in coatings used for 3D surfaces/geometries than in coatings used for 2D surfaces.

TABLE 1

Coating constituents for 2D and 3D surfaces

| | 2D surfaces | | 3D geometries | |
|---|---|---|---|---|
| | Vol (μL) /1000 μL | Volume Percent | Vol (μL) /1000 μL | Volume Percent |
| Col I | 4.2 | 0.42% | 47.3 | 4.73% |
| Col IV | 88.0 | 8.80% | 268.4 | 26.84% |
| Fibronectin | 44.0 | 4.40% | 671.1 | 67.11% |
| DPBS (1X) | 863.8 | 86.38% | 13.2 | 1.32% |

Tables 2 and 3 below show nominal, approximate minimum and approximate maximum volume percents for each of the four coating constituents, for 2D surface coatings and 3D surface coatings respectively. Accordingly, bioactive coatings of the present disclosure may include collagen type I in a range from about 0.2% to about 8.0%, collagen type IV in a range from about 4% to about 40%, fibronectin in a range from about 2% to about 90%, and DPBS (1×) in a range from about 0.5% to about 95%. Each of the constituents shown in Tables 1-3 may be present at concentrations equal to, or approximately equal to, their respective stock concentrations, prior to mixing with the other constituents.

TABLE 2

Nominal, minimum and maximum coating constituents for 2D surfaces

| | 2D surfaces | | | |
|---|---|---|---|---|
| | Vol (μL) /1000 μL | Nom. Vol. % | Min Vol. % | Max Vol. % |
| Col I | 4.2 | 0.42% | 0.2% | 0.6% |
| Col IV | 88.0 | 8.80% | 4.0% | 13.0% |
| Fibronectin | 44.0 | 4.40% | 2.0% | 7.0% |
| DPBS (1X) | 863.8 | 86.38% | 50.0% | 95.0% |

TABLE 3

Nominal, minimum and maximum coating constituents for 3D surfaces

| | 3D geometries | | | |
|---|---|---|---|---|
| | Vol (μL) /1000 μL | Nom. Vol. % | Min Vol. % | Max Vol. % |
| Col I | 47.3 | 4.73% | 2.3% | 8.0% |
| Col IV | 268.4 | 26.84% | 12.0% | 40.0% |
| Fibronectin | 671.1 | 67.11% | 35.0% | 90.0% |
| DPBS (1X) | 13.2 | 1.32% | 0.5% | 3.0% |

Preparation of Materials

Bis-NHS-PEG: The preparation may begin with dissolving stock material in an alkaline buffer, followed by applying a sterile filter. Afterwards, the solution is added to the hydrogel well and allowed a period of five minutes for adsorption to occur. Subsequently, the excess is removed, and the solution is washed with DPBS. Next steps include a collagen-I coating, followed by an incubation in 37° C. for two hours. Lastly, the solution is washed with DPBS and Cell seeding is performed.

Acr-PEG1k-NHS: The preparation may begin with dissolving stock material in an alkaline buffer and adding PI, followed by applying a sterile filter. Afterwards, the solution is added to the hydrogel well and allowed a period of five minutes for adsorption to occur. Subsequently, the excess is removed, and the solution is washed with DPBS. Next steps include a collagen-I coating, followed by an incubation at 37° C. for two hours. Lastly, the solution is washed with DPBS and cell seeding is performed.

ColMA: The preparation may begin with a 3 mg/mL stock in sterile acetic acid. Next, a dilution is made using sterile DPBS on ice. Afterwards, PI is added and gently shaken until dissolved, followed by a sterile filter. Subsequently, samples are added (on ice) and covered with foil. Next steps include an incubation in 37° C. for two hours, followed by irradiating using a 405 nm LED box for a period of 10 minutes. Lastly, the solution washed with DPBS and cell seeding is performed.

GelMA: The preparation may begin with a 20% sterile stock, filtered in PBS. Next, a dilution is made using sterile DPBS, and PI is added. Afterwards, a sterile filter is applied, followed by placing back in warming bath. Subsequently, samples are added and covered with foil. Next step includes irradiating using a 405 nm LED box for a period of 10 minutes. Lastly, the solution washed with DPBS and cell seeding is performed.

PDA: The preparation may begin with dissolving DH at basic pH, followed by a sterile filter. Subsequently, inner chamber is coated. Lastly, PDA is washed with PBS and cell seeding is performed.

TMSPMA: The preparation may begin with glass bottom plates washed in a detergent and sonicated in Milli-Q. Next steps include plasma activation, followed by addition of $HCL/H_2O_2$. Afterwards, toluene is added to the solution and treated for a period of two hours. Subsequently, the solution is washed in EtOH, dried in a fume hood, and stored at Store at 4° C. until use, when desired amounts of colMA/GelMA and PI are added. Next step includes irradiating using a 405 nm LED box for a period of 10 minutes, followed by irradiation at 254 nm to sterilize.

Transendothelial Migration (TEM)

Organ-on-a-chip platform is considered the most promising substitute for conventional animal model-based drug discovery approach in pharmaceutical industry. The endothelialization of tissue modeling to achieve a more in vivo-like organ and/or tissue structure has become more significant in the tissue engineering field, and therefore introduction of highly engineered endothelial layer to in vitro tissue modeling may render organ on-a-chip-based drug discovery more desirable by the pharmaceutical industry. In addition, due to increased interest in immune therapy for cancer treatment, transendothelial migration (TEM) of immune cells to tumor tissue is extensively researched in academia and industry. Consequently, development of in vitro models that can realistically recapitulate TEM is highly desirable. Conventional microphysiological systems (MPS) for TEM studies exhibit imitations such as difficultly to apply to 3D tissue modeling, randomly distributed vasculatures resulting in poor connectivity and short culturing periods, as well as complicated fabrication methods. To overcome these challenges, a scalable fabrication method is disclosed for construction of MPS including in vitro 3D vascularized tissue structures interfaced with endothelial conduits for TEM studies.

In some embodiments, a full-scale vasculature microfluidic channel is constructed to recapitulate an in vivo vascularized tissue environment in a more reproducible manner. The vasculature microfluidic channel, for example, is superior to conventional angiogenesis-based methods which result in random vascularization. In some embodiments, the vasculature microfluidic channel includes micropores to maximize the interfacing area between an endothelial layer and epithelial and/or tumor tissue. In some embodiments, a covalent bonding-based biochemical surface modification approach is used to incorporate bio-compatible and bioactive molecules on a surface of vasculature channel and surface surrounding interstitial space, to achieve an in vivo-like tissue environment in a physio-chemically stable manner.

MPS Model

In some embodiments, a MPS platform may be constructed using a highly biocompatible, O2-permeable and nutrient-permeable hydrogel via a simple and scalable 3D printing approach. In some embodiments, a MPS platform may include a micro-scaled interstitial space and a branched microfluidic channel. An interstitial space may be loaded with an ECM hydrogel to achieve 3D epithelial tissue and/or tumor tissue formation. A branched microfluidic channel may include an endothelial cell layer to form a vasculature lumen structure, through which cell culture media and/or immune cells may be introduced to mimic the in vivo circulation condition.

In some embodiments, surface of interstitial space and vasculature channel may be functionalized with protein-reactive chemical moiety to immobilize ECM hydrogel and ECM protein with robust physical stability. An interstitial space surface, for example, may incorporate an amine-reactive functional group (e.g., N-hydroxysuccinimidyl ester; NHS) via covalent bonding to allow mechanically stable immobilization of ECM hydrogels such as Matrigel and GelTrex. A vasculature channel, for example, may include an ECM protein (e.g., Collagen, Fibronectin and/or Gelatin)-reactive surface to promote the endothelial cell layering. An ECM protein-reactive surface may include NHS, poly-L-Lysine, thiolated gelatin, thiolated heparin, Thiolated hyaluronic acid and/or thiolated collagen.

In some embodiments, microscale pores may be introduced along a 3D microfluidic channel to facilitate a three-dimensional interface between the interstitial space and an endothelial layer. The micropores may serve as a conduit for the therapeutics or immune cells (for example, T-cells) to migrate through the endothelial cell layer and a soft hydrogel extracellular matrix (Matrigel) into the interstitial space containing tumor cells or tumoroids. The cells, however, cannot migrate through vasculature walls. The hydrogel material used for the vasculature walls selectively permeable to molecules lower than ~10 kDa.

In some embodiments, the micropores may be monolithic with the rest of the vasculature, i.e., the same printing process and material properties is used, however, slightly different dosages may be implemented to print finer details. In some embodiments, the micropores may be printed using light-based DLP 3D printing technology, such as FS-series of bioprinters offered by 3D Systems, or BioNanoOne, a 2 photon 3D DLP technology offered by UpNano. In some embodiments, design with micropores may be printed using FS-10. The FS-10 may include a pixel size of 10 μm, and therefore provides a practical printing resolution of 30 μm. Conventional methods of introducing pores in a Transwell may include creation of a master mold.

In some embodiments, a 3D vasculature channel that is perfused with media via a syringe pump system, may allow epithelial tissue and endothelial cell layer to be cultured for longer time (e.g., at least 3 weeks) while maintaining high tissue functionality. An endothelialized vasculature may create a native barrier possessed by a blood vessel. Perfusion of media through this vessel provides nutrients and oxygen to the cells forming the barrier (for example, endothelial cells). Additionally, flowing immune cells through vasculature introduce an additional level of complexity to the MPS model wherein these cells need to permeate across the barrier, travel through the microporous channel to invade the tumor in the interstitial space.

In some embodiments, a MPS model may include one inlet and one outlet, allowing one therapeutic to be perfused through the entire system. In some embodiments, a MPS model may be modified for targeted delivery of therapeutics to localized regions.

Figure 47A:
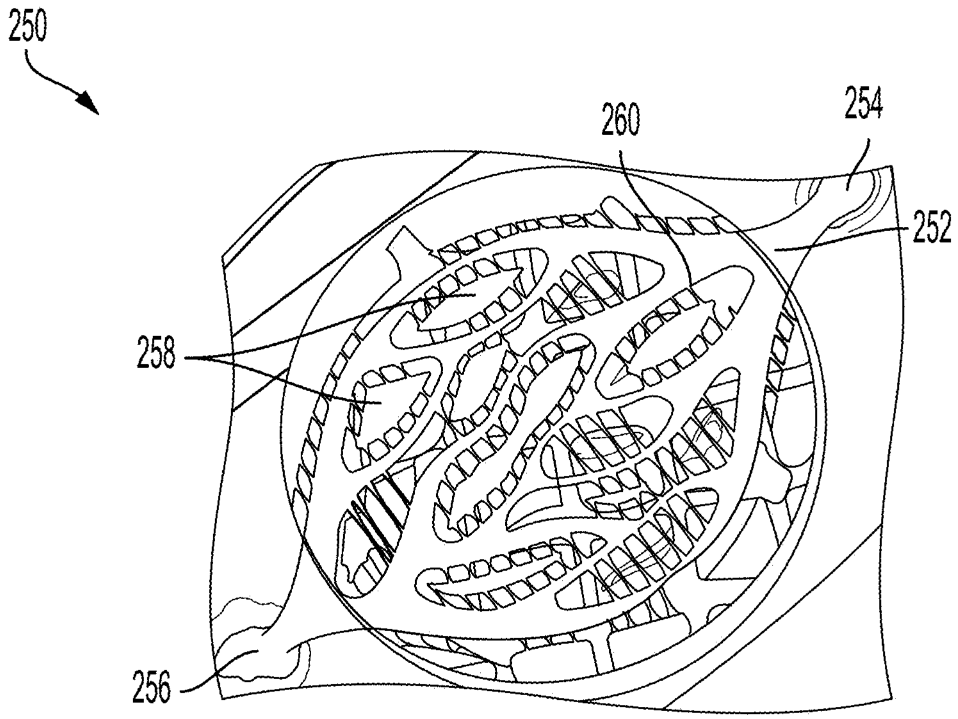
FIG. 47A is an image of a MPS platform structure including an inlet, an outlet, a vasculature microfluidic channel, interstitial spaces and micropores connecting vasculature channel and interstitial spaces, according to aspects of the present embodiments.
Figure 47B:
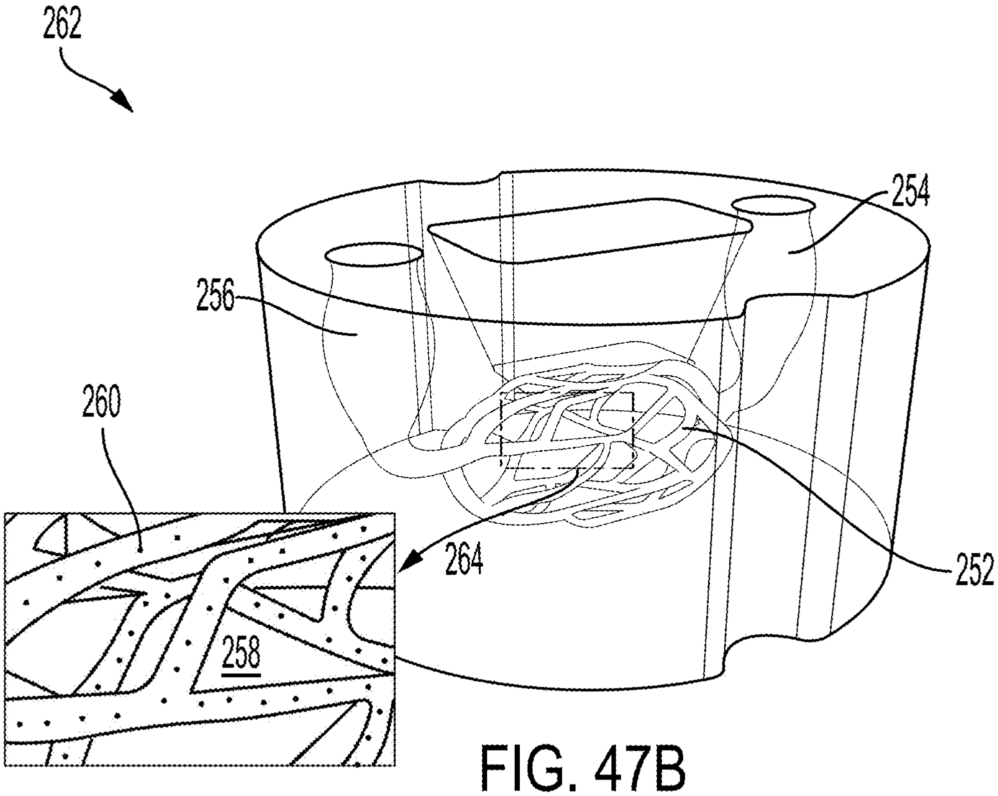
FIG. 47B illustrates a three-dimensional chip organ, according to aspects of the present embodiments.

In some embodiment, a MPS model includes a large-scale vasculature network with micropores connecting endothelial layer in a channel and epithelial (or tumor) tissues in interstitial space. FIG. 47A is 2D image of a MPS platform structure 250 including an inlet 254, an outlet 256, a vasculature microfluidic channel 252, interstitial spaces 258 and micropores 260 connecting vasculature channel 252 and interstitial spaces 258. The MPS platform structure 250 may be expanded three-dimensionally into a chip organ 262 to recapitulate a 3D in vivo tissue, as show in FIG. 47B. The chip organ 262 may include an inlet 254, an outlet 256, vasculature 252. A closeup area 264 shows the micropores 260 connecting vasculature channel 252 and interstitial spaces 258. In some embodiments, the micropores 260 may include a diameter of about 40 μm to about 60 μm. In some embodiments, the number of micropores 260 is directly proportional to the surface area of the vasculature channel 252. For example, a channel with a surface area of X $cm^2$ may include X number of micropores 260 (for example, one micropore per unit area). The length of the micropores 260 is determined by the thickness of a vasculature channel wall. In some embodiments, the micropores 260 may include a length of 100 μm. In some embodiments, the micropores 260 may include a length of 150 μm. In some embodiments, the micropores 260 may include a length of 200 μm.

In some embodiments, a MPS platform enables evaluation of key functions of immune cells including activation of immune cells by an external agent, migration of immune cells from vasculature into a tissue compartment, and interaction of immune cells with a tissue. When immune cells (e.g., T-cells) are activated by an immunotherapeutic agent (e.g., a peptide, an antibody-based agent), the immune cells move into a tissue compartment (for example a tumor) and activities within interstitial space may be monitored. In some embodiments, a MPS platform may be used in development of cancer therapy. Cancer treatments, for example, focus on killing tumor cells (i.e., cancerous cells) without damaging the surrounding healthy cells. Immune cells, however, may exhibit exhaustion due to lack of nutrients and/or oxygen, and therefore become unable to kill tumor cell. A MPS platform may be used to evaluate the ability of activated immune cells in killing tumor cells. In some embodiments, a MPS platform may be used in development of gene therapies (for example, mRNA in lipid nanoparticles) that are drained by liver. A MPS platform may assess whether therapeutic agents reach a tissue of interest, and/or there is drainage from vasculature into other organs, and thus, enabling evaluation of delivery and efficacy of gene therapies. In some embodiments, a MPS platform may be used to assess safety of vascular delivery of therapeutic agents. Some therapeutic agents, not only kill surrounding healthy tissue of a tumor cell, but they may also kill vascular tissue cells during delivery. And therefore, requiring further assessments to ensure safe vascular delivery.

In some embodiments, immune cells may be perfused through a vasculature and migrate into the tumor compartment in the interstitial space. Unattached or free immune cells may either be collected by washing the vasculature or by collecting the medium in the interstitial well. In some embodiments, immune cells are recruited by the tumor compartment, and therefore can be isolated by digesting the Matrigel using digestion reagents, such as organoid harvesting solution and cell recovery solutions. In some embodiments, the immune cells are recruited to the endothelial cells lining the vasculature, and therefore may be dissociated from the hydrogel scaffold by perfusing dissociation reagents, such as trypsin and Accutase. The trypsinized cells may further be processed and analyzed for protein or RNA quantification.

In transendothelial migration experiments, destination of immune cells is interstitial space where tumoroids and Matrigel are located. In some embodiments, a portion of migrated immune cells may escape the Matrigel layer, reaching the media. The immune cell fractions may be collected from the media, and the phenotype can be efficiently analyzed and classified by FACS. In some embodiments, a fraction of migrated immune cell fractions may be collected by scraping Matrigel in the interstitial space.

MPS Construction

Figure 62:
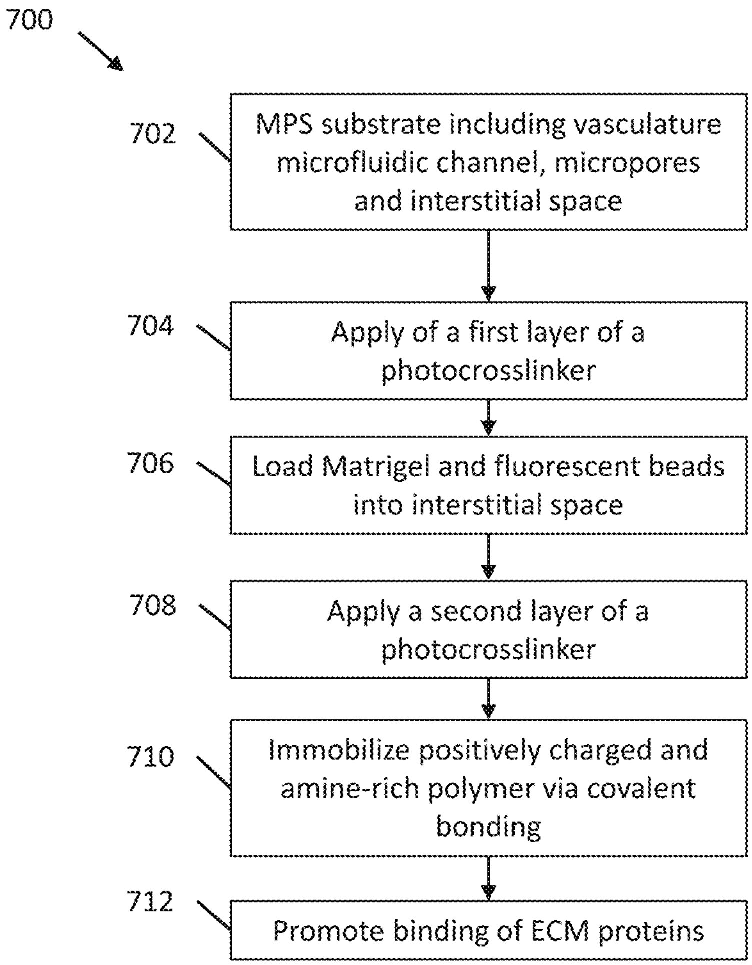
FIG. 62 is a flowchart of a construction method of Endothelial/epithelial interfacing MPS model, according to aspects of the present embodiments.

In some embodiments, MPS construction includes an ECM coating approach using a positively charged polymer. A covalent bonding (e.g., amide bonding)-based biochemical conjugation technique may allow stable bioconjugation of biomaterial (for example, ECMs and ECM-derived hydrogels) to the surface of MPS substrate. FIG. 62 is a flowchart of a construction method 700 of Endothelial/epithelial interfacing MPS model. At step 702, the method 700 may include a MPS substrate including vasculature microfluidic channel, micropores and an interstitial space. At step 704, the method 700 may include applying a first layer of a photo crosslinker (for example, by a SVA treatment) to functionalize the surface of MPS substrate through amine-reactive chemical moieties. At step 706, the method 700 may include loading Matrigel and fluorescent beads into the interstitial space. The protein fraction of Matrigel may covalently adhere to the surface of MPS substrate which is activated by amine-reactive groups. The Matrigel may fill the micropores which renders the vasculature channel operational (i.e., the microfluidic channel is completed when micropores are closed). At step 708, the method 700 may include applying a second layer of a photo crosslinker (for example, through a SVA treatment) to the vasculature microfluidic channel to achieve a second surface modification (amine-reactive activation). At step 710, the method 700 may include immobilizing a positively charged and amine-rich polymer, for example, poly-L-Lysine (PLL) via covalent bonding (such as amide bond formation). At step 712, the method 700 may include promoting, by the immobilized PLL, the binding of ECM proteins such as fibronectin via electrostatic interaction between positively charged PLL-surface and negatively charged fibronectin under physiological pH condition.

Figure 48A:
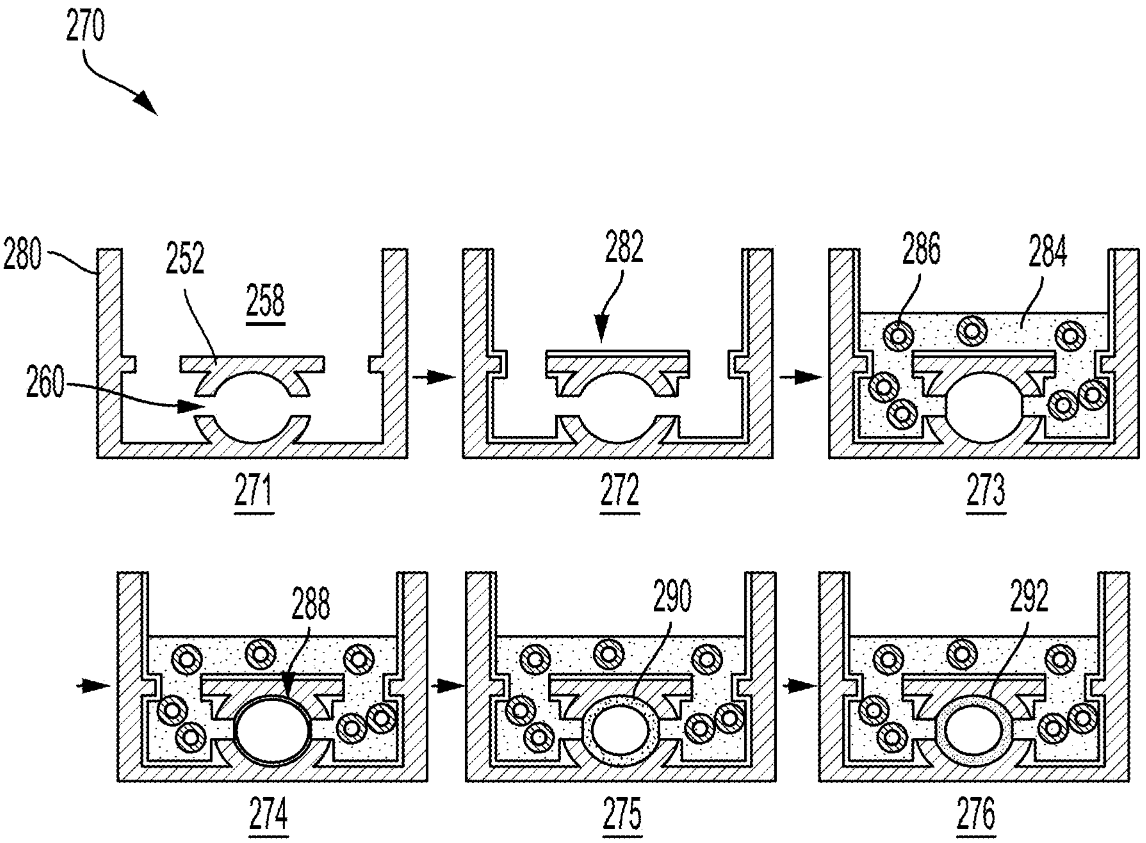
FIG. 48A is a schematic of a construction method of Endothelial/epithelial interfacing MPS model, according to aspects of the present embodiments.
Figures 48B, 48C, 48D, 48E:
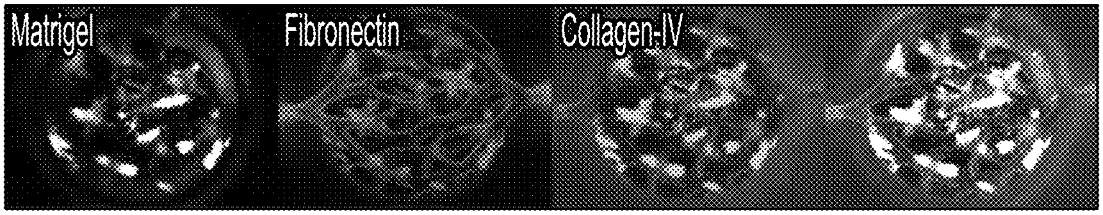
FIG. 48B is an exemplary image of Matrigel in a MPS model, according to aspects of the present embodiments.
FIG. 48C is an exemplary image fibronectin in a MPS model, according to aspects of the present embodiments.
FIG. 48D is an exemplary image of collagen-IV in a MPS model, according to aspects of the present embodiments.
FIG. 48E is an exemplary image ECM-coated transendothelialization MPS model, according to aspects of the present embodiments.
Figure 48G:
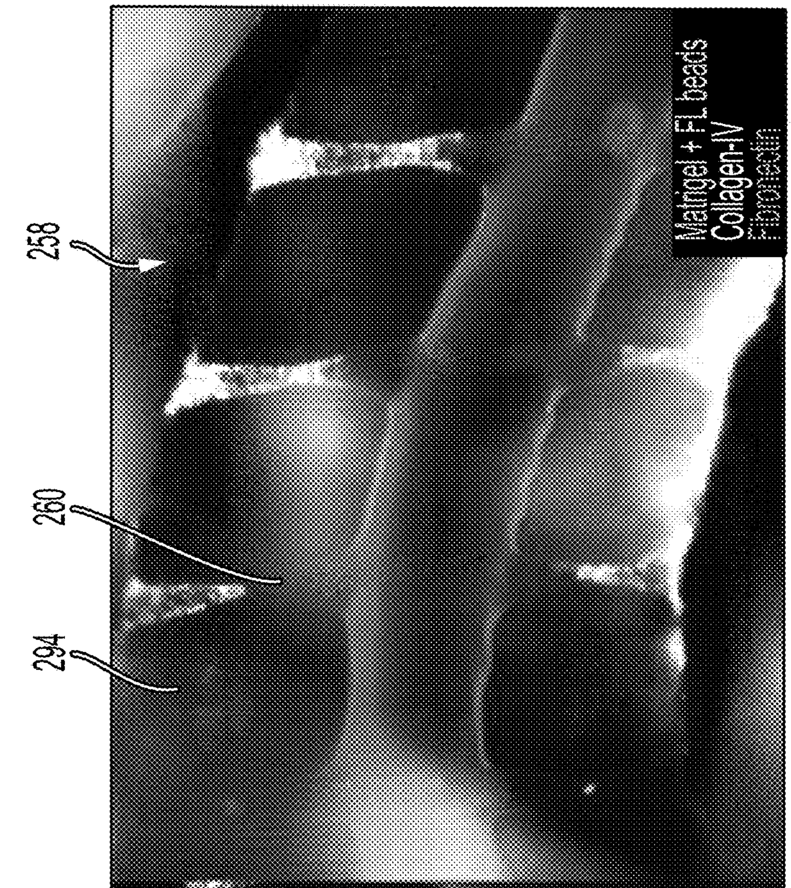
FIGS. 48F and 48G are images of vasculature channels, channel walls, micropores, and interstitial spaces, according to aspects of the present embodiments.
Figure 48F:
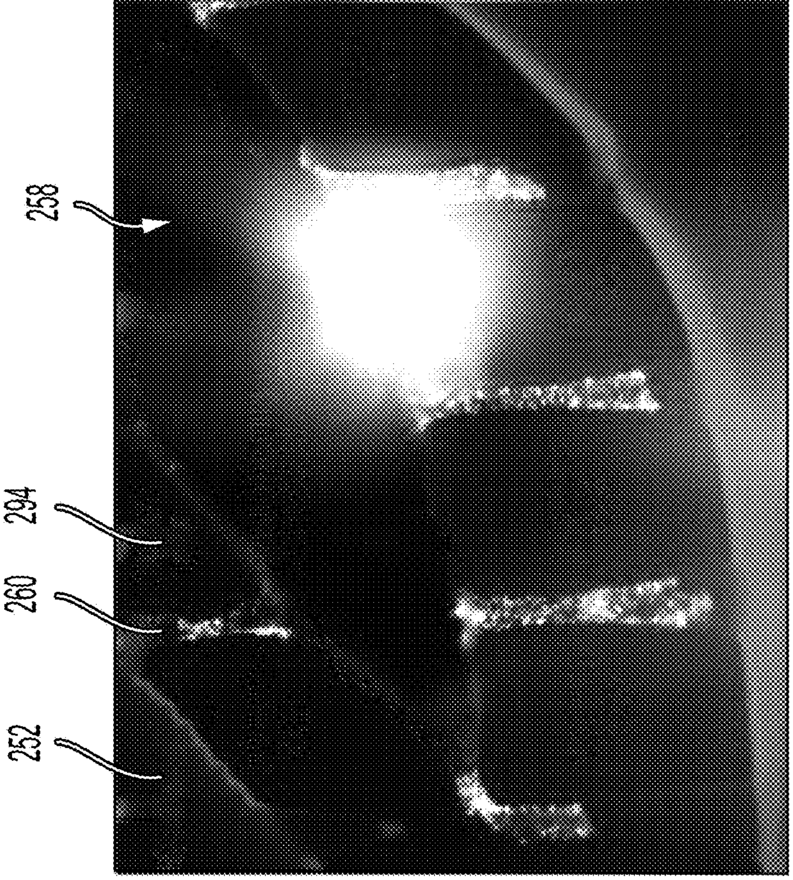

FIG. 48A is a schematic of a construction method 270 of Endothelial/epithelial interfacing MPS model. At step 271, the method 270 may include a MPS substrate 280, vasculature microfluidic channel 252, micropores 260 and an interstitial space 258. At step 272, the method 270 may include applying a first layer of a photo crosslinker 282 (for example, by a SVA treatment) to functionalize the surface of MPS substrate 280 through amine-reactive chemical moieties. At step 273, the method 270 may include loading Matrigel 284 and fluorescent beads 286 into the interstitial space 258. The protein fraction of Matrigel 284 may covalently adhere to the surface of MPS substrate 280 which is activated by amine-reactive groups. The Matrigel 284 may fill the micropores 260 which renders the vasculature channel 252 operational (i.e., the microfluidic channel is completed when micropores are closed). At step 274, the method 270 may include applying a second layer of a photo crosslinker 288 (for example, through a SVA treatment) to the vasculature microfluidic channel 252 to achieve a second surface modification (amine-reactive activation). At step 275, the method 270 may include immobilizing a positively charged and amine-rich polymer, for example, Poly-L-Lysine (PLL) 290 via covalent bonding (such as amide bond formation). At step 276, the method 270 may include promoting, by the immobilized PLL 290 the binding of ECM proteins 292 such as fibronectin via electrostatic interaction between positively charged PLL-surface and negatively charged fibronectin under physiological pH condition.

FIGS. 48B-E are exemplary images of Matrigel, fibronectin, collagen-IV and ECM-coated transendothelialization MPS model, respectively. Images of FIGS. 48B-E may include immunofluorescent staining results, confirming that Matrigel and ECMs proteins (fibronectin, collagen-IV) are immobilized at designated locations.

FIGS. 48 F-G are exemplary images of vasculature channel-micropore-interstitial space connection. FIGS. 48F-G may include vasculature channels 252, channel walls 294, micropores 260, and interstitial spaces 258. The Matrigel may be removed from the interstitial spaces 258 by pipetting. The micropores 260 may remain filled with Matrigel which allows a leakage-free ECM coating in vasculature channels 252.

Figure 63:
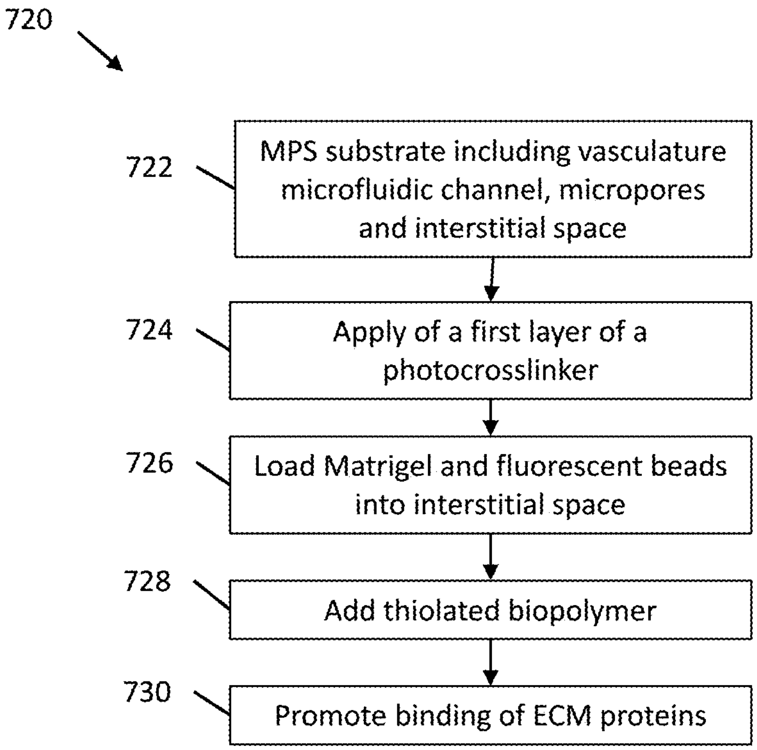
FIG. 63 is a flowchart of a construction method of an Endothelial/epithelial interfacing MPS model using thiolated polymer, according to aspects of the present embodiments.

In some embodiments, MPS construction includes an ECM coating approach using thiolated polymer. FIG. 63 is a flowchart of a construction method 720 of an Endothelial/epithelial interfacing MPS model using thiolated polymer. At step 724, the method 720 may include a MPS substrate including vasculature microfluidic channel, micropores and an interstitial space. At step 724, the method 720 may include applying a first layer of a photo crosslinker (for example, by a SVA treatment) to functionalize the surface of MPS substrate through amine-reactive chemical moieties. At step 726, the method 720 may include loading Matrigel and fluorescent beads into the interstitial space. The protein fraction of Matrigel may covalently adhere to the surface of MPS substrate which is activated by amine-reactive groups. The Matrigel may fill the micropores which renders the vasculature channel operational (i.e., the microfluidic channel is completed when micropores are closed). At step 728, the method 720 may include addition of thiolated biopolymer (for example, thiolated gelatin and/or thiolated heparin) to the vasculature channel, to achieve a second surface modification. The added thiolated biopolymer may be covalently conjugated to the substrate, resulting in a Michael-type addition between thiolated polymer and acrylate of the substrate. At step 730, the method 720 may include promoting, by surface-conjugated biopolymer the binding of ECM proteins such as fibronectin via its biophysical affinity to ECMs.

Figure 49A:
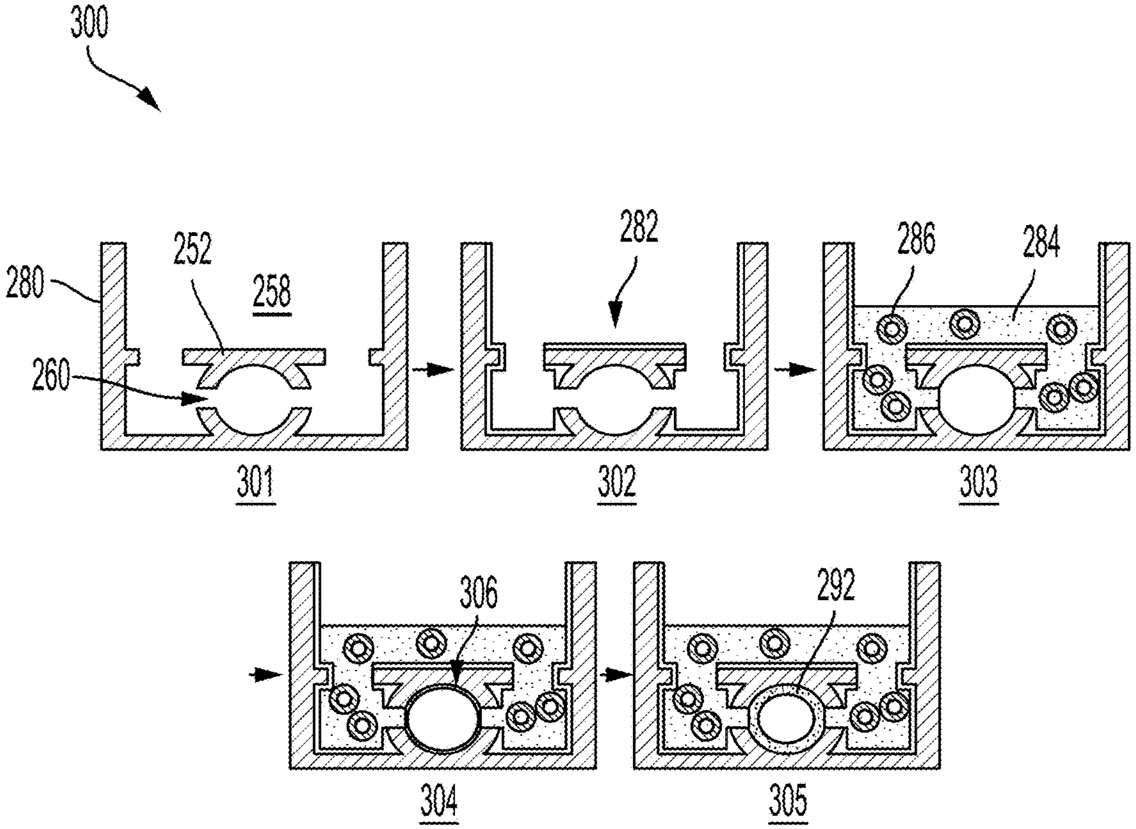
FIG. 49A is a schematic of a construction method of an Endothelial/epithelial interfacing MPS model using thiolated polymer, according to aspects of the present embodiments.
Figures 49B, 49C, 49D, 49E:
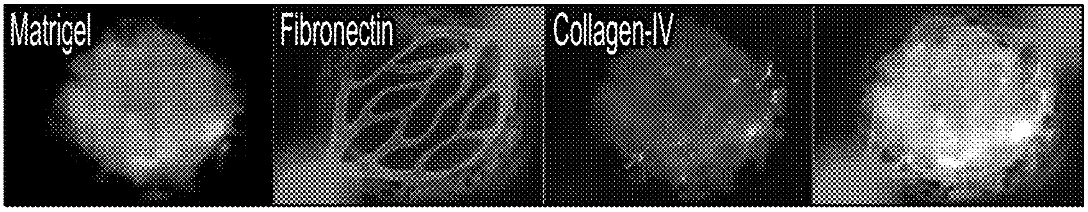
FIG. 49B is an exemplary image of Matrigel in a MPS model, according to aspects of the present embodiments.
FIG. 49C is an exemplary image of fibronectin in a MPS model, according to aspects of the present embodiments.
FIG. 49D is an exemplary image of collagen-IV in a MPS model, according to aspects of the present embodiments.
FIG. 49E is an exemplary image of an ECM-coated transendothelialization MPS model, according to aspects of the present embodiments.

FIG. 49A is a schematic of a construction method 300 of an Endothelial/epithelial interfacing MPS model using thiolated polymer. At step 301, the method 300 may include a MPS substrate 280, vasculature microfluidic channel 252, micropores 260 and an interstitial space 258. At step 302, the method 300 may include applying a first layer of a photo crosslinker 282 (for example, by a SVA treatment) to functionalize the surface of MPS substrate 280 through amine-reactive chemical moieties. At step 303, the method 300 may include loading Matrigel 284 and fluorescent beads 286 into the interstitial space 258. The protein fraction of Matrigel 284 may covalently adhere to the surface of MPS substrate 280 which is activated by amine-reactive groups. The Matrigel 284 may fill the micropores 260 which renders the vasculature channel 252 operational (i.e., the microfluidic channel is completed when micropores are closed). At step 304, the method 300 may include addition of thiolated biopolymer 306 (for example, thiolated gelatin and/or thiolated heparin) to the vasculature channel 252, to achieve a second surface modification. The added thiolated biopolymer 306 may be covalently conjugated to the substrate, resulting in a Michael-type addition between thiolated polymer and acrylate of the substrate 280. At step 305, the method 300 may include promoting, by surface-conjugated biopolymer 306 the binding of ECM proteins 292 such as fibronectin via its biophysical affinity to ECMs.

FIGS. 49B-E are exemplary images of Matrigel, fibronectin, collagen-IV and ECM-coated transendothelialization MPS model, respectively. Images of FIGS. 49B-E may include immunofluorescent staining results, confirming that Matrigel and ECMs proteins (fibronectin and collagen-IV) are immobilized at designated locations.

Various biocompatible hydrogel materials may be used to 3D print a MPS platform. In some embodiments, a hydrogel material may include PEGDA (Polyethylene Glycol Diacrylate), PEGMA (Polyethylene glycol methyl ether methacrylate), Acrylamide, Bis-acrylamide, Gelatin, Methacrylated gelatin, Thiolated gelatin, Thiolated collagen, Methacrylated collagen, Methacrylated chitosan, Thiolated chitosan, Methacrylated heparin, Thiolated Heparin, Methacrylated hyaluronic acid, Thiolated hyaluronic acid, Matrigel, Methacrylated alginate, Multi-arm PEG-Maleimide, Multi-arm PEG-Thiol, Multi-arm PEG-DBCO, Multi-arm PEG-N3, and Multi-arm PEG-Biotin with streptavidin.

Several 3D printing methods may be utilized to generate interconnected vasculature channel and interstitial space including widely distributed micropores. In some embodiments, 3D printing may include photopolymerization method based on Digital Light Processing (DLP) approach using basal material PEGDA, photoinitiator (e.g., Irgacure 2959 and Lithium phenyl-2,4,6-trimethylbenzoylphosphinate; LAP), and photoabsorber (e.g., tartrazine). In some embodiments, 3D printing may include Stereolithography (SLA)-based bioprinting, Extrusion bioprinting or Ink-jet bioprinting and both one photon and two photon DLP.

In some embodiments, a MPS substrate may include an acrylate-rich hydrogel, for example, a PEGDA-based acylate-rich hydrogel. In some embodiments, a bioconjugation approach to immobilize ECM proteins and/or gel-embedded tissues for a PEGDA-based acylate-rich hydrogel may include a combination of photo crosslinking and amine-targeting using Acrylate-PEG-NHS (SVA). In the presence of a photoinitiator, acrylate group of SVA may covalently adhere to a free acrylate group of a MPS substrate via photo crosslinking. Successively, NHS group which is a chemical moiety that interacts with primary amine group of a protein via amide bond formation, may be functionalized on a surface of MPS. Afterwards, ECM proteins and/or ECM-based hydrogel may be applied, and consequently immobilized on the surface of MPS. In some embodiments, photo crosslinking reagent may include Sulfo-SANPAH, Sulfo-NHS-Diazirine, and NHS-Diazirine.

In some embodiments, a MPS substrate may include a non-acrylate hydrogel. In some embodiments, a non-acrylate hydrogel may contain primary amine groups, for example, a gelatin-based gel, a collagen-based gel, and a chitosan-based gel. In some embodiments, a homo-bifunctional amine-reactive crosslinker may be used for a hydrogel that contains primary amine groups. Homo-bifunctional amine-reactive crosslinkers contain two amine-reactive moieties including n-hydroxysuccinimidyl ester (NHS) and N-hydroxysulfosuccinimidyl ester (Sulfo-NHS), and an aldehyde group, enabling covalently crosslinking of amine-rich surface of MPS and ECM proteins via forming an amide bond (amine and NHS/Sulfo-NHS) or an imine bond (amine and aldehyde). Examples of homo-bifunctional amine-reactive crosslinkers include bis(sulfosuccinimidyl)suberate (BS3), disuccinimidyl suberate (DSS), dithiobis(succinimidyl propionate) (DSP), 3,3'-dithiobis(sulfosuccinimidyl propionate) (DTSSP) and Glutaraldehyde. In some embodiments, a non-acrylate hydrogel may contain thiol groups. In some embodiments, a hetero-bifunctional maleimide reactive and amine-reactive crosslinker may be used for a hydrogel that contains thiol groups. Maleimide reactive groups may be conjugated to thiol groups on a surface of MPS and amine-reactive groups may interact with primary amine groups in ECM proteins. Examples of a hetero-bifunctional maleimide reactive and amine-reactive cross-linker may include Succinimidyl-4-(N-maleimidomethyl) cyclohexane-1-carboxylate (SMCC), Sulfosuccinimidyl-4-(N-maleimidomethyl)cyclohexane-1-carboxylate (Sulfo-SMCC), N-γ-maleimidobutyryl-oxysuccinimide ester (GMBS), and N-γ-maleimidobutyryl-oxysulfosuccinimide ester (Sulfo-GMBS).

Interstitial Infill and Interstitial Space

The present disclosure teaches that, in some embodiments, an ecosystem that produces a platform for creating physical, synthetic models of an organ, a tissue, and/or a cell, via bioprinting of a scaffold comprises a bioprinted entity, vasculature, an interstitial infill, and/or an interstitial space.

Those skilled in the art, reading the present disclosure, will appreciate that, in some embodiments, the interstitial space may be a void wherein a cell in a fluid(s) and/or a polymer (e.g., a hydrogel) are seeded to create a tissue. In some such embodiments, the cell in a fluid(s) may be an endothelial cell optionally coupled to live tissues and/or a cell other than an endothelial cell.

In some embodiments, the interstitial infill may be a polymer anchor and/or structure (e.g., a hydrogel) that enables creation of a two-dimensional or three-dimensional tissue through stimulation of cell association. In some such embodiments, the cell in a fluid(s) may be an endothelial cell optionally coupled to live tissues and/or a cell other than an endothelial cell.

In some embodiments, the interstitial infill comprises an interstitial pattern that approximates the geometries of the cell and/or tissue(s) native format. In some embodiments, the interstitial pattern is selected from a fibrous and/or a spherical pattern.

In some embodiments, the interstitial pattern is a fibrous pattern. In some embodiments, the fibrous pattern may be modified according to different parameters (e.g., density, thickness, orientation).

The present disclosure teaches, that at least in some embodiments, the interstitial space is perfused with a coating moiety through a chamber. In some such embodiments, the coating moiety is a cell and/or plurality of cells, which may be the same or different. In further embodiments, the cell is an endothelial cell and a cell other than an endothelial cell. In some embodiments, the cell is an endothelial cell. In some embodiments, the cell is other than an endothelial cell.

In some embodiments, the interstitial pattern is a spherical pattern, which may comprise pores and/or windows. In some embodiments, the spherical pattern may be modified according to different parameters (e.g., size, wall thickness, number of microspheres).

Cartridge

Figure 41A:
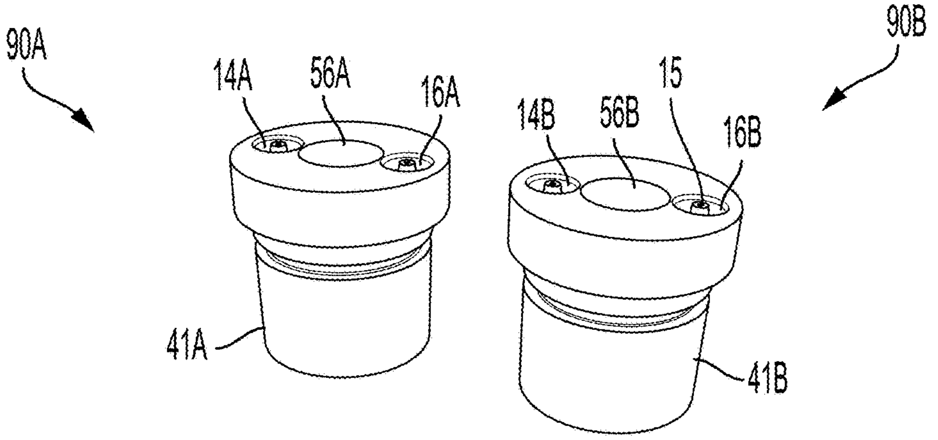
FIG. 41A illustrates examples of cartridges, according to aspects of the present embodiments.
Figure 41B:
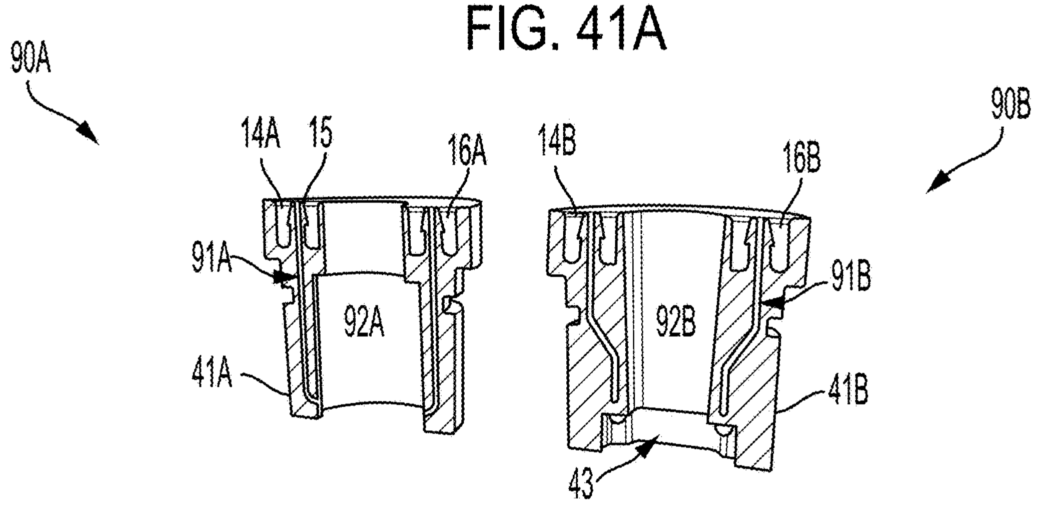
FIG. 41B illustrates exemplary cross sections of cartridges, according to aspects of the present embodiments.
Figure 41C:
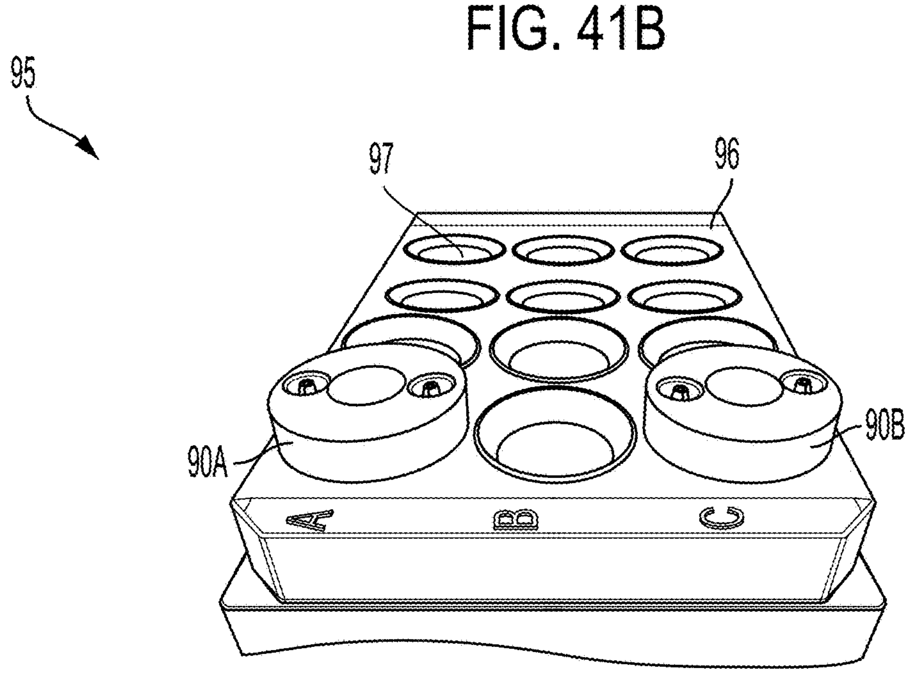
FIG. 41C illustrates an assembly for modeling organ-on-a-chip, according to aspects of the present embodiments.

In some embodiments, an assembly for modeling organ-on-a-chip may include a cartridge that enables high throughput along with imaging capabilities. A cartridge may include a 3D printed part (resin) that houses a scaffold and creates the microfluidic interface between the scaffold and a pump. Such cartridge may be used to model organ-on-a-chip using well plates, and handled by currently available robot systems. FIG. 41A illustrates examples of cartridges 90A and 90B, according to aspects of the present embodiments. Cartridge 90A may include a reservoir 41A, an inlet 14A, an outlet 16A, and an access port 56A. Cartridge 90B may include a reservoir 41B, an inlet 14B, an outlet 16B, and an access port 56B. The inlets 14A, 14B and the outlets 16A, 16B may each include a hosebarb 15 which connects to a flexible hose and/or tube. FIG. 41B illustrates exemplary cross sections of cartridges 90A and 90B, also shown in FIG. 41A. Cartridge 90A may include well 92A, and internal channels 91A fluidly connecting inlet 14A and outlet 16A to the well 92A. Cartridge 90B may include well 92B, chip slot 43, and internal channels 91B fluidly connecting inlet 14B and outlet 16B to the chip slot 43. FIG. 41C illustrates an assembly 95 for modeling organ-on-a-chip, according to aspects of the present embodiments. The platform 95 may include a well plate 96 and cartridges 90A and 90B positioned within wells 97 of the well plate 96.

Figure 64:
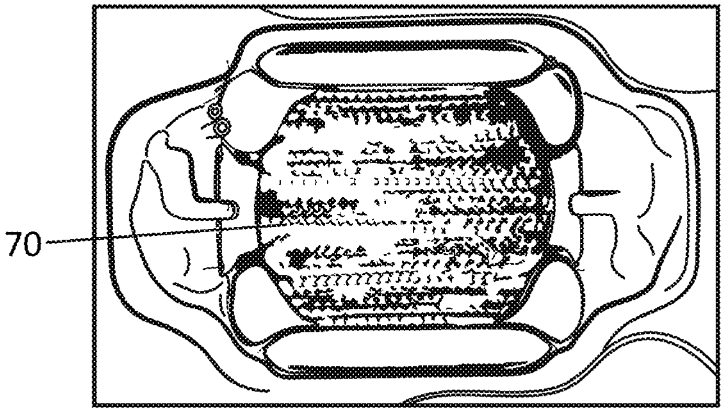
FIG. 64 shows an example of a scaffold used in a cartridge, according to aspects of the present embodiments.

FIG. 64 shows an example of a scaffold 70 used in cartridge 90B, according to aspects of the present embodiments.

Figure 65:
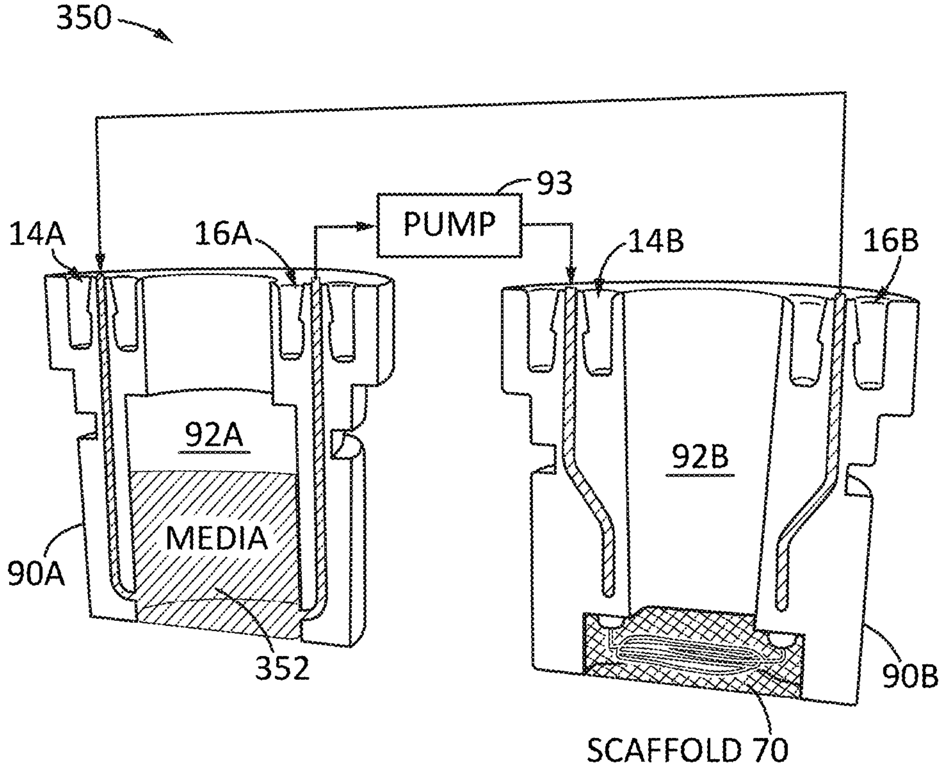
FIG. 65 illustrates an example of a setup to fluidly couple two cartridges, according to aspects of the present embodiments.
Figure 66:
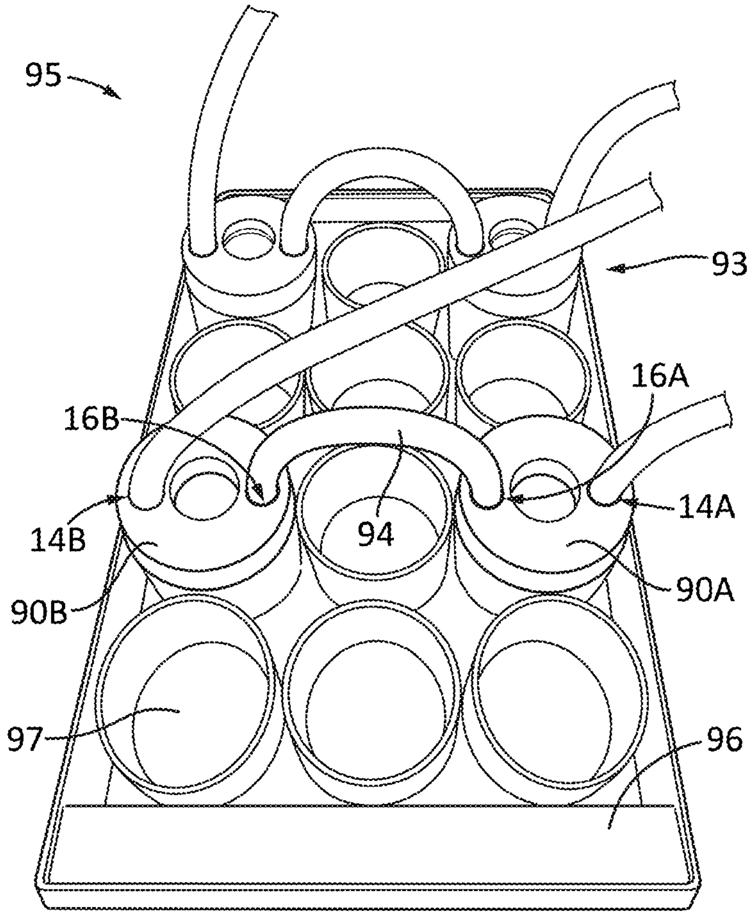
FIG. 66 illustrates an assembly for modeling organ-on-a-chip, according to aspects of the present embodiments.

FIG. 65 illustrates an example of a setup 350 to fluidly couple cartridge 90A and cartridge 90B, according to aspects of the present embodiments. The output 16B of cartridge 90B may be fluidly connected to the input 14A of the cartridge 90A by a tube, while the output 16A of cartridge 90A may be fluidly connected to the input 14B of the cartridge 90B by a pump 93. The well 92 may be used to store media 352 for perfusion of a scaffold 70 while the cartridges 90A, 90B are seated within wells of a well plate. FIG. 66 illustrates an assembly 95 for modeling organ-on-a-chip, according to aspects of the present embodiments. The assembly 95 may include a well plate 96 and cartridges 90A and 90B positioned within wells 97 of the well plate 96. The output 16B of cartridge 90B may be fluidly connected to the input 14A of the cartridge 90A by a tube 94, while the output 16A of cartridge 90A may be fluidly connected to the input 14A of the cartridge 90A through a pump 93.

Figure 42A:
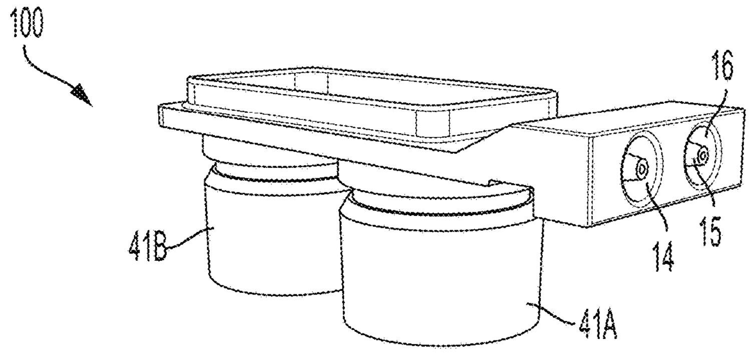
FIG. 42A illustrates an example of a cartridge, according to aspects of the present embodiments.
Figure 42D:
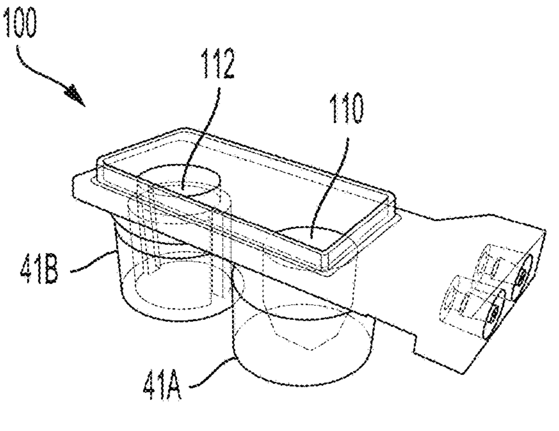
FIG. 42D illustrates an exemplary view of a cartridge including wells within reservoirs, according to aspects of the present embodiments.

In some embodiments, a single cartridge may include two reservoirs to house and interface the microfluidic flow to one or two scaffolds, depending on the configuration. Multiple of such cartridges can be assembled in a well plate, ensuring the scaffolds and tubing are equidistant/symmetrically distributed, which is highly desirable in a high-throughput system given the complexity and number of tubes. FIG. 42A illustrates an example of cartridge 100, according to aspects of the present embodiments. Cartridge 100 may include reservoirs 41A, 41B, an inlet 14, and an outlet 16. Each inlet 14 and outlet 16 may include a hosebarb 15 which connects to a flexible hose and/or tube. FIG. 42D illustrates an exemplary view of cartridge 100 including wells 110 and 112 within reservoirs 41A and 41B, respectively. The well 110 may include a volume of 2358.16 $mm^3$ and a surface area of 7.21 $cm^2$. The well 112 may include a volume of 4965.6 $mm^3$ and a surface area of 13.48 $cm^2$.

Figure 42C:
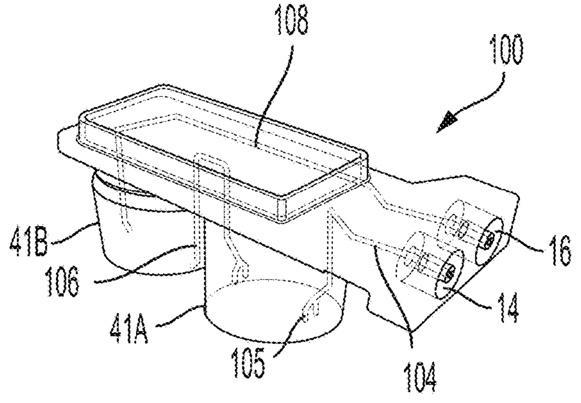
FIG. 42C illustrates an exemplary view of a cartridge including internal channels, according to aspects of the present embodiments.

FIG. 42C illustrates an exemplary view of cartridge 100 including internal channels 104, 106 and 108. The internal channel 104 may fluidly connect the inlet 14 to reservoir 41A, the internal channel 106 may fluidly connect reservoir 41A to reservoir 41B, and the internal channel 108 may fluidly connect reservoir 41B to the outlet 16 The internal channel 104 may include a volume of 19.94 $mm^3$ and a surface area of 1.05 $cm^2$. The internal channel 106 may include a volume of 23.41 $mm^3$ and a surface area of 1.22 $cm^2$. The internal channel 108 may include a volume of 45.39 $mm^3$ and a surface area of 2.34 $cm^2$. Each of the internal channels 104 and 106 may split into two sub-channels 105 inside reservoir 41A, forming a bifurcation (e.g., fork shape). As a result, the microfluidic interface between the cartridge 100 and a scaffold is established through four sub-channels 105. Each sub-channel 105 may be connected to a separate fluidic channel, allowing for individual control. In some embodiments, the division of internal channels 104,106 into four sub-channels 105 may enable the use of scaffolds with high vasculature density. This is achieved by partitioning the flow at the cartridge level, prior to interfacing with the scaffold, rather than within the scaffold itself. In such cases, creating flow bifurcation within the scaffold may not be optimal due to limited bulk gel volume. In some embodiments, the division of internal channels 104,106 into four sub-channels 105 may be used in scaffolds that are perfused with two different types of media. In some embodiments, the division of internal channels 104,106 into four sub-channels 105 may be used to collect by-products of cell function, such as bile. Since the reservoir 41B may be used to store media, the internal channels 106, 108 may not split as they act solely as media inlet or outlet.

Figure 67A:
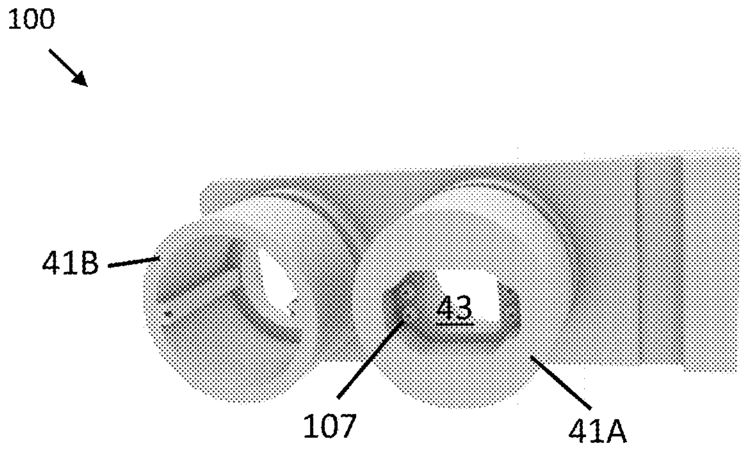
FIG. 67A illustrates an example of a cartridge, according to aspects of the present embodiments.
Figure 67B:
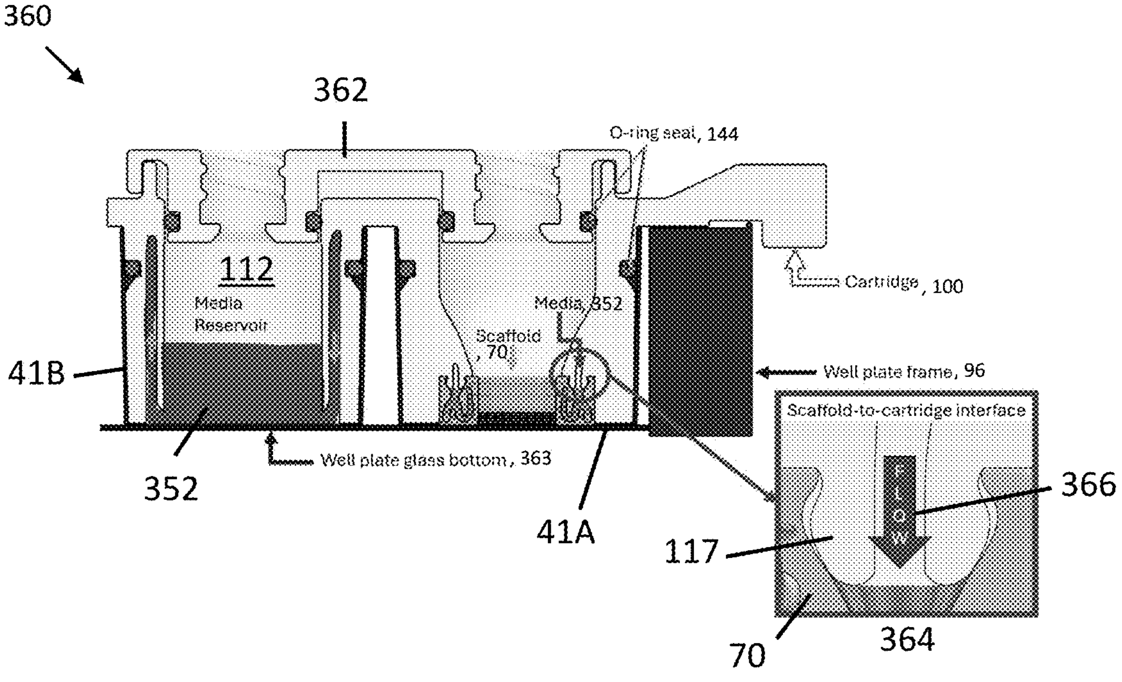
FIG. 67B illustrates an example of a setup to fluidly couple reservoirs of a cartridge, according to aspects of the present embodiments.

FIG. 67A illustrates an example of cartridge 100, according to aspects of the present embodiments. Cartridge 100 may include reservoirs 41A and 41B. The reservoir 41A may include a chip slot 43, and four hosebarbs 107. FIG. 67B illustrates an example of a setup 360 to fluidly couple reservoirs 41A and 41B of a cartridge 100, according to aspects of the present embodiments. A scaffold 70 may be inserted into the bottom of reservoir 41A, and subsequently cartridge 100 is placed into two wells of a well plate 96. The glass bottom 363 of the well plate 96 compresses the scaffold 70 against the chip slot 40, ensuring a microfluidic seal at the scaffold-to-cartridge interface. A set of O-rings 144 creates a seal between the cartridge 100 and the well plate 96, preventing contaminants from entering and securing the cartridge 100 in place. A sealed lid 362 with O-rings 144 and air filters is used to seal the cartridge 100, preventing the ingress of contaminants while allowing gas exchange. The well 112 of reservoir 41B may be used to store media 352 for perfusion of a scaffold 70 within the reservoir 41A. Closeup 364 shows the interface between the scaffold 70 and the hosebarb 117, and the direction of flow 366 of media 352 from the cartridge 100 into the scaffold 70.

Figure 68A:
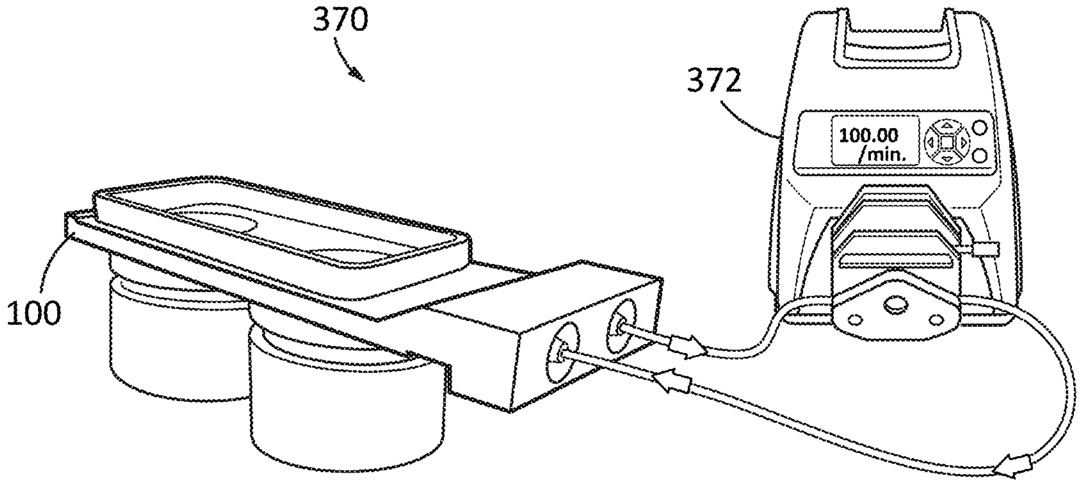
FIG. 68A illustrates an example of a setup for a recirculatory flow through a cartridge, according to aspects of the present embodiments.
Figure 68B:
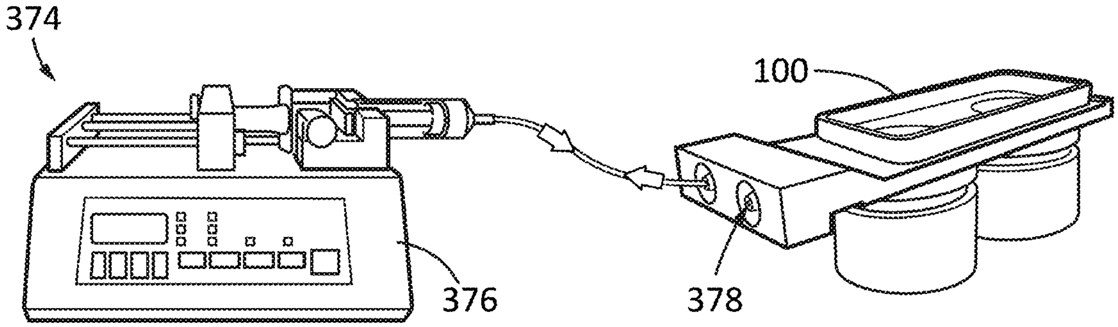
FIG. 68B illustrates an example of a setup for a bidirectional flow through a cartridge, according to aspects of the present embodiments.

FIG. 68A illustrates an example of a setup 370 for a recirculatory flow through a cartridge 100, according to aspects of the present embodiments. The setup 370 may include a cartridge 100 and a peristaltic pump 372. FIG. 68B illustrates an example of a setup 374 for a bi-directional flow through a cartridge 100, according to aspects of the present embodiments. The setup 374 may include the cartridge 100 with a capped outlet 378 and a syringe pump 376.

Figure 42B:
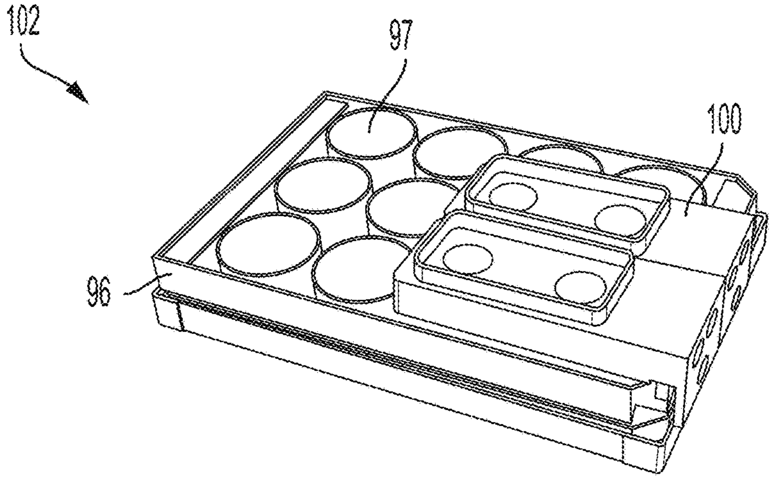
FIG. 42B illustrates an assembly for modeling organ-on-a-chip, according to aspects of the present embodiments.
Figure 69:
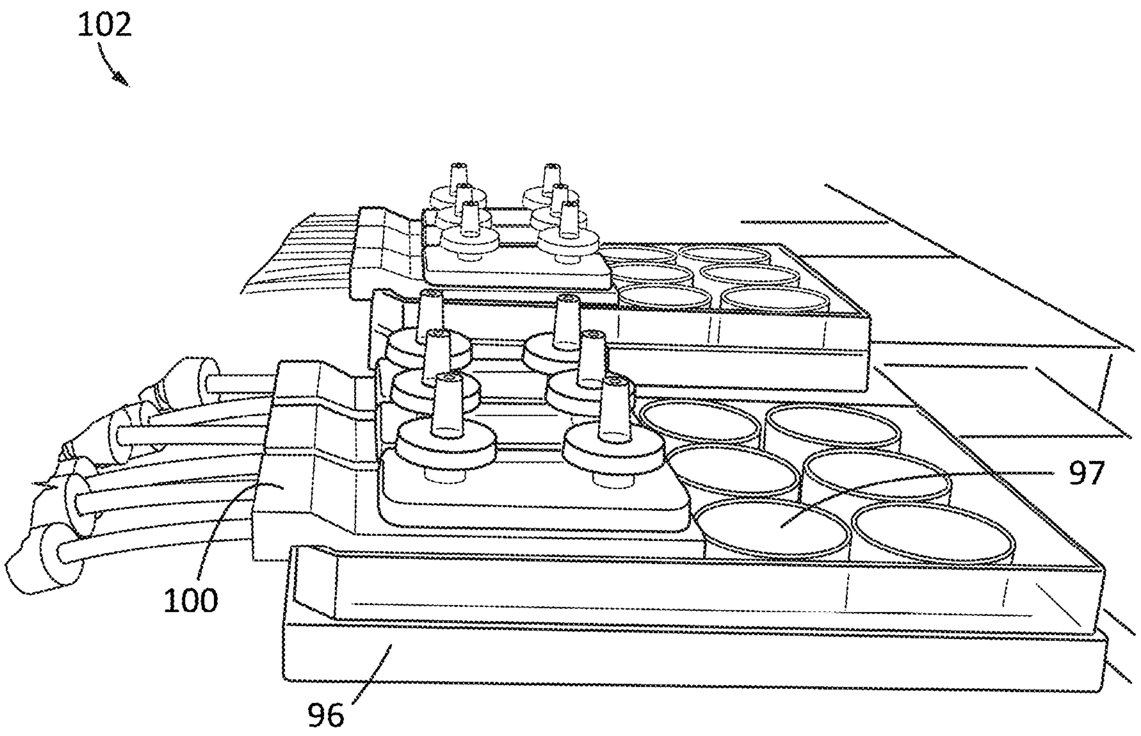
FIG. 69 illustrates an assembly for modeling organ-on-a-chip, according to aspects of the present embodiments.

FIG. 42B illustrates an assembly 102 for modeling organ-on-a-chip, according to aspects of the present embodiments. The assembly 102 may include a well plate 96 and a cartridge 100 positioned within wells 97 of the well plate 96. FIG. 69 illustrates an assembly 102 for modeling organ-on-a-chip, according to aspects of the present embodiments. The assembly 102 may include a well plate 96 and a plurality of cartridges 100 positioned within wells 97 of the well plate 96.

Figure 42E:
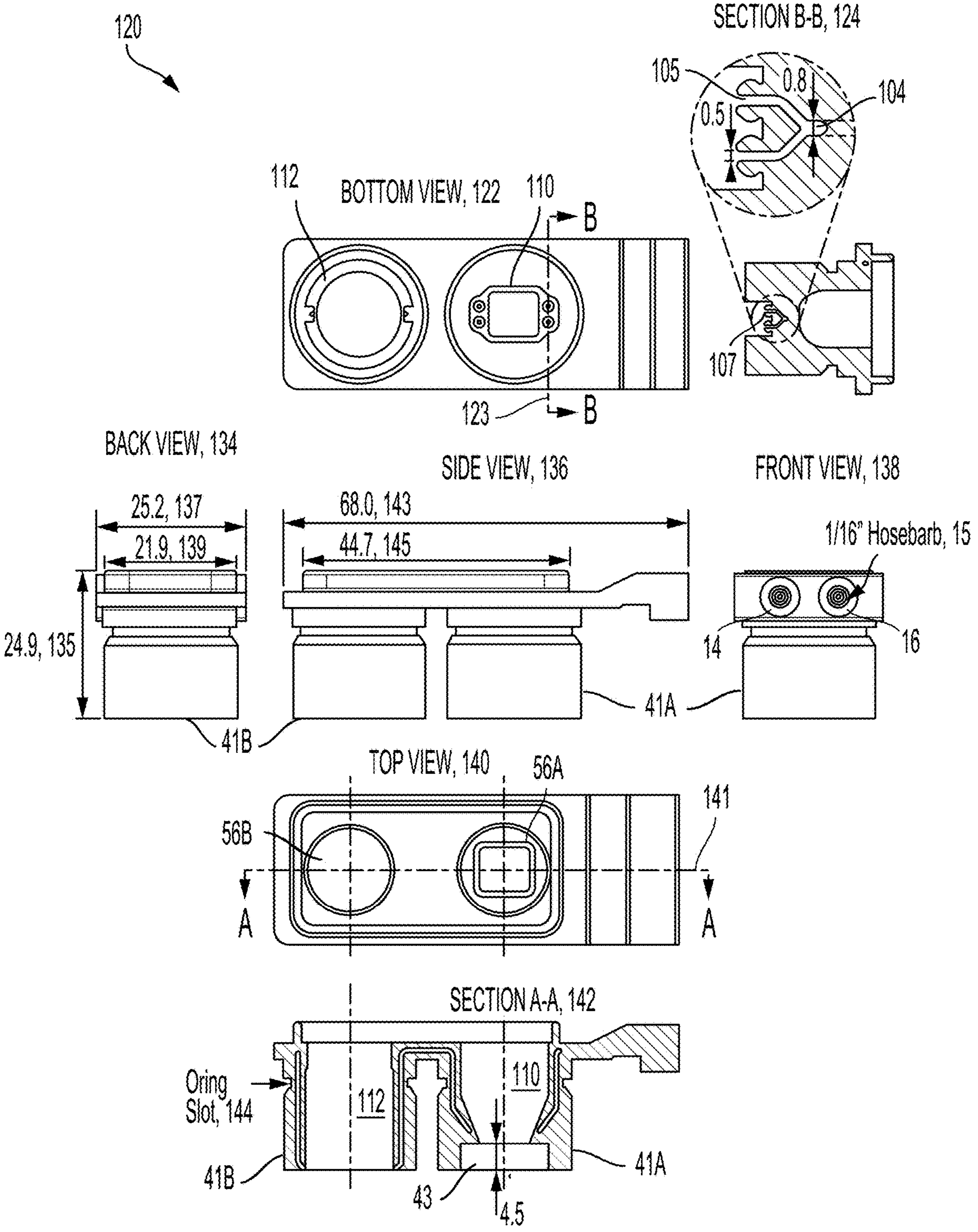
FIG. 42E illustrates exemplary diagram of a cartridge, according to aspects of the present embodiments.

FIG. 42E illustrates exemplary diagram 120 of cartridge 100, according to aspects of the present embodiments. The diagram 120 may include a top view 140, a bottom view 122, a back view 134, a side view 136, and a front view 138. The top view 140 may include access ports 56A, 56B. Section A-A 142 corresponds to a cross section at line A-A 141 of the top view 140. The Section A-A 142 may include reservoirs 41A, 41B, the wells 110 and 112, the internal channels 104, 106 and 108, and O-ring slots 144. The chip slot 43 may include a thickness of 4.5 mm. The bottom view 122 may include well 110 and chip slot 43. Section B-B 124 corresponds to a cross section at line B-B 123 of the bottom view 122. The Section B-B 124 may include two hosebarbs 107. A close-up of Section B-B may include channel 104 which splits into two channels 105. The channel 104 may include a diameter of 0.8 mm and the channels 105 may include a diameter of 0.5 mm. The back view 134 may include reservoir 41B. The reservoir 41B may include a height 135 of 24.6 mm and a diameter 137 of 25.2 mm. The access port 56B of reservoir 41B may include a diameter 139 of 21.9 mm. The side view 136 may include a total cartridge length 143 of 68.0 mm and a cover length 145 of 44.7 mm. The front view 138 may include reservoir 41A, inlet 14, outlet 16 and hosebarbs 15. The hosebarb 15 may include a diameter of 1/16 inches.

Figure 43:
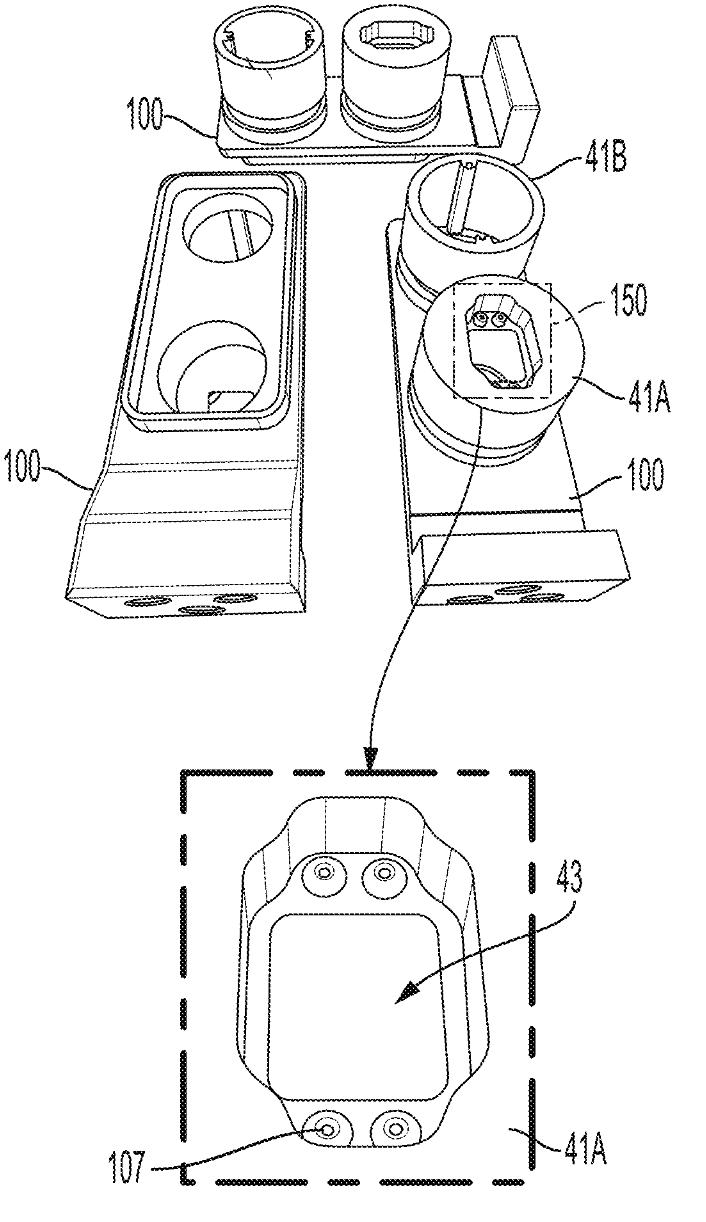
FIG. 43 shows printed examples of a cartridge, according to aspects of the present embodiments.

FIG. 43 shows printed examples of cartridge 100, according to aspects of the present embodiments. The cartridge 100 may be 3D printed using a metal. A metallic cartridge 100 may exhibit durability, heat resistance, low drug sorption and reusability. For example, a metallic cartridge 100 may be autoclaved for maintaining cleanliness and/or sterility. in some embodiments, the cartridge 100 may be 3D printed using Stainless Steel 316L. Stainless Steel 316L may provide biocompatibility, corrosion resistance, and mechanical properties which enable the use of cartridge 100 in Cytotoxicity and absorption studies. A close-up of a selected area 150 of the reservoir 41A may include chip slot 43 and hosebarbs 107. In some embodiments, the cartridge may also and/or instead be coated with "paralyene" to enable low absorption.

Figure 44A:
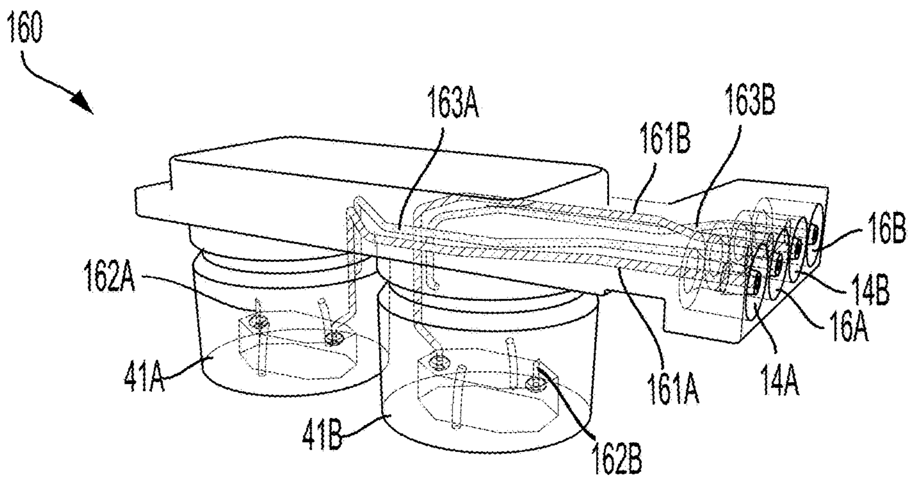
FIG. 44A illustrates an example of a cartridge, according to aspects of the present embodiments.
Figure 70:
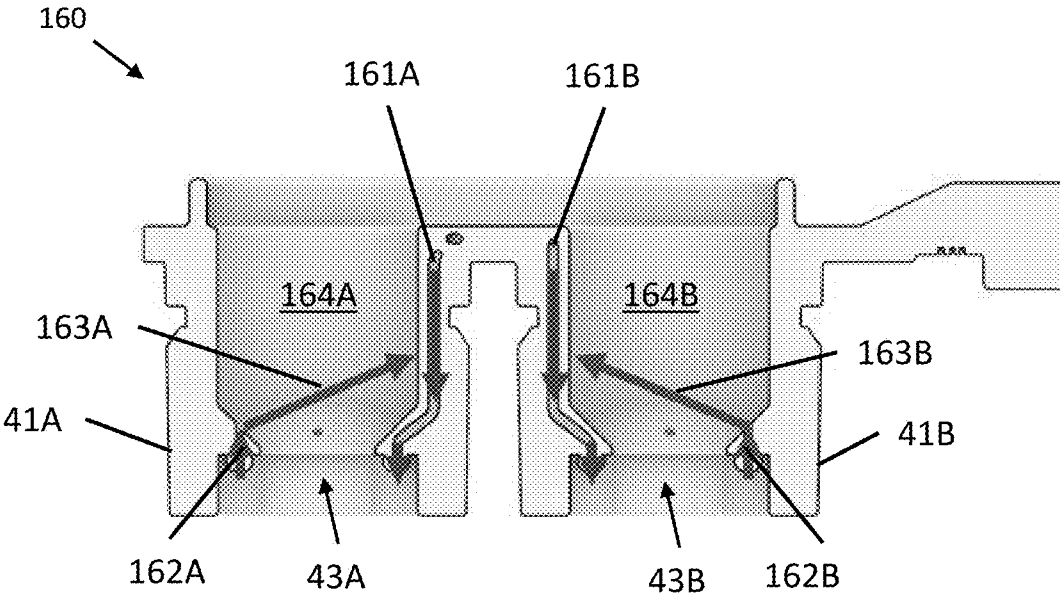
FIG. 70 illustrates an exemplary cross section of a cartridge, according to aspects of the present embodiments.

FIG. 44A illustrates an example of a cartridge 160, according to aspects of the present embodiments. The cartridge 160 may include two reservoirs 41A, 41B, two inlets 14A,14B, and two outlets 16A, 16B. The internal channel 161A may fluidly connect the inlet 14A to the reservoir 41A, and the internal channel 163A may fluidly connect reservoir 41A to the outlet 16A. The internal channel 161B may fluidly connect the inlet 14B to the reservoir 41B, and the internal channel 163B may fluidly connect reservoir 41B to the outlet 16B. The internal channels 162A and 162B provide internal interfaces inside reservoirs 41A and 41B, respectively. FIG. 70 illustrates an exemplary cross section of a cartridges 160, according to aspects of the present embodiments. The cartridge 160 may include two reservoirs 41A, 41B, two chip slots 43A, 43B, and two wells 164A, 164B. The wells 164A, 164B, located above the chip slots 43A, 43B, may be used to store media. The internal channel 161A may receive the media from a pump outlet and direct it to the chip slots 43A where a scaffold can be inserted. The media may travel through the scaffold's vasculature and subsequently directed the well 164A by the internal channel 162A. The internal channel 163A may direct the media from well 164A to the pump inlet which feeds it back into internal channel 161A, thereby completing a perfusion cycle. The internal channel 161B may receive the media from a pump outlet and direct it to the chip slots 43B where a scaffold can be inserted. The media may travel through the scaffold's vasculature and subsequently directed the well 164B by the internal channel 162B. The internal channel 163B may direct the media from well 164B to the pump inlet which feeds it back into internal channel 161B, thereby completing a perfusion cycle.

Figure 44B:
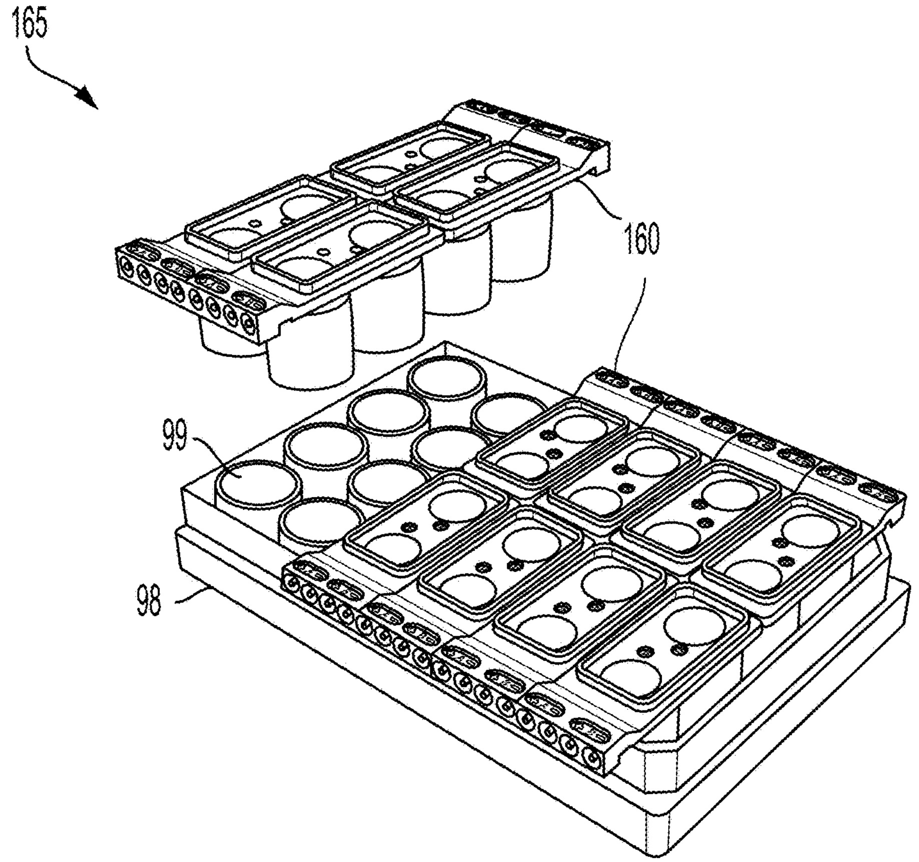
FIG. 44B illustrates an assembly for modeling organ-on-a-chip, according to aspects of the present embodiments.

FIG. 44B illustrates an assembly 165 for modeling organ-on-a-chip, according to aspects of the present embodiments.

The platform 165 may include a well plate 98 and one or more cartridges 160 positioned within wells 99 of the well plate 98.

Figure 45:
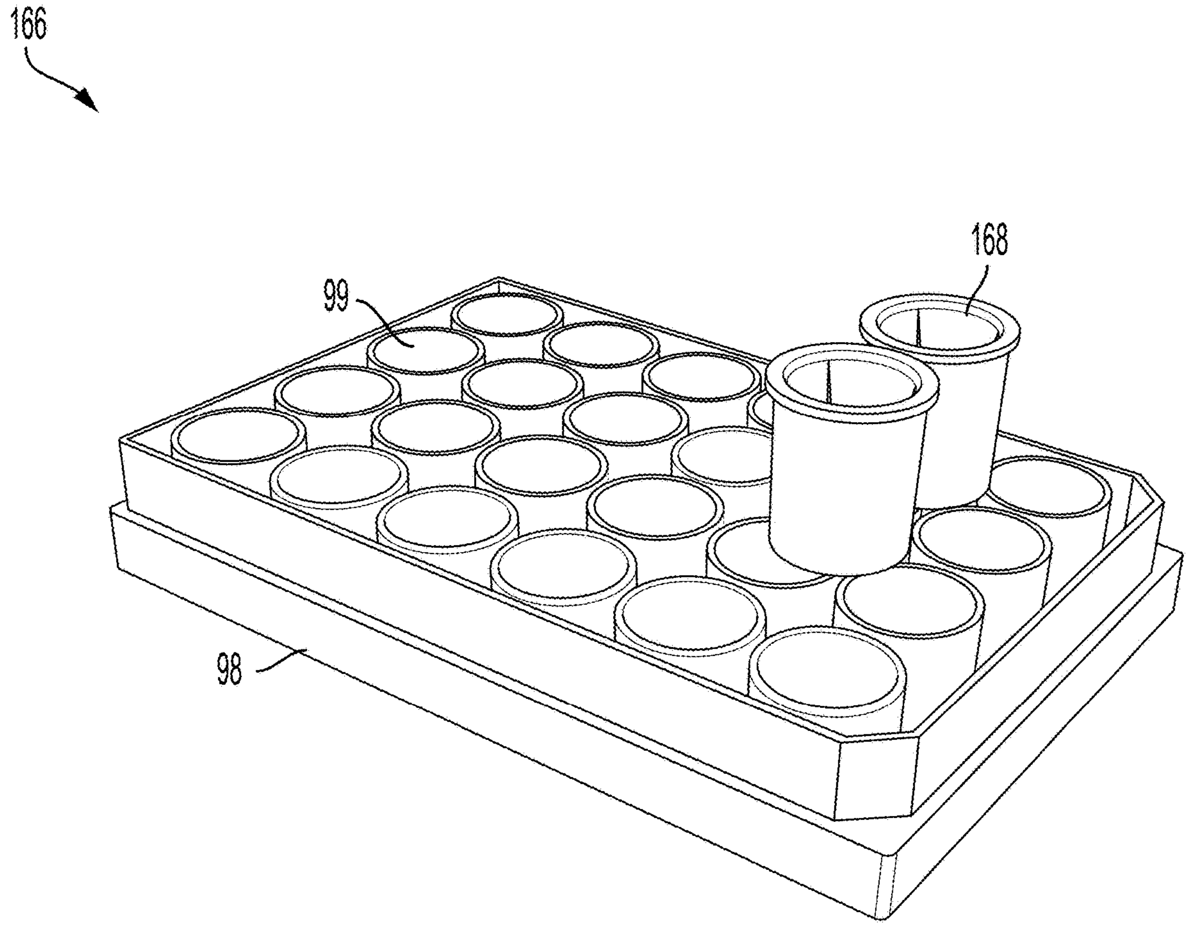
FIG. 45 illustrates an imaging setup for modeling organ-on-a-chip, according to aspects of the present embodiments.

FIG. 45 illustrates an imaging setup 166 for modeling organ-on-a-chip, according to aspects of the present embodiments. The imaging setup 166 may include one or more imaging inserts 168, and a well plate 98. The imaging inserts 198 may secure and/or set the orientation of the scaffolds. The imaging setup 166 setup may enhance the efficiency of imaging process, allowing for a higher throughput. According to aspects of the present embodiments, imaging setup 166 may also be used to extract samples (i.e., from the reservoir and/or interstitial space) to enable downstream testing.

Figure 71A:
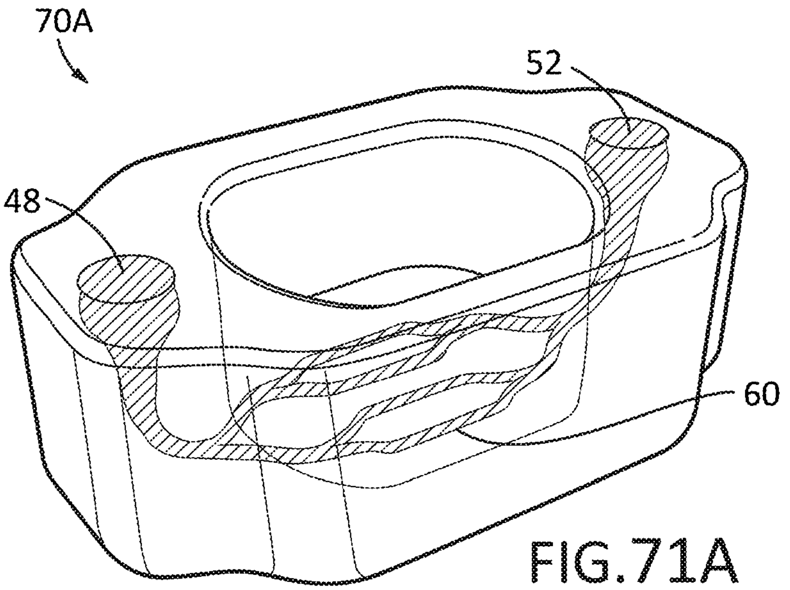
FIGS. 71A and 71B illustrate exemplary scaffolds to be used in a cartridge, according to aspects of the present embodiments.
Figure 71B:
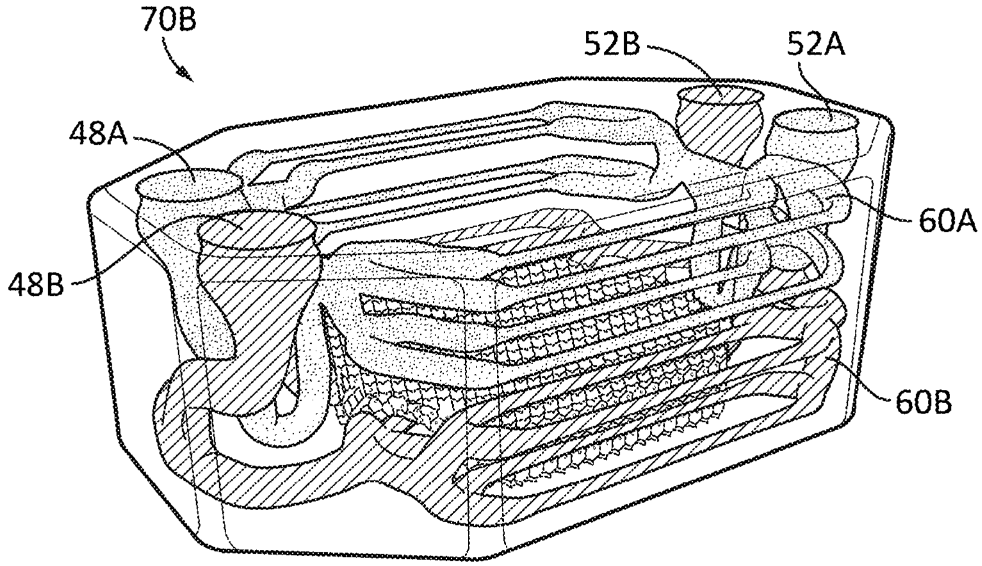

FIGS. 71A and 71B illustrate exemplary scaffolds 70A, 70B to be used in a cartridge, according to aspects of the present embodiments. The scaffold 70A may include a vasculature 60, a vasculature inlet 48 and a vasculature outlet 52. The scaffold 70A, for example, in a simpler design where one inlet and one outlet is sufficient. The scaffold 70A may be used inside a cartridge 90B. The scaffold 70B may include two vasculatures 60A, 60B, two vasculature inlets 48A, 48B and two vasculature outlets 52A, 52B. The scaffold 70B, for example, may be used in complex designs, i.e., high vasculature density, where two inlets and two outlets are desirable. Additionally, the scaffold 70B may be perfused with two different types of media or used to collect by-products of cell function, such as bile. The scaffold 70B may be used inside a cartridge 100 or a cartridge 160.

Figure 46A:
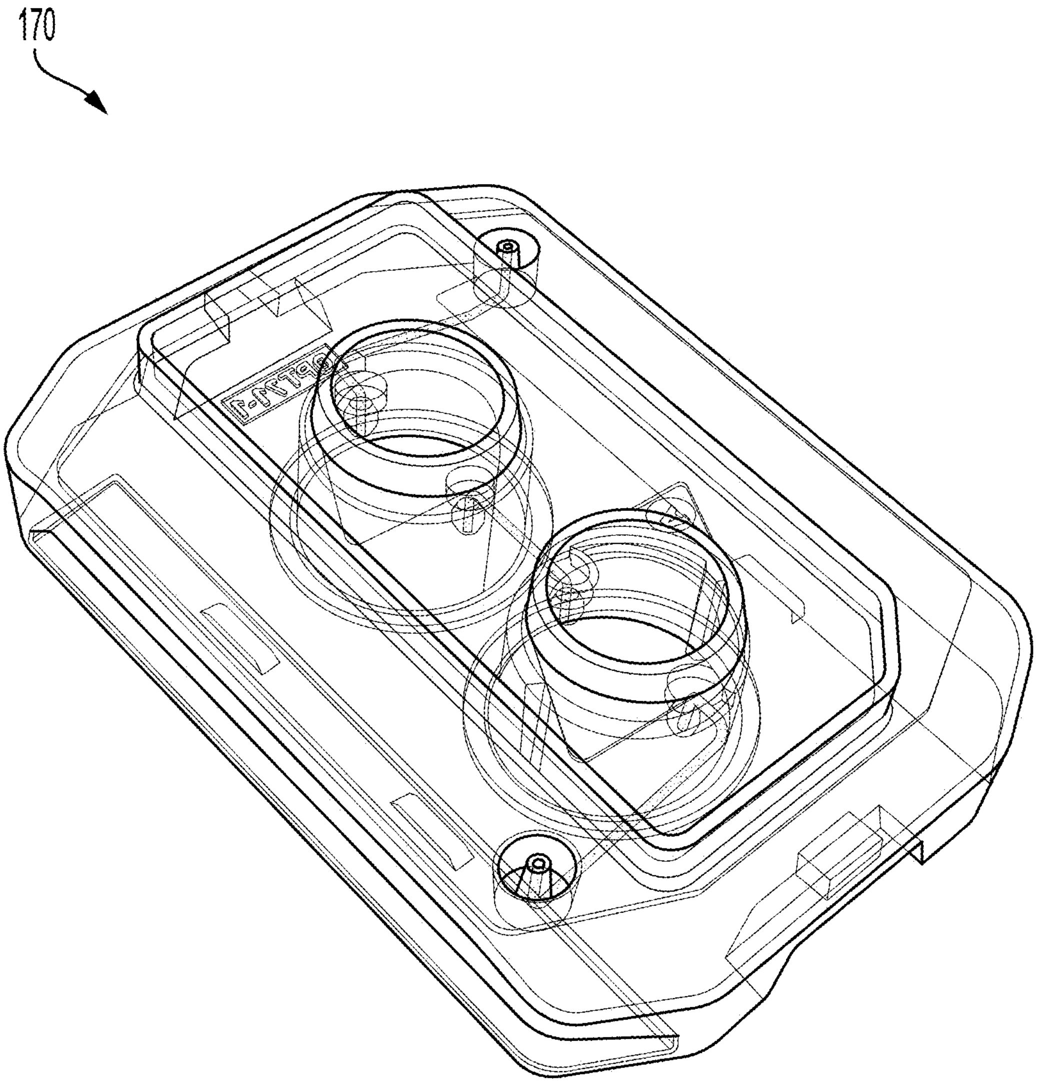
FIG. 46A illustrates an example of a cartridge, according to aspects of the present embodiments.
Figure 46B:
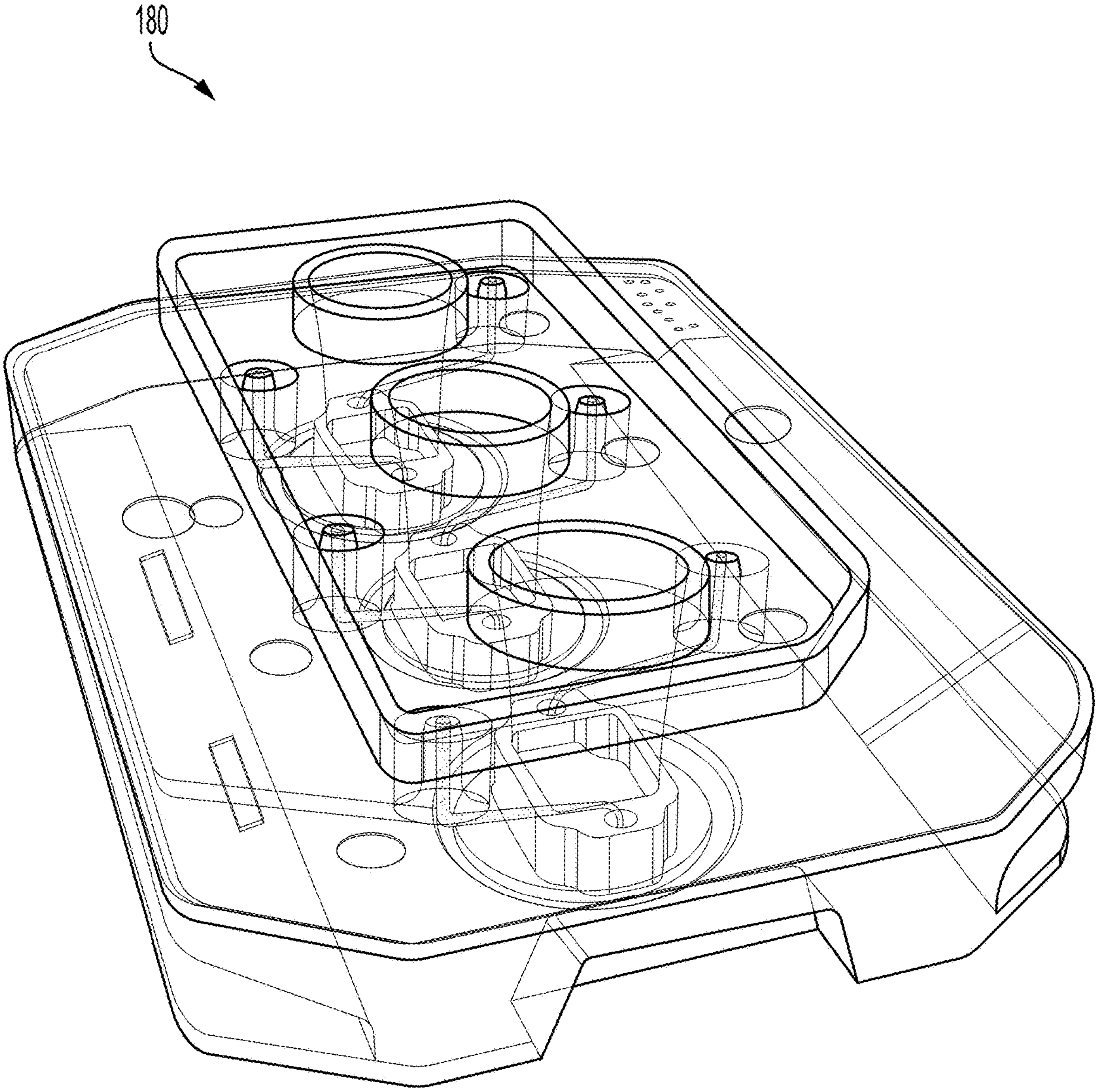
FIG. 46B illustrates an example of a cartridge, according to aspects of the present embodiments.
Figure 46C:
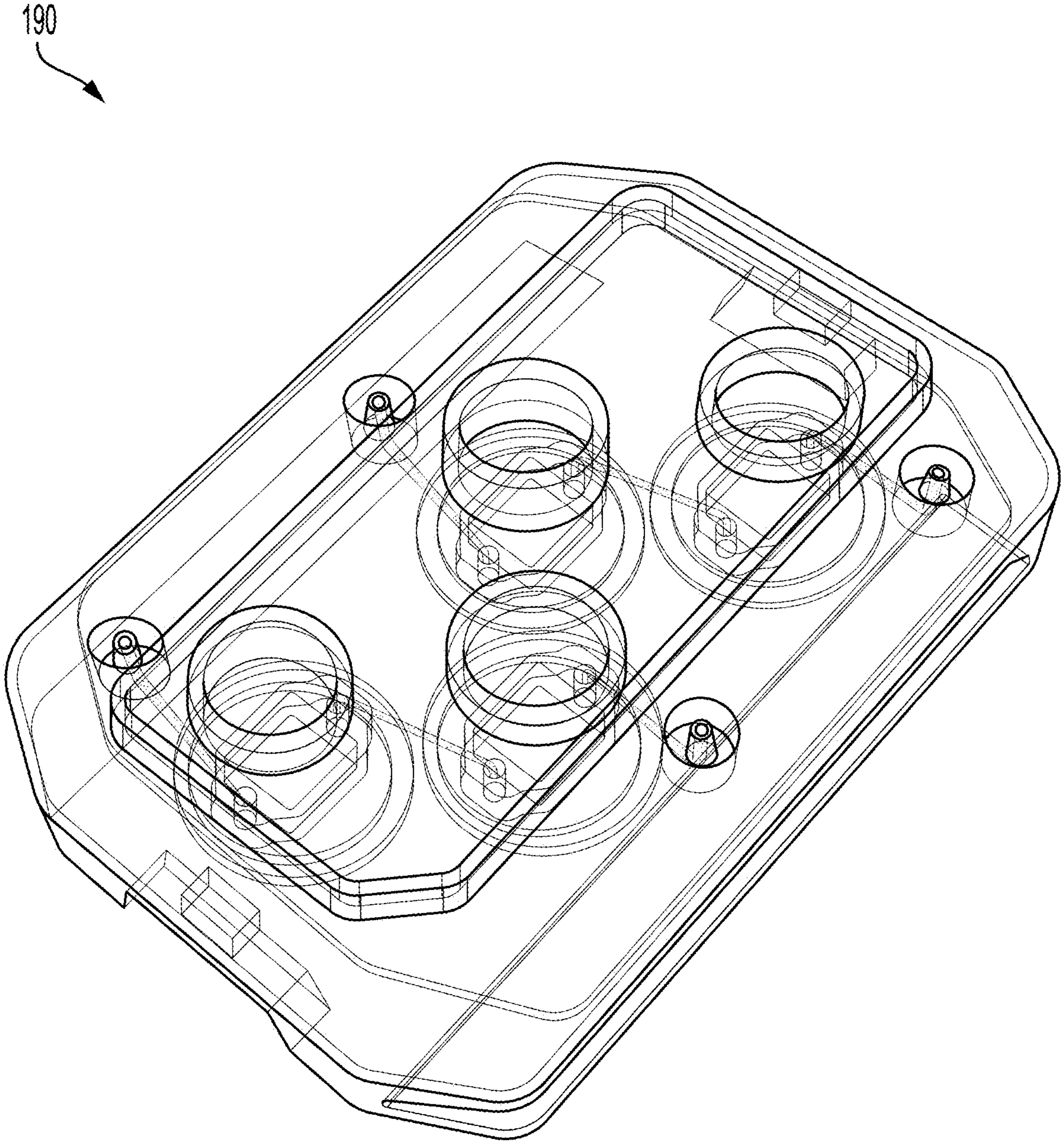
FIG. 46C illustrates an example of a cartridge, according to aspects of the present embodiments.
Figure 46D:
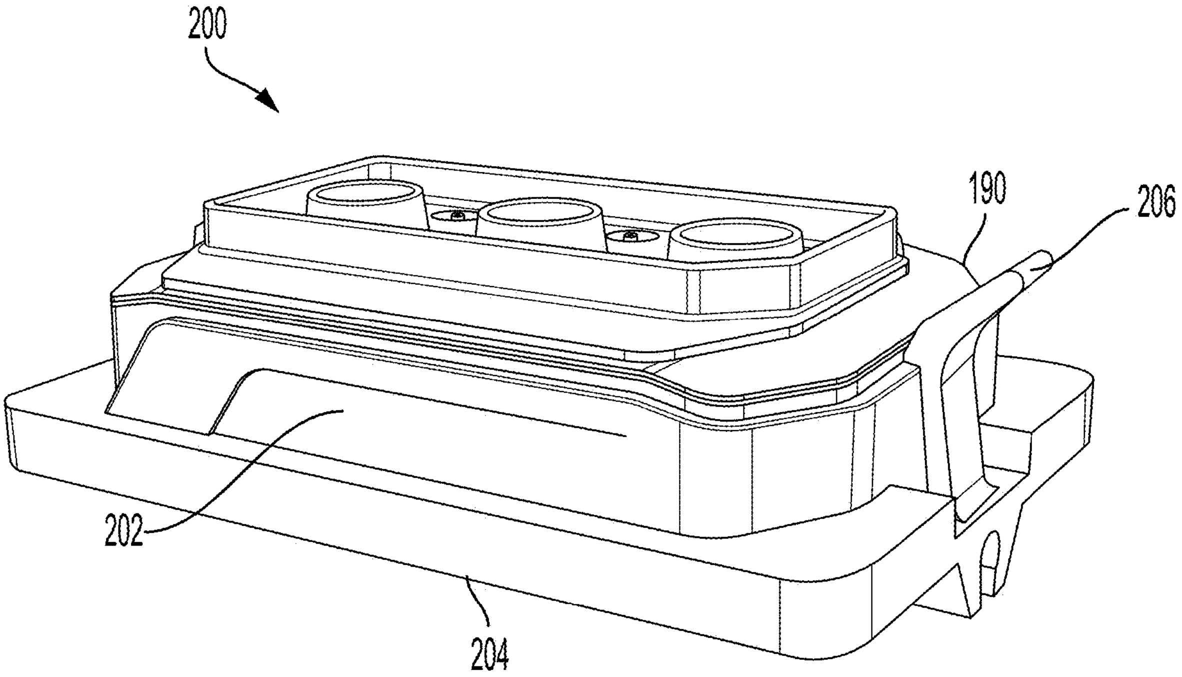
FIG. 46D illustrates an assembly for modeling organ-on-a-chip, according to aspects of the present embodiments.
Figure 72A:
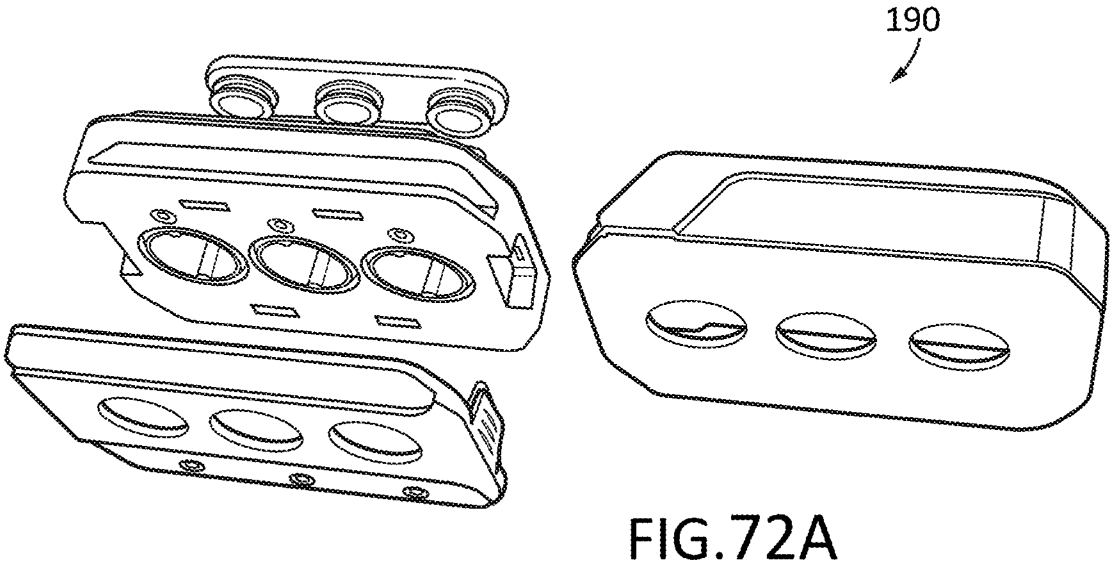
FIG. 72A illustrates an example of a cartridge, according to aspects of the present embodiments.
Figure 72B:
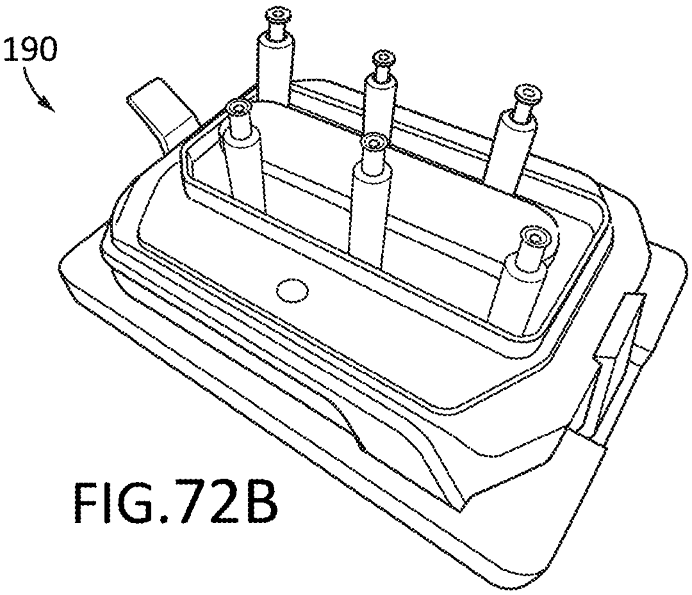
FIG. 72B illustrates an example of a cartridge, according to aspects of the present embodiments.

In some embodiments, a cartridge may not include any reservoirs, resulting in a shorter perfusion path to a scaffold. Such cartridge, for example, may be used for endothelial experiments. FIG. 46A illustrates an example of a cartridge 170, according to aspects of the present embodiments. The cartridge 170 may be used to perfuse a single scaffold. FIG. 46B illustrates an example of a cartridge 180, according to aspects of the present embodiments. The cartridge 180 may be used to perfuse three scaffolds. FIG. 46C illustrates an example of a cartridge 190, according to aspects of the present embodiments. The cartridge 190 may be used to perfuse two scaffolds. FIG. 46D illustrates an assembly 200 for modeling organ-on-a-chip, according to aspects of the present embodiments. The platform 200 may include a cartridge 190, a case 202, and a holder 204. The cartridge 190 may be positioned on top of the case 202, such that three scaffolds are disposed within the case 202. The cartridge may be sealed by a lid to maintain scaffold hydration and sterility. The holder 204 may include a holder clip 206 to secure the cartridge 190 and case 202. The holder 204 may be used in a robot system. FIGS. 72A and 72B illustrate examples of a cartridge 180, according to aspects of the present embodiments. The cartridge 180 may be used to perfuse three scaffolds.

Organ Systems

The present disclosure provides technologies to generate a model organ and/or tissue. In some aspects, the present disclosure provides methods to generate a model organ and/or tissue that includes a bioprinted entity, comprising a polymer (e.g., a hydrogel), and a cell associated with the bioprinted entity and/or seeded therein. In some embodiments, the model organ and/or tissue is one aspect of an ecosystem (e.g., organ-on-a-chip) which may be used for drug discovery and for assessing the effectiveness of various therapies. In some aspects, the model organ and/or tissue is optionally vascularized.

In some embodiments, the model organ and/or tissue is selected from an organ or tissue of the integumentary system, skeletal system, muscular system, nervous system, endocrine system, cardiovascular system, lymphatic system, respiratory system, digestive system, urinary system, and/or reproductive system.

In some embodiments, the model organ and/or tissue is an organ or tissue of the integumentary system. In some embodiments, the model organ is selected from the group consisting of an epidermis, a dermis, a hypodermis, a gland, a hair, and a nail.

In some embodiments, the model organ and/or tissue is an organ or tissue of the skeletal system. In some embodiments, the model organ is selected from the group consisting of a bone, a cartilage, a ligament, and a tendon.

In some embodiments, the model organ and/or tissue is an organ or tissue of the muscular system. In some embodiments, the model organ is selected from the group consisting of a skeletal muscle, a smooth muscle, and a cardiac muscle.

In some embodiments, the model organ and/or tissue is an organ or tissue of the nervous system. In some embodiments, the model organ is selected from the group consisting of a brain, a spinal cord, and a nerve.

In some embodiments, the model organ and/or tissue is an organ or tissue of the endocrine system. In some embodiments, the model organ is selected from the group consisting of a hypothalamus, a pineal gland, a pituitary gland, a thyroid gland, a parathyroid gland, a thymus, an adrenal gland, and a pancreas.

In some embodiments, the model organ and/or tissue is an organ or tissue of the cardiovascular system. In some embodiments, the model organ is selected from the group consisting of an artery, a vein, a blood vessel, a heart, and a lung.

In some embodiments, the model organ and/or tissue is an organ or tissue of the lymphatic system. In some embodiments, the model organ is selected from the group consisting of bone marrow, a spleen, a thymus, a lymph node, and a lymphatic vessel.

In some embodiments, the model organ and/or tissue is an organ or tissue of the respiratory system. In some embodiments, the model organ is selected from a lung, a nose, and a trachea.

In some embodiments, the model organ and/or tissue is an organ or tissue of the digestive system. In some such embodiments, the model organ is selected from a stomach, a gallbladder, a liver, a small intestine, a large intestine, a rectum, and an esophagus.

In some embodiments, the model organ and/or tissue is an organ or tissue of the urinary system. In some embodiments, the model organ is selected form a kidney and a bladder.

In some embodiments, the model organ and/or tissue is an organ or tissue of the reproductive system. In some embodiments, the model organ is selected from an ovary, a fallopian tube, a uterus, a cervix, a vagina, a prostate, and a teste.

In some embodiments, the model organ and/or tissue is a tumor.

In some embodiments, the model organ and/or tissue as described above and herein is patient-derived.

In some embodiments, the model organ and/or tissue as described above and herein is diseased or healthy. In some embodiments, the model organ and/or tissue as described above and herein is diseased. In some embodiments, the model organ and/or tissue as described above and herein is healthy.

In some embodiments, the model organ and/or tissue as described above and herein is an organ-on-a-chip.

In some aspects, the present disclosure provides methods to generate a model org Liver System In some embodiments, the model organ is a liver. In some aspects, a model liver comprises a cell chamber (to metabolize a biologically active material e.g., a drug), an access point (to enable delivery or sampling of a fluid(s) comprising a cell and/or a biologically active material), an inlet, and an outlet. In some embodiments, the model liver is vascularized. In some embodiments, the model liver is optionally vascularized. In some embodiments, the model liver is not vascularized.

FIG. 30-37E illustrate a model liver, according to aspects of the present embodiments.

FIG. 30-33 illustrate a model liver, according to aspects of the present embodiments. The model liver may include a scaffold comprising a bioprinted entity, a bile duct, a chamber, an inlet, an outlet, and optionally vasculature. In some such embodiments, the model liver may comprise a cell associated with the scaffold and/or seeded therein, wherein the cell is optionally an endothelial cell. In some embodiments, the model liver optionally comprises a cell associated with the vasculature and/or seeded therein, wherein the cell is optionally an LSEC. In some embodiments, the model liver optionally comprises a cell associated with the bile duct and/or seeded therein, wherein the cell is optionally a cholangiocyte. It will be appreciated by one of skill in the art that the association of a cell may occur with a combination of one or more aspects of the scaffold (e.g., bioprinted entity, bile duct, chamber, inlet, outlet, vasculature), and furthermore that a plurality of cell types may be associated with said scaffold.

Referring still to FIGS. 30-33, the chip 40 may include a first fluid network (i.e., vasculature 60) and a second fluid network (i.e., bile duct 80). The first and second fluid networks 60, 80 may be intertwined and or interconnected (i.e., with interlinking fluid passageways) without actually being fluidly coupled. Both the first and second fluid networks 60, 80 may be operatively coupled (for example functionally coupled) to the interstitial space and interstitial infill 58 disposed therein such that drugs and/or other biological substances that flow through either the first and/or second fluid networks 60, 80 may pass through the vasculature walls or bile duct walls and into the interstitial infill (i.e., to the active cells seeded therein).

FIG. 34-37 E illustrate a model liver, according to aspects of the present embodiments. The model liver may include a vasculature associated with a cell that comprises an interstitial pattern which may be characterized by fluorescence imaging, optionally wherein the interstitial pattern approximates the geometries of the cell and/or tissue(s) native format. In some embodiments, the interstitial pattern is spherical. In some embodiments, the interstitial pattern is fibrous. In some embodiments, the present disclosure provides a liver model (e.g., liver-on-a-chip) that shows improved cellular distribution relative to a comparable liver model (e.g., when comparing interstitial patterns via fluorescence imaging).

Figure 38:
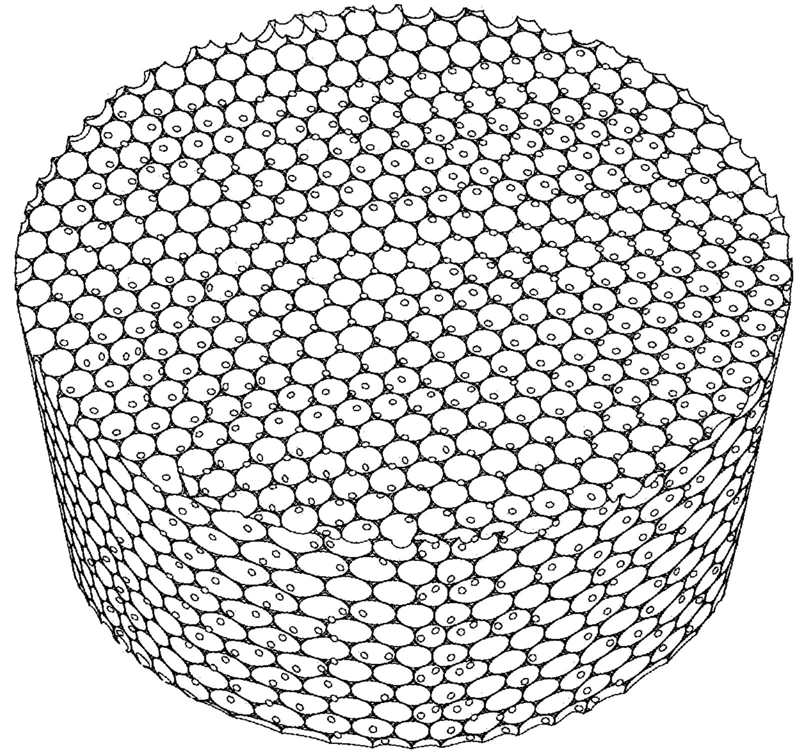
FIG. 38 illustrates a bioprinted scaffold, according to aspects of the present embodiments.

FIG. 38 illustrates a bioprinted scaffold, according to aspects of the present embodiments. The bioprinted scaffold may be inserted into well plates for 3D culture applications.

Figure 39:
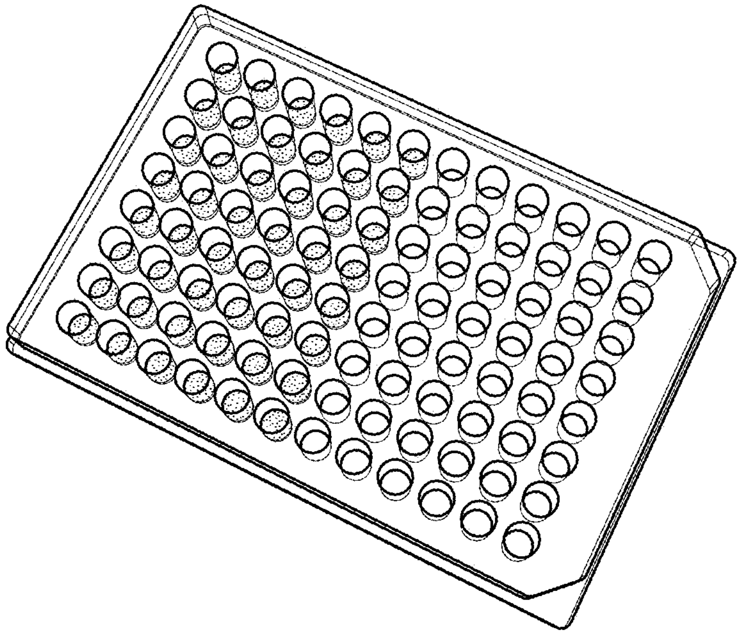
FIG. 39 illustrates bioprinted scaffolds inserted into a well plant, according to aspects of the present embodiments.

FIG. 39 illustrates bioprinted scaffolds inserted into a well plate, according to aspects of the present embodiments. In some embodiments, the well plate may include various numbers of wells, (for example, from about 6 wells to about 1536 wells) and may include bioprinted hydrogel scaffolds inserted in the wells, the scaffolds being coated with two reagents.

Figure 40A:
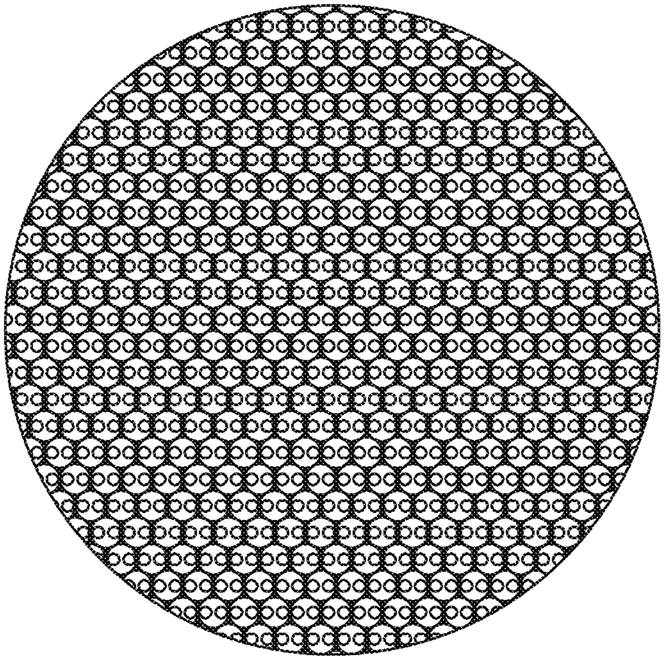
FIGS. 40A-40C illustrate top, front, and side views of a bioprinted scaffold, according to aspects of the present embodiments.
Figure 40B:
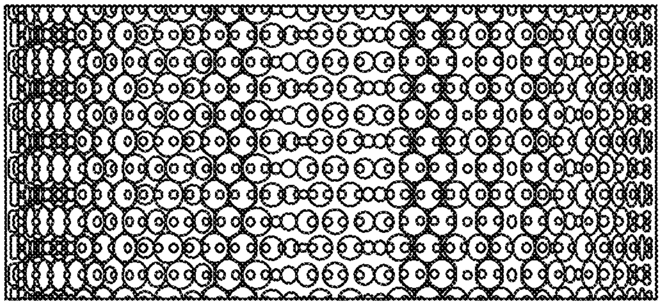
Figure 40C:
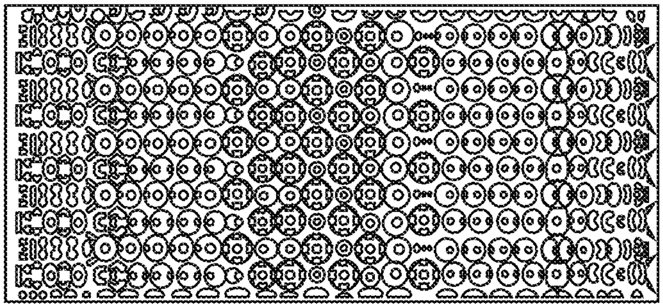

FIGS. 40A-40C illustrate top, front, and side views of a bioprinted scaffold, according to aspects of the present embodiments.

Delivery of Biologically Active Materials

In some embodiments, a scaffold, as described in the present disclosure, enables delivery of a biologically active material to a cell and/or tissue(s) via fluid(s) flowing through the scaffold. In some embodiments, a scaffold, as described in the present disclosure, enables delivery of a biologically active material to a cell and/or tissue(s) via fluid(s) flowing through the vasculature. In some such embodiments, delivery of the biologically active material occurs through vasculature walls.

In some embodiments, the biologically active material delivered via fluid(s) through the vasculature is selected from a group comprising a drug, a small molecule, a polypeptide, a peptidomimetic, a nucleic acid, a lipid, a lipid nanoparticle, an immunotherapeutic, a viral vector, and/or a cell. In some embodiments, the biologically active material delivered via fluid(s) through the vasculature is a drug. In some such embodiments, the drug is anti-inflammatory (e.g., Met-CCL5, cenicriviroc, belapectin, aspirin, GS-0976-WZ66, liraglutide, resmetirom). In some embodiments, the drug inhibits oxidative stress (e.g., oroxylin, methyl ferulic acid, GKT137831, losartan). In some embodiments, the drug inhibits hepatocyte apoptosis (e.g., VX-166, emricasan, pentoxifylline, β-elemene, selonsertib). In some embodiments, the drug inhibits ECM (e.g., halofuginone, FR(EtOH), BMS986263, simtuzumab). In some embodiments, the drug inhibits HSCs activation and proliferation (e.g., pirfenidone, fluorofenidone, praziquantel, ferulic acid, sorafenib, AZD6244, nilotinib, rilpirivine, saracatinib, pioglitazone, curcumin, pegbelfermin, NGM282, hydronidone, ICG001, PrI-724, octreotide, obeticholic acid, cilofexor, PX20606, rimonaban, SR141716A, JD5037, elafibranor, rosiglitazone, statins, sitagliptin, alogliptin).

In some embodiments, the biologically active material delivered via fluid(s) through the vasculature is a small molecule.

In some embodiments, the biologically active material delivered via fluid(s) through the vasculature is a polypeptide and/or variant thereof. In some embodiments, the polypeptide is selected from the group consisting of an antibody, an antibody fragment, a peptide, a protein, and/or variant thereof.

In some embodiments, the polypeptide is an antibody fragment and/or variant thereof.

In some embodiments, the polypeptide is a peptide and/or variant thereof.

In some embodiments, the polypeptide is a protein and/or variant thereof.

In some embodiments, the biologically active material delivered via fluid(s) through the vasculature is a peptidomimetic or variant thereof.

In some embodiments, the biologically active material delivered via fluid(s) through the vasculature is a nucleic acid or variant thereof. In some embodiments, the nucleic acid is selected from the group consisting of siRNA, tRNA, rRNA, mRNA, miRNA, gRNA, DNA, and/or variant thereof. In some embodiments, the nucleic acid is a siRNA and/or variant thereof.

In some embodiments, the nucleic acid is a tRNA and/or variant thereof.

In some embodiments, the nucleic acid is a rRNA and/or variant thereof.

In some embodiments, the nucleic acid is a mRNA and/or variant thereof.

In some embodiments, the nucleic acid is a mRNA and/or variant thereof.

In some embodiments, the nucleic acid is a gRNA and/or variant thereof.

In some embodiments, the nucleic acid is a DNA and/or variant thereof.

In some embodiments, the biologically active material delivered via fluid(s) through the vasculature is a lipid and/or variant thereof.

In some embodiments, the biologically active material delivered via fluid(s) through the vasculature is a lipid nanoparticle and/or variant thereof. In some embodiments, the lipid nanoparticle may or may not comprise a payload, wherein the payload is selected from a group consisting of a small molecule, a nucleic acid (e.g., mRNA), and/or a polypeptide.

In some embodiments, the biologically active material delivered via fluid(s) through the vasculature is an immunotherapeutic or variant thereof.

In some embodiments, the biologically active material delivered via fluid(s) through the vasculature is a viral vector. In some embodiments, the viral vector may or may not comprise a payload, wherein the payload is selected from a group consisting of a small molecule, a nucleic acid (e.g., mRNA), and/or a polypeptide. In some embodiments, the viral vector is an adeno-associated virus (AAV) and/or variant thereof. In some such embodiments, the AAV is selected from the group consisting of AAV1, AAV2, AAV3, AAV4, AAV5, AAV6, AAV6.2, AAV7, AAV8, AAV9, AAVrh10, AAVDJ, AAVDJ/8, AAVPHP.eB, AAVPHP.S, AAV2-QuadYF, and/or AAV2.7m8. In some embodiments, the AAV is AAV1. In some embodiments, the AAV is AAV2. In some embodiments, the AAV is AAV3. In some embodiments, the AAV is AAV4. In some embodiments, the AAV is AAV5. In some embodiments, the AAV is AAV6. In some embodiments, the AAV is AAV6.2. In some embodiments, the AAV is AAV7. In some embodiments, the AAV is AAV8. In some embodiments, the AAV is AAV9. In some embodiments, the AAV is AAVrh10. In some embodiments, the AAV is AAVDJ. In some embodiments, the AAV is AAVDJ/8. In some embodiments, the AAV is AAVPHP.eB. In some embodiments, the AAV is AAVPHP.S. In some embodiments, the AAV is AAV2-QuadYF. In some embodiments, the AAV is AAV2.7m8.

In some embodiments, the biologically active material delivered via fluid(s) through the vasculature is a cell and/or variant thereof. In some such embodiments, the cell is selected from the group consisting of a T cell, a PBMC, a pluripotent stem cell (PSC), an adult stem cell (ASC), an embryonic stem cell, a cancer stem cell (CSC), a hematopoietic progenitor cell (HPC), a myeloid stem cell, a monocyte, a lymphocyte, a granulocyte, a patient-derived cell (e.g., a tumor cell), a chimeric antigen receptor (CAR)-positive T cell, and/or a $CD54^+$ cell.

Those skilled in the art, reading the present disclosure, will appreciate that, in some embodiments, the biologically active material delivered via fluid(s) through the vasculature may be adjusted, for example to comprise a plurality of materials (e.g., a combination of a polypeptide and/or a small molecule), which may be the same or different.

As described herein, use of a variety of biologically active materials is contemplated as compatible with various embodiments. In some embodiments, a biologically active material is or comprises a detectable moiety.

Detection of a Detectable Moiety

As is described herein, detecting (e.g., detecting a signal, such as a biomarker or detectable moiety), as applicable to methods and compositions described herein, may be achieved in any application-appropriate manner. For example, in some embodiments, a step of detecting is or comprises an immunological assay, a nucleic acid amplification assay, a fluorescence assay (e.g., a calf intestinal alkaline phosphatase (CIP) assay), a luminescence assay, a colorimetric assay (e.g., a urea-associated assay), an albumin binding assay, genomics, proteomics, transcriptomics (e.g., spatial transcriptomics), an RNA expression assay, metabolomics (e.g., an ATP-associated assay), and/or immunohistochemistry.

As is described herein, many embodiments include the use of one or more biological samples (e.g., a sample of fluid or tissue taken from an organ system), and the manner of detecting a biomarker and/or detectable moiety may vary depending upon the biological sample used in a particular embodiment. In accordance with the present disclosure, any of a variety of biological samples are contemplated as compatible with various embodiments. For example, in some embodiments, a biological sample is or comprises a fluid(s) from the chamber of the organ system.

In accordance with various embodiments, and depending upon the specific biomarker(s) used, one of skill in the art will envision one or more appropriate methods of detecting or determining the presence and/or quantity/level of a biomarker and/or detectable moiety in a biological sample. In some embodiments, a biomarker and/or detectable moiety may be detected using any of a variety of modalities including fluorescence, radioactivity, chemiluminescence, electrochemiluminescence, colorimetry, FRET, HTRF, isotopic methods, partner binding (e.g., biotin/avidin, antibodies, hybridization), or any other known manner of detecting a biomarker and/or detectable moiety. In some embodiments, a biomarker and/or detectable moiety may be detected through binding of a detectable moiety (e.g., an exogenously added detectable moiety) such as an antibody that includes, for example, a tag in accordance with one or more of the above modalities, or an enzyme (e.g., luciferase, n-gal).

Those skilled in the art will readily appreciate that the methods described herein can be useful in a variety of applications involving monitoring a detectable moiety within a model organ-on-a-chip (e.g., a healthy or disease model) after the delivery of a biologically active material. In some embodiments, methods described herein may be useful in assessing whether or not a detectable moieties levels are abnormal, relative to a desired or "normal" level of expression. In some embodiments, methods described herein may be used to predict or characterize a potential reaction to a biologically active material (e.g., a disease model responds to the biologically active material favorably by exhibiting a decrease in the metric used to determine said diseased state), thus potentially allowing for the enablement, prevention and/or mitigation of the reaction, based on the desired outcome.

Characterization of a Scaffold

Those skilled in the art, reading the present specification, will appreciate that it may be desirable to characterize one or more features of bioprinted entities independent of a cell and/or associated with a cell, and/or of components or combinations thereof, for example when designing (e.g., selecting appropriate components of) or producing a provided system and/or when monitoring or assessing a preparation thereof. Alternatively or additionally, in some embodiments, it may be desirable to assess one or more features of a provided system as administered, for example in order to monitor a subject and/or treatment thereof.

In some embodiments, cellular distribution is a characteristic property of a system and/or bioprinted entity associated with a cell and/or seeded therein. In some embodiments, the present disclosure provides systems and/or bioprinted entities that show improved cellular distribution relative to a comparable system and/or bioprinted entity.

Those skilled in the art, reading the present specification, will appreciate that it may be desirable to characterize one or more features of bioprinted entities, and/or of components or combinations thereof, for example when designing (e.g., selecting appropriate components of) or producing a provided system and/or when monitoring or assessing a preparation thereof. Alternatively or additionally, in some embodiments, it may be desirable to assess one or more features of a provided system as administered, for example in order to monitor a subject or treatment thereof.

Exemplification

The present example demonstrates that hydrogel scaffolds described herein achieve cell growth (e.g., cell culture) for a sustained duration of time and under conditions that reproduce a physiological (e.g., natural, endogenous) environment.

Preparing Scaffolds for Coating

Hydrogel scaffolds described herein are placed in a 12 well plate in phosphate buffered saline (PBS) and exposed to UV for 2 hours. The hydrogel scaffolds are carefully removed from the wells and placed upside down in a sterile petri-dish. H-VIOS2-DF chips are primed with 1×PBS to ensure there are droplets at both the inlet and outlet. The hydrogel is assembled in the chip and 150-600 uL of collagen type I (Col1) is added to the well of the hydrogel. Collagen calculations were performed as previously described. Female luers are assembled at the inlets and outlets of the h-Vios2 chips and capped with male caps. Chips are placed in the incubator at 37° C. for 1 hour.

Vasculature Washing and ECM Coating

Using a syringe pump, 250-750 uL 1×PBS was perfused through each hydrogel to remove air trapped in the vasculature followed by perfusion of 100-300 uL 10× penicillin/streptomycin (pen/strep) and 10× amphotericin B (Amp B). The vasculature was washed with 250-750 uL 1×PBS and 20-60 mg of Acrylated-PEG-$OCH_2CH_2CH_2CH_2CO_2$—NHS (SVA) was dissolved in 1-4 mL of 1% Lithium phenyl-2,4,6-trimethylbenzoylphosphinate (LAP) solution (Dulbecco's PBS). The SVA solution was added to the vasculature using a syringe pump at 50-200 ul/min. The hydrogel scaffolds was then placed under UV for 20 minutes. The channels (e.g., vasculature) was washed with 200-700 uL 1× Dulbecco's PBS (DPBS). A collagen coating (e.g., ECM) solution was prepared as previously described. Each hydrogel were perfused with 50-300 uL ECM solution at 20-75 uL/min. Excess liquid from the (+) side of the chip aspirated. The inlets and outlets were capped with male caps and the hydrogel scaffolds incubated for 1-3 hours at 37° C. The vasculature was washed with 200-500 uL DPBS at 50-200 uL/min. Hydrogel scaffolds were filled with 300 uL-1100 uL EGM (cAP-02, Angio-Proteomie) medium containing P/S and AmpB for equilibration before being placed in an incubator at 37° C. overnight. The EGM solution was emptied form the hydrogel wells while cells were prepared.

Preparing GFP Tagged Human Umbilical Vein Endothelial Cells (HUVEC)

HUVEC cells (e.g., cells) were washed 2× with PBS and detached using 0.05% Trypsin. EGM was then added to the well at an equal volume to trypsin. Cells were centrifuged at 200 g for 5 minutes and then resuspended in medium. Cells were subsequently counted.

Preparing EGM Medium for Cell

AmpB was added to EGM to prevent fungal contamination of hydrogels. HUVECs were resuspended in EGM at 200,000 cells/$cm^2$.

Seeding HUVECs

The chip was attached to the syringe pump and 200 μL of cell suspension was slowly perfused at the (−) side of the chip at 50 uL/min and through the vasculature. This was carried out for all hydrogel scaffolds. The inlets and outlets are then capped and the lids of the chips closed. The chip was then loaded on a programmable rotator for rotation at 1 rotation per minutes for 4 hours.

Imaging D2 GFP-HUVEC Cells

Stable attachment of GFP-tagged HUVECs were assessed using a 4× objective (EVOS microscope) using a Z-stack and custom imaging plate. Fresh EGM was added to the wells of the hydrogel after imaging. On day 3, cells were imaged as previously described while the chip was connected to a syringe pump. While imaging, the syringe pump was set at a flow rate of 5 uL/min to 70 uL/min to determine the flow rate which the cells could tolerate (e.g., did not detach). Once the optimal flow rate was determined, tubing of a peristaltic pump was primed with EGM and connected to the chip inlets and outlets. Perfusion was started, with 150 uL to 450 uL fresh EGM medium added to the wells every 24 hours. The reservoir was replenished with fresh medium every 48 hours. Hydrogels containing cells were imaged on day 1, day 3, day 7, day 10, and day 14. On day 14, cells were fixed by perfusing 4% paraformaldehyde through the hydrogels. Fixation occurred overnight at 4° C. Assessment of cell morphology and coverage (e.g., confluency) was assessed using fluorescence confocal microscopy to visualize GFP, actin, ZO-1, CD-31 and Hoechst staining.

We claim:

1. A system comprising:
a multi-part assembly comprising:
at least one inlet flow line configured to deliver a fluid to an interior volume of the multi-part assembly; and
at least one outlet flow line configured to deliver the fluid from the interior volume of the multi-part assembly;
a 3D-printed hydrogel chip housed within the interior volume of the multi-part assembly, the 3D-printed hydrogel chip comprising:
at least one inlet flow passage disposed within the 3D-printed hydrogel chip and fluidly coupled to the at least one inlet flow line;
at least one outlet flow passage disposed within the 3D-printed hydrogel chip and fluidly coupled to the at least one outlet flow line,
wherein the at least one inlet flow passage transitions to the at least one outlet flow passage within an interstitial space disposed within the 3D-printed hydrogel chip,
wherein the interstitial space is accessible from a top of the 3D-printed hydrogel chip via an access port disposed therein; and
an interstitial infill disposed within the interstitial space,
wherein voids in the 3D-printed hydrogel chip form each of the at least one inlet flow passage, the at least one outlet flow passage, and the interstitial space;

at least one live cell seeded within the interstitial space;

a fluid reservoir fluidly coupled downstream of the at least one inlet flow line and upstream of the at least one inlet flow passage;

a pump disposed downstream of the fluid reservoir and upstream of the at least one inlet flow passage; and at least one sampling port and/or fluid sampling line fluidly coupled to at least one of the fluid reservoir, the at least one outlet flow line, the at least one outlet flow passage, the interstitial space and/or another system flow passage;

wherein the multi-part assembly and the 3D-printed hydrogel chip are composed of different materials;

wherein at least one of the at least one inlet flow passage and the at least one outlet flow passage comprises at least one micropore disposed therein, in a portion of a passage disposed within the interstitial space;

wherein the at least one inlet flow passage and the at least one outlet flow passage collectively form a vasculature; and wherein the at least one micropore connects the vasculature to the interstitial space.

2. The system of claim 1, wherein each of the multi-part assembly and the 3D-printed hydrogel chip are formed via an additive manufacturing process.

3. The system of claim 1, wherein each of the at least one inlet flow passage and the at least one outlet flow passage comprises at least two inlet or outlet flow passages, thereby forming at least two unconnected fluid flow passages through the 3D-printed hydrogel chip, wherein each of the at least two unconnected fluid flow passages contains a different fluid comprising at least one of blood and bile, and wherein at least one of the at least two inlet or outlet flow passages is seeded with cholangiocytes.

4. The system of claim 1, wherein each of the at least one inlet flow passage and the at least one outlet flow passage comprises a single respective inlet or outlet portion which branches into a network of connected flow passages, comprising a network of inlet flow passages fluidly connected to a corresponding network of outlet flow passages within the interstitial space.

5. The system of claim 1, wherein the at least one micropore comprises an internal diameter in a range from about 40 μm to about 60 μm.

6. The system of claim 1, further comprising at least one precursor comprising acrylated-PEGlk-NHS disposed on the 3D-printed hydrogel chip.

7. The system of claim 6, wherein the at least one precursor further comprises a photoinitiator.

8. The system of claim 1, further comprising at least one bioactive coating comprising at least one of gelatin methacrylate (GelMA) and collagen methacrylate (ColMA), wherein the at least one bioactive coating is disposed on a surface of the at least one inlet flow passage and/or the at least one outlet flow passage.

9. The system of claim 1, wherein the at least one live cell comprises at least one of a biliary endothelial cell, a cholangiocyte, a hepatic stellate cell (HSCs), a mucous cell, a parietal cell, a cardiac fibroblast (CF), a Paneth cell, a Merkel cell, a seminiferous tubule, a tubule epithelial cell, a macula densa cell, a glomerular endothelial cell, a podocyte, a mesangial cell, a parietal epithelial cell, an immortalized cell, a T cell, and/or a peripheral blood mononuclear cell (PBMC).

10. The system of claim 1, further comprising:

a covalent linker attached to a hydrogel material; and collagen attached to the covalent linker.

11. The system of claim 9, further comprising:

at least one precursor covalently tethered to a hydrogel material; and at least one bioactive coating covalently bonded to the at least one precursor;

wherein the at least one live cell is attached to the at least one bioactive coating.

12. The system of claim 1, further comprising a removable top cover or lid enabling access to the interior volume, wherein the interstitial space is accessible when the top cover or lid is removed.

13. The system of claim 1, wherein the interstitial infill comprises a hydrogel and a 3D-printed repeating lattice structure.

14. The system of claim 1, wherein the interstitial infill comprises a plurality of spherical pores, wherein the plurality of spherical pores are connected via a plurality of interconnects.

15. The system of claim 1, wherein the interstitial infill comprises one or more integral handles.

16. The system of claim 1, further comprising one or more sensors disposed within the at least one inlet flow passage, the at least one outlet flow passage, and/or the interstitial space, wherein the one or more sensors comprise sensors for measuring luminescence, colorimetry, electrochemical activity, fluorescence, and/or metabolic activity.

17. The system of claim 1, further comprising at least one endothelial cell attached to an interior surface of the at least one inlet flow passage and/or the at least one outlet flow passage.

18. The system of claim 17, further comprising at least one of a human umbilical vein endothelial cell (HUVEC), an induced pluripotent stem cell (iPSC), a primary liver sinusoidal endothelial cell (LSEC), and a cholangiocyte seeded in the interstitial space and supported by the interstitial infill.

19. The system of claim 1, wherein the 3D-printed hydrogel chip comprises at least one of PEGMA (Polyethylene glycol methyl ether methacrylate), thiolated gelatin, thiolated collagen, methacrylated chitosan, thiolated chitosan, methacrylated heparin, thiolated heparin, thiolated hyaluronic acid, multi-arm PEG-maleimide, multi-arm PEG-thiol, multi-arm PEG-DBCO, multi-arm PEG-N3, and multi-arm PEG-biotin with streptavidin.

20. The system of claim 1, wherein the 3D-printed hydrogel chip comprises a photo-initiator and a photo-absorber comprising tartrazine.

* * * * *